United States Patent [19]
Aoki et al.

[11] Patent Number: 5,260,177
[45] Date of Patent: Nov. 9, 1993

[54] SILVER HALIDE COLOR PHOTOGRAPHIC LIGHT-SENSITIVE MATERIAL

[75] Inventors: Kozo Aoki; Michio Ono; Katsuyoshi Yamakawa; Shigeru Yamazaki; Kei Sakanoue; Hidetoshi Kobayashi, all of Kanagawa, Japan

[73] Assignee: Fuji Photo Film Co., Ltd., Minami-Ashigara, Japan

[21] Appl. No.: 884,897

[22] Filed: May 18, 1992

Related U.S. Application Data

[63] Continuation of Ser. No. 584,651, Sep. 19, 1990, abandoned, which is a continuation-in-part of Ser. No. 324,560, Mar. 16, 1989, abandoned.

[30] Foreign Application Priority Data

Mar. 16, 1988 [JP] Japan ................................ 63-62825
Sep. 19, 1988 [JP] Japan ................................ 1-242633

[51] Int. Cl.[5] ........................ G03C 7/38; G03C 7/388
[52] U.S. Cl. .................................... 430/505; 430/556; 430/557; 430/558
[58] Field of Search ............... 430/558, 384, 385, 505, 430/556, 557, 546

[56] References Cited

U.S. PATENT DOCUMENTS 2,293,004 8/1942 Lohaus ................................ 430/558
2,525,502 10/1950 Tulagin et al. ....................... 430/384
2,717,831 9/1955 Tulagin et al. ....................... 430/558
4,970,142 11/1990 Kaneko .............................. 430/558

FOREIGN PATENT DOCUMENTS 564713 3/1944 United Kingdom ................ 430/558

*Primary Examiner*—Lee C. Wright
*Attorney, Agent, or Firm*—Burns, Doane, Swecker & Mathis

[57] ABSTRACT

A silver halide color photographic light-sensitive material comprises a novel cyan dye-forming coupler or a combination of a specific cyan dye-forming coupler with an $\alpha$-pivaloylacetoanilide type yellow dye-forming coupler or a pyrazoloazole type magenta dye-forming coupler, the specific cyan dye-forming coupler being contained in the silver halide emulsion layer in the form of an emulsion of lipophilic fine particles obtained by mixing the coupler with at least one water-insoluble and organic solvent-soluble homo- or co-polymer to form a dispersion. The silver halide color photographic light-sensitive material is excellent in the reproduction of yellow, magenta and cyan colors and has low fog of cyan. Thus, the light-sensitive material can provide color images excellent in the fastness of the cyan color images.

The cyan dye-forming coupler is represented by general formula (II):

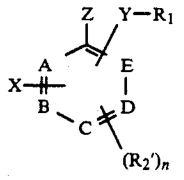

(II)

wherein $R_1$ represents an aliphatic group, an aromatic group or a heterocyclic group; $R_2$ represents a group or atom which can be bonded with the heterocyclic ring; X represents a hydrogen atom or a group which can be eliminated; Y represents a divalent bonding group having at least one amido bond and/or ester bond; Z represents a dissociative group; A, B, C, D and E each represents a nitrogen atom or a carbon atom a which hydrogen atom is bonded, provided that one or two of them represent a nitrogen atom; and n represents 0, 1 or 2.

17 Claims, No Drawings

SILVER HALIDE COLOR PHOTOGRAPHIC LIGHT-SENSITIVE MATERIAL

This application is a continuation of application Ser. No. 07/584,651, filed Sep. 19, 1990, now abandoned which is a CIP of Ser. No. 07/324,560, filed Mar. 16, 1989, now abandoned.

BACKGROUND OF THE INVENTION

The present invention relates to a silver halide color photographic light-sensitive material and more particularly to a silver halide color photographic light-sensitive material containing a novel cyan coupler, which is excellent in color reproduction properties and improved in storability of images, particularly in fastness.

Silver halide color photographic light-sensitive materials comprise a substrate provided thereon with multilayered light-sensitive layers which comprise three kinds of silver halide emulsion layers selectively sensitized so as to be selectively sensitive to blue, green and red light rays, respectively.

A color image is formed by exposing such a silver halide photographic light-sensitive material to light and then subjecting it to a color developing treatment in which a developing agent such as an aromatic primary amine is oxidized with the silver halide and the oxidized developing agent is reacted with a dye-forming coupler. In this process, colors are reproduced by a subtractive color photography in which blue, green and red colors are reproduced by forming images with yellow, magenta and cyan dyes which are complementary colors. In this case, couplers Preferably used must undergo a coupling reaction at a high rate, provide a high color density within a limited developing time and have good color-developing (or dye-forming) properties. In addition, the color-developing dye formed through the coupling reaction must be clear cyan, magenta and yellow dyes which have low minor absorption and can provide color photographic images with good color reproduction properties.

On the other hand, color photographic images thus formed must have good storability under various conditions such as dark storage conditions wherein the images are greatly influenced by humidity, heat or the like and those in which the images are irradiated with rays such as solar rays and indoor lighting rays. Decoloration and change of color of the images as well as yellowing of non-image portions are very serious problems in particular in color print materials.

Couplers serving as color image-forming agents play an important role in achieving the foregoing requirements of the color photographic light-sensitive materials. For this reason, couplers have been improved through the modification of the structures thereof.

Phenol derivatives and naphthol derivatives have conventionally been employed as cyan color image-forming couplers, but the color images formed from these couplers show not only absorption in the desired red region but also unnecessary absorption in the blue and green regions and thus the properties of these cyan couplers are still insufficient. There are also some problems of stability of the color images formed with the phenol derivatives and naphthol derivatives. For instance, color images formed with 2-acylaminophenol cyan couplers disclosed in U.S. Pat. Nos. 2,367,531; 2,369,929; 2,423,730 and 2,801,171 usually have poor fastness to heat, those formed with 2,5-diacylaminophenol cyan couplers disclosed in U.S. Pat. Nos. 2,772,162 and 2,895,826 usually have poor fastness to light and those formed with 1-hydroxy-2-naphthamide cyan couplers usually have poor fastness to both light and heat (particularly to heat and humidity).

Couplers free of these defects of the cyan dye-forming couplers have been developed. They include, for instance, 5-hydroxy-6-acylaminocarbostyryl cyan couplers disclosed in U.S. Pat. Nos. 4,327,173 and 4,564,586; and 4-hydroxy-5-acylaminoxyindole couplers and 4-hydroxy-5-acylamino-2,3-dihydro-1,3-benzimidazol-2-one couplers disclosed in U.S. Pat. No. 4,430,423. These couplers have excellent resistance to light and fastness to heat. They are specific couplers having a hetero atom in the color-developing mother nucleus. The rings having a color-developing dissociative group have the same valence as that of phenol.

As for the couplers having a hetero atom in the ring which has a dissociative group, only 3-hydroxypyridine and 2,6-dihydroxypyridine are disclosed in U.S. Pat. No. 2,293,004. However, when 3-hydroxypyridine described in this U.S. Patent is used, it absorbs light in very short wavelength regions and the absorption peak thereof is broad. Further 3-hydroxypyridine is soluble in water. Therefore, 3-hydroxypyridine can not be used as the so-called cyan coupler.

There have been proposed couplers which are obtained by introducing an appropriate group resistant to diffusion into pyridines or pyrimidines substituted with a dissociative group such as a hydroxyl group and which provide a cyan dye excellent in absorption characteristics. However, they are still liable to cause color fog and decoloration towards dark color.

SUMMARY OF THE INVENTION

Accordingly, a first object of the present invention is to provide a silver halide color photographic light-sensitive material excellent in color reproduction characteristics.

A second object of the present invention is to provide a silver halide color photographic light-sensitive material showing low color fog during development processing.

A third object of the present invention is to provide a silver halide color photographic light-sensitive material whose fastness of cyan color images is improved.

These and other objects of the present invention will be apparent from the following description and Examples The inventors of this invention have conducted various studies and have found out that the foregoing objects of the present invention can effectively be achieved by providing the following silver halide color photographic light-sensitive materials:

(1) A silver halide color photographic light-sensitive material comprises a substrate provided thereon with a hydrophilic colloidal layer containing at least one cyan dye-forming coupler represented by the following general formula (I):

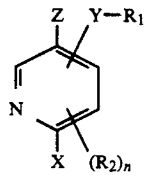

(I)

wherein $R_1$ represents an aliphatic group, an aromatic group or a heterocyclic group; $R_2$ represents a group or atom which can be bonded with the pyridine ring; X represents a hydrogen atom or a group which can be eliminated; Y represents a divalent bonding group having at least one amido bond and/or ester bond; Z represents a group which can be dissociated; and n represents 0, or 2 with the proviso that when n is 2, two $R_2$s may be the same or different groups or atoms or they may be bonded together to form a ring; that when n is 1 or more, $R_1$ may form a ring together with $R_1$; that at least one of $R_1$, $R_2$ and X may have, as substituent(s), one or more pyridyl residues of general formula (I) from which $R_1$, $R_2$ or X has been removed; that when n is 2, one of $R_2$s is a hydroxyl group, the hydroxyl group is at o- or p-position with respect to the nitrogen atom of the pyridyl ring and the other $R_2$ can be bonded with the nitrogen atom of the pyridyl group; and that the hydroxyl group at o- or p-position can form a ketone through tautomerism.

(2) A silver halide color photographic light-sensitive material comprises a substrate provided thereon with at least one layer of a silver halide emulsion containing a yellow dye-forming coupler, at least one layer of a silver halide emulsion containing a magenta dye-forming coupler and at least one layer of a silver halide emulsion containing a cyan dye-forming coupler wherein the cyan dye forming coupler is a coupler represented by the following general formula (11) and the yellow dye-forming coupler is an α-pivaloylaceto-anilide type yellow dye forming coupler:

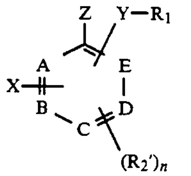

(II)

wherein $R_1$ represents an aliphatic group, an aromatic group or a heterocyclic group; $R_2'$ represents a group or atom which can be bonded with the heterocyclic ring; X represents a hydrogen atom or a group which can be eliminated; Y represents a divalent bonding group having at least one amido bond and/or ester bond; Z represents a dissociative group; A, B, C, D and E each represents a nitrogen atom or a carbon atom to a which hydrogen atom is bonded, provided that one or two of them represent a nitrogen atom; and n represents 0, 1 or 2 with the proviso that when n is 2, two $R_2'$s may be the same or different groups or atoms or they may be bonded together to form a ring, that when n is 1 or more, $R_1$ may form a ring together with $R_2'$; at least one of $R_1$, $R_2'$ and X may have, as substituents, one or more heterocyclic residues of general formula (II) from which $R_1$, $R_2'$ or X has been removed; and that when n is 2, one of $R_2'$s is a hydroxyl group, the hydroxyl group being at an o- or p-position with respect to a nitrogen atom of the heterocyclic ring and the other $R_2'$ can be bonded with the nitrogen atom of the heterocyclic ring, the hydroxyl group bonded at the o- or p-position, in this case, being able to form a ketone through tautomerism.

(3) A silver halide color photographic light-sensitive material comprises a substrate provided thereon with at least one layer of a silver halide emulsion containing an yellow dye-forming coupler, at least one layer of a silver halide emulsion containing a magenta dye-forming coupler and at least one layer of a silver halide emulsion containing a cyan dye-forming coupler wherein the cyan dye-forming coupler is a coupler represented by the foregoing general formula (II) and the magenta dye-forming coupler is a pyrazoloazole type magenta dye forming coupler.

(4) A silver halide color photographic light-sensitive material comprises a substrate provided thereon with at least one layer of a silver halide emulsion containing an yellow dye-forming coupler, at least one layer of a silver halide emulsion containing a magenta dye-forming coupler and at least one layer of a silver halide emulsion containing a cyan dye-forming coupler wherein the cyan dye forming coupler is a coupler represented by the foregoing general formula (II) and the cyan dye-forming coupler is incorporated into the silver halide emulsion layer in the form of an emulsion of lipophilic fine particles obtained by admixing it with at least one water-insoluble and organic solvent-soluble homo- or co-polymer to form a dispersion of the mixture.

DETAILED EXPLANATION OF THE INVENTION

The silver halide color photographic light sensitive materials according to the present invention will hereunder be explained in more detail.

First the cyan couplers represented by the general formulae (I) and (II) will be described.

$R_1$ in Formulae (I) and (II) represents an aliphatic group preferably having 1 to 36 carbon atoms, an aromatic group preferably having 6 to 36 carbon atoms such as a phenyl or naphthyl group, or a heterocyclic group such as a 3-pyridyl, 2-furyl or morpholino group.

The term "aliphatic groups" herein means straight, branched or cyclic aliphatic hydrocarbon groups. They include saturated and unsaturated aliphatic hydrocarbon groups such as alkyl, alkenyl and alkynyl groups. Typical examples thereof are methyl, ethyl, butyl, dodecyl, octadecyl, eicosenyl, isopropyl, t-butyl, t-octyl, t-dodecyl, cyclohexyl, cyclopentyl, allyl, vinyl, 2-hexadecenyl and propargyl groups.

The term "aromatic groups" herein means monocyclic or condensed polycyclic aromatic hydrocarbon groups. The term "heterocyclic groups" herein means cyclic groups consisting of not only carbon atoms but also at least one hetero atom such as O, S, N or P in the ring. The heterocyclic groups comprise a 3-to 8-membered ring, preferably a 5- to 6-membered ring and, if desired, the heterocyclic ring may be condensed with each other or it may be condensed with a benzene ring. They also include non aromatic cyclic groups.

The aliphatic groups, aromatic groups and heterocyclic groups represented by $R_1$ may further be substituted with groups selected from the group consisting of alkyl groups, aryl groups, heterocyclic groups, alkoxy groups such as methoxy and 2-methoxyethoxy groups, aryloxy groups such as 2,4 di-t-amylphenoxy, 2-chlorophenoxy and 4-cyanophenoxy group, alkenyloxy groups such as 2-propenyloxy group, amino groups such as butylamino, dimethylamino, anilino and N methylanilino groups, acyl groups such as acetyl and benzoyl groups, ester groups such as butoxycarbonyl, phenoxycarbonyl, acetoxy, benzoyloxy, butoxysulfonyl and toluenesulfonyloxy groups, amido groups such as acetylamido, ethylcarbamoyl, dimethylcarbamoyl, methanesulfonamido and butylsulfamoyl groups, sulfamido groups such as dipropylsulfamoylamino group, imido groups such as succinimido and hydantoinyl groups, ureido groups such as phenylureido and dimethylureido groups, aliphatic and aromatic sulfonyl groups such as methanesulfonyl and phenylsulfonyl groups, aliphatic and aromatic thio groups such as ethylthio and phenyl thio groups, hydroxyl group, cyano group, carboxyl group, nitro group, sulfo group and halogen atoms.

$R_2$ or $R_2'$ is a group which can be bonded with the pyridine ring or the heterocyclic ring respectively and preferred examples thereof are aliphatic groups such as methyl, ethyl, butyl and dodecyl groups, aromatic groups such as phenyl and naphthyl groups, heterocyclic groups such as 3-pyridyl and 2-furyl groups, alkoxy groups such as methoxy and 2-methoxyethoxy groups, aryloxy groups such as 2,4-di-t-amylphenoxy, 2-chlorophenoxy and 4-cyanophenoxy groups, alkenyloxy groups such as 2-propenyloxy group, amino groups such as butylamino, dimethylamino, anilino and N-methylanilino groups, acyl groups such as acetyl and benzoyl groups, ester groups such as butoxycarbonyl, phenoxycarbonyl, acetoxy, benzoyloxy, butoxysulfonyl and toluenesulfonyloxy groups, amido groups such as acetylamido, ethylcarbamoyl, dimethylcarbamoyl, methanesulfonylamido and butylsulfamoyl groups, sulfamido groups such as dipropylsulfamoylamino group, imido groups such as succinimido and hydantoinyl groups, ureido groups, aliphatic and aromatic sulfonyl groups, aliphatic and aromatic thio groups, hydroxyl group, carboxyl group and halogen atoms.

These groups may have substituents and specific examples thereof are the same as those listed above in connection with $R_1$. $R_2$ or $R_2'$ can be bonded with the nitrogen atom of the pyridine ring or the heterocyclic ring respectively. In this case, $R_2$ and $R_2'$ each represents an aliphatic group, an aromatic group, a heterocyclic group, an acyl group, a sulfonyl group, an aliphatic or aromatic oxy group, an amino group or the like. When a hydroxyl group is present at the o- or p-position with respect to the nitrogen atom of the pyridine ring or the heterocyclic ring respectively, the hydroxyl group can also form a cyclic ketone through, for instance, the following tautomerism.

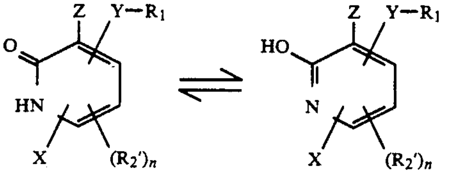

-continued

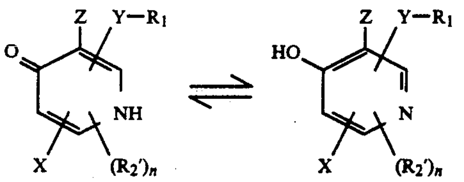

When X in Formulae (I) and (II) represents an elimination group, it includes for instance, a group which bonds the coupling active carbon atom with an aliphatic, aromatic or heterocyclic group, or with an aliphatic, aromatic or heterocyclic sulfonyl group, or an aliphatic, aromatic or heterocyclic carboxyl group through an oxygen, nitrogen, sulfur or carbon atom, or it is a halogen atom or an aromatic azo group. The aliphatic, aromatic or heterocyclic group in the elimination group may be substituted with substituents such as those listed above in connection with $R_1$. When it has two or more substituents, they may be the same or different. In addition, these substituents may have a substituent such as those acceptable for $R_1$.

The elimination groups include, for instance, halogen atoms such as fluorine, chlorine and bromine atoms, alkoxy groups such as ethoxy, dodecyloxy, methoxyethylcarbamoylmethoxy, carboxypropyloxy and methylsulfonylethoxy groups, aryloxy groups such as 4-chlorophenoxy, 4-methoxyphenoxy and 4-carboxyphenoxy groups, acyloxy groups such as acetoxy, tetradecanoyloxy and benzoyloxy groups, aliphatic or aromatic sulfonyloxy groups such as methanesulfonyloxy and toluenesulfonyloxy groups, acylamino groups such as dichloroacetylamino and heptafluorobutyrylamino groups, aliphatic or aromatic sulfonamido groups such as methanesulfonamido and p-toluenesulfonylamido groups, alkoxycarbonyloxy groups such as ethoxycarbonyloxy and benzyloxycarbonyloxy groups, aryloxycarbonyloxy groups such as phenoxycarbonyloxy group, aliphatic, aromatic or heterocyclic thio groups such as ethylthio, phenylthio and tetrazolylthio groups, carbamoylamino groups such as N-methylcarbamoylamino and N-phenylcarbamoylamino groups, 5- or 6-membered nitrogen atom-containing heterocyclic groups such as imidazolyl, pyrazolyl, triazolyl and 1,2-dihydro2-oxo-1-pyridyl groups, imido groups such as succinimido and hydantoinyl groups and aromatic azo groups such as phenylazo group. These groups may be substituted with the groups acceptable as the substituents for $R_1$. The elimination groups bonded through a carbon atom include bis-type couplers formed through condensation of 4-equivalent couplers with an aldehyde or ketone. The elimination groups effectively used in the present invention may contain a photographically useful group such as that useful for inhibiting or accelerating the development.

Y in Formulae (I) and (II) is a divalent bonding group having at least one amido or ester bond. They include, for instance, the following groups: $-N(R_3)-CO-$, $-N(R_3)-SO_2-$, $-N(R_3)-CO-N(R_4)-$, $-N(R_3)-SO_2-N(R_4)-$, $-N(R_3)-COO-$, $-N(R_3)-SO_2O-$, $-CO-N(R_4)-$ and $-SO_2-N(R_4)-$, wherein $R_3$ and $R_4$ each represents a hydrogen atom, an aliphatic group, an aromatic group or a heterocyclic group.

It is preferred that the nitrogen atom of the pyridine ring in Formula (I) or the heterocyclic ring in Formula (II) has no substituent. Y in Formulae (I) and (II) is preferably— $N(R_3)$—CO— or or —CO—$N(R_4)$— and more preferably —NHCO— which is bonded with the pyridine ring in Formula (I) or the heterocyclic ring in Formula (II) through the nitrogen atom.

X in Formulae (I) and (II) is preferably a hydrogen atom, a halogen atom, an aliphatic or aromatic oxy group, an aliphatic or aromatic thio group, an aliphatic or aromatic oxycarbonyloxy group, an aliphatic or aromatic acyloxy group or an aliphatic or aromatic sulfonyloxy group.

When $R_1$ and $R_2$ (or $R_2'$) or $R_2$s (or $R_2'$s) in Formulae (I) and (II) form a ring, the ring is preferably a 5- to 7-membered one, more preferably a 5- or 6-membered one. The ring may comprise an N or O atom in addition to carbon atoms and it may be aromatic or non-aromatic.

Z represents a dissociative group having an acid dissociation constant pKa ranging from 5 to 12 such as a hydroxyl group, a sulfonamido group which may be substituted with an aliphatic, aromatic or heterocyclic group or an active methine group having at least one, preferably 2 electron-attractive groups such as an acyl group and a cyano group.

Z is preferably a hydroxyl group or an aromatic sulfonamido group. Among them, particularly preferred is a hydroxyl group.

The group: —Y—$R_1$ is arranged at the 2 position or 5-position with respect to the nitrogen atom of the pyridine ring or the heterocyclic ring. The couplers used in the present invention in which the group: —Y—$R_1$ is arranged at the 2-position of the ring is particularly preferred, since the absorption spectra of the azomethine dye derived from this coupler are sharp and thus a high molecular extinction coefficient can be obtained.

The coupler represented by Formulae (I) and (II) has preferably a so-called ballast group having 8 or more carbon atoms in at least one of $R_1$, $R_2$ (or $R_2'$), X and Z, whereby the group can stably be introduced into the color photographic light-sensitive material.

At least one of $R_1$, $R_2$ (or $R_2'$) and X in Formulae (I) and (II) for the coupler used in the present invention may have one or more pyridyl groups of Formula (I) or heterocyclic groups of Formula (II) from which $R_1$, $R_2$ (or $R_2'$) or X has been removed. Namely, at least one of $R_1$, $R_2$ (or $R_2'$) and X of the couplers used in the invention has a pyridyl group represented by the following general formula:

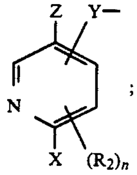 ; 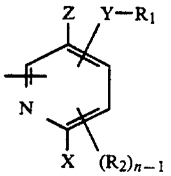 or 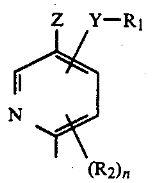

or a heterocyclic group represented by the following general formula:

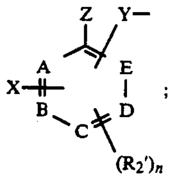 ; 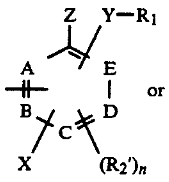 or 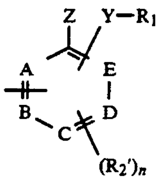

to form an oligomer or a polymer.

Among the couplers used in the present invention, those represented by Formulae (I) and (II) having one pyridyl group or one heterocyclic group from which $R_1$, $R_2$ (or $R_2'$) or X has been removed will be referred to as dimers and those having two such pyridyl or heterocyclic groups will be referred to as trimers. The polymers include, for instance, vinyl polymers having at least one of the three pyridyl or heterocyclic groups in $R_1$, $R_2$ (or $R_2'$) or X. The average degree of polymerization of these polymers is, for instance, about 10 to 1,000.

In the couplers represented by the general formula (II), the number of nitrogen atoms represented by A to E is represented by Formula (II) are, for instance, those represented by the following general formulae:

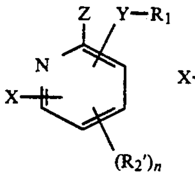 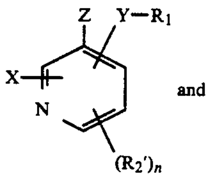 and 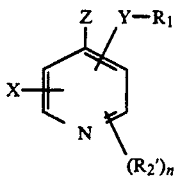

more preferably those represented by the following general formulae:

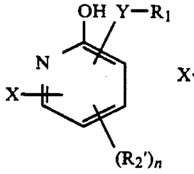 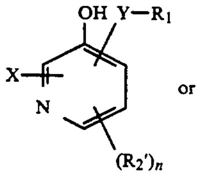 or 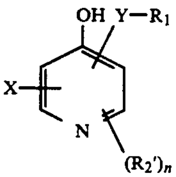

and in particular those having the following general formula (III):

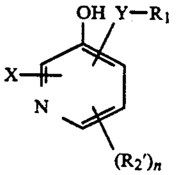

Among the couplers represented by formula (III), the group: —Y—$R_1$ is preferably present at the 2- or 5-position with respect to the nitrogen atom of the pyridine ring and more preferably at the 2-position.

Specific examples of the couplers used in the present invention are listed below, but the present invention is not restricted to these specific examples.

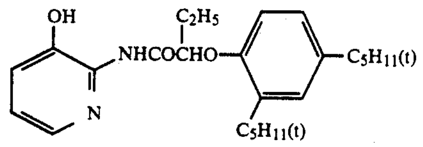
(1)
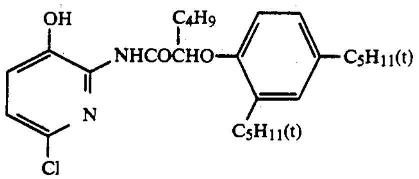
(2)
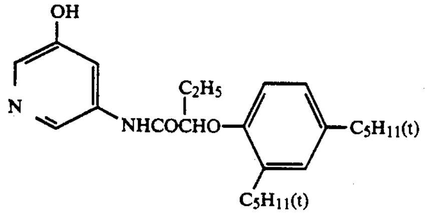
(3)
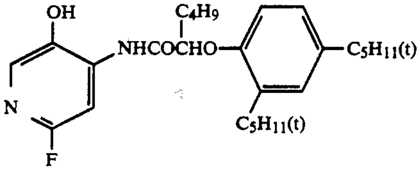
(4)
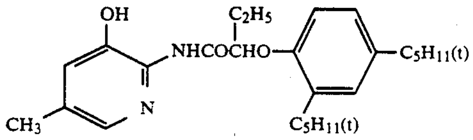
(5)
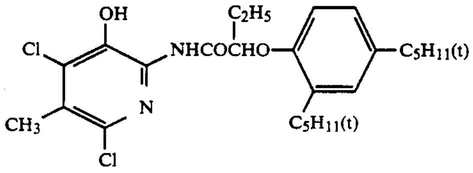
(6)
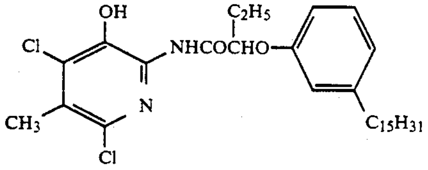
(7)
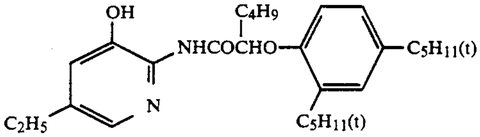
(8)
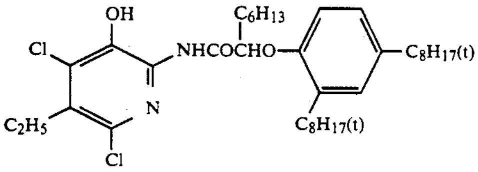
(9)
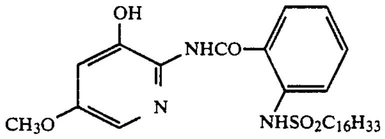
(10)
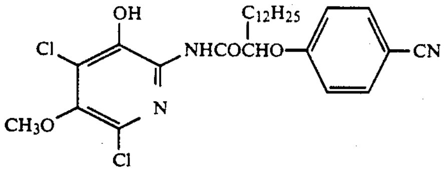
(11)
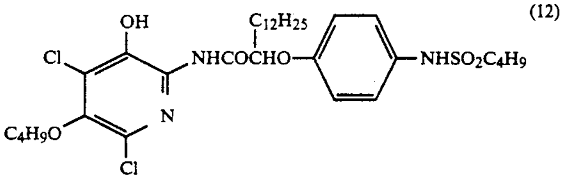
(12)
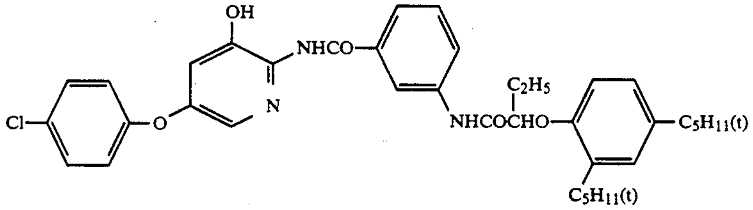
(13)
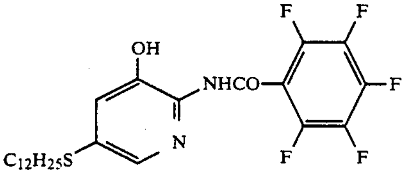
(14)

-continued
(15)
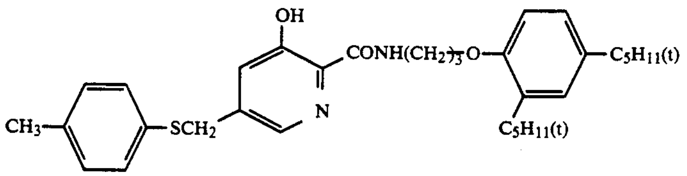
(16)
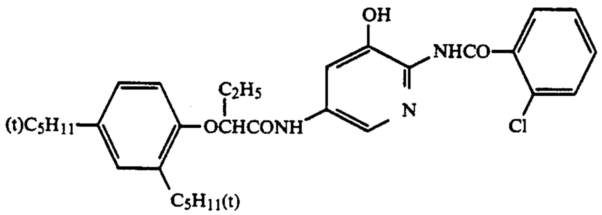
(17)
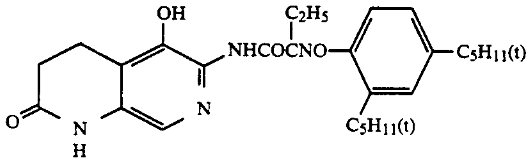
(18)
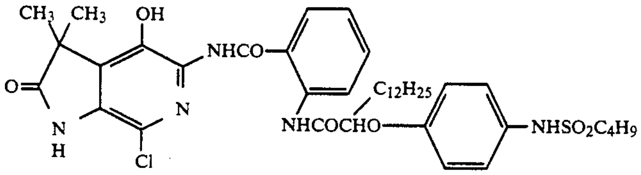
(19)
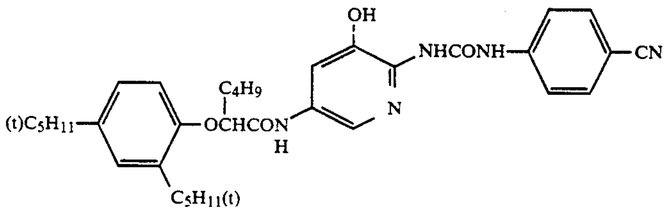
(20)
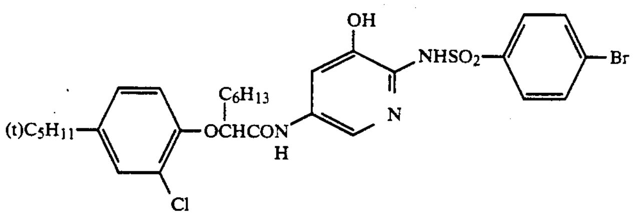
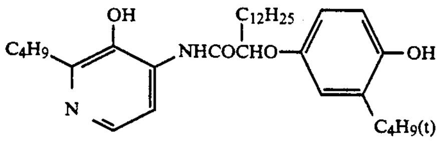
(21)
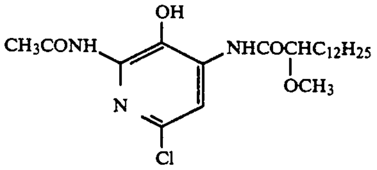
(22)
(23)
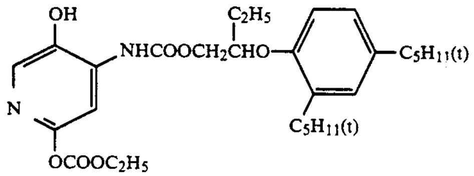

-continued
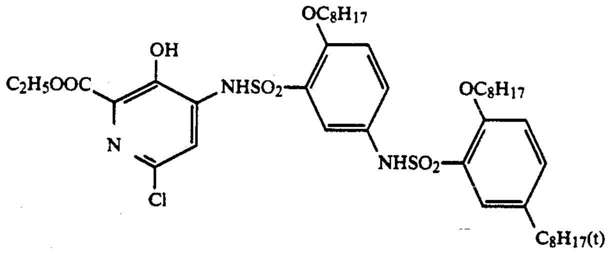
(24)
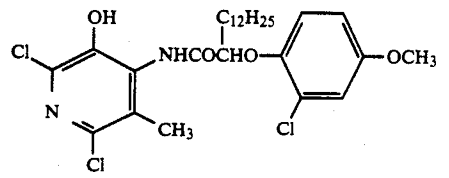
(25)
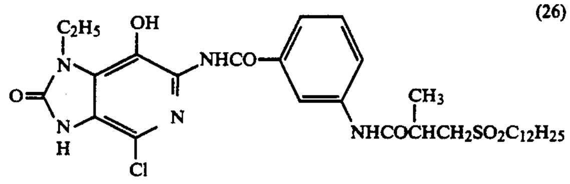
(26)
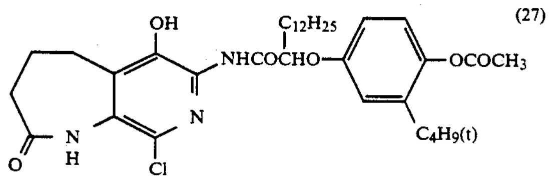
(27)
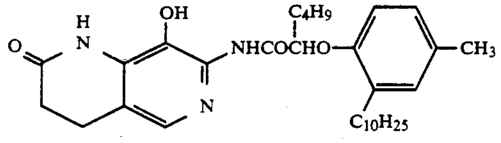
(28)
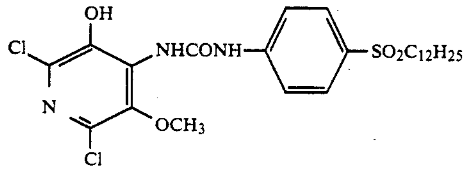
(29)
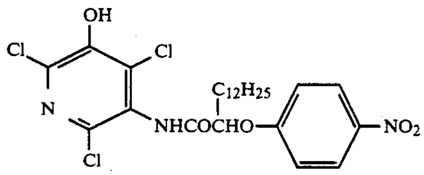
(30)
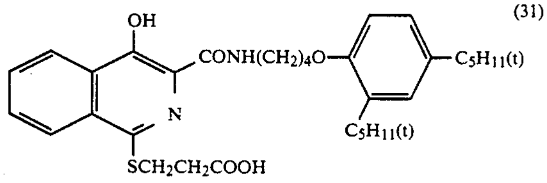
(31)
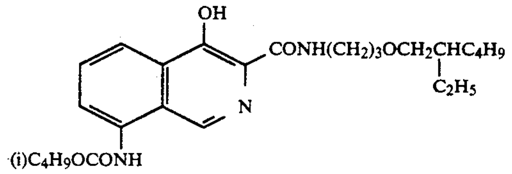
(32)
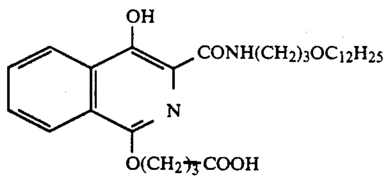
(33)
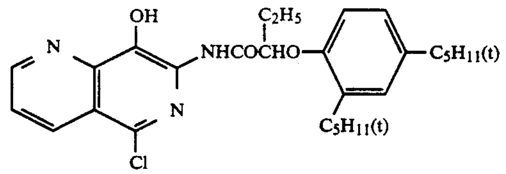
(34)
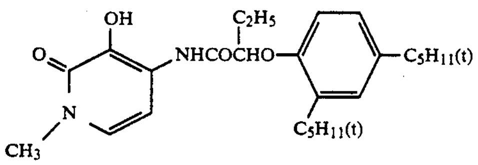
(35)
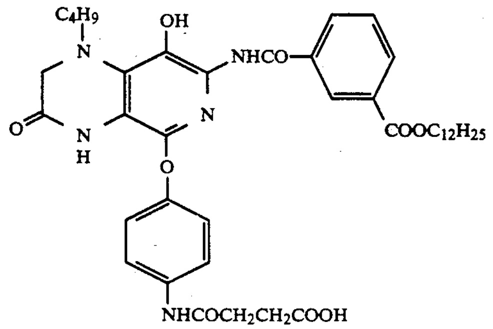
(36)

-continued
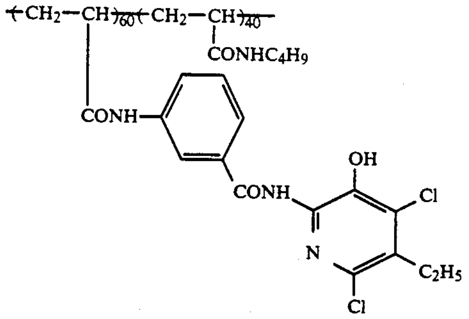
(37)
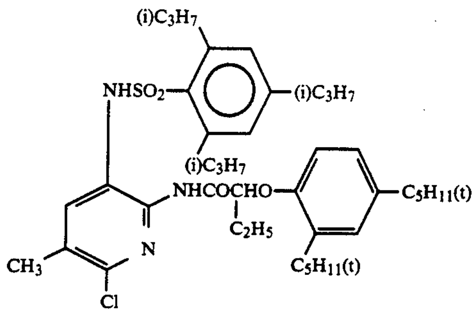
(38)
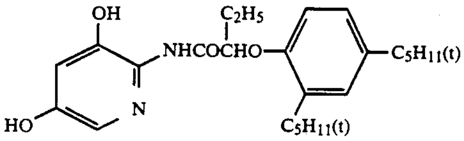
(39)
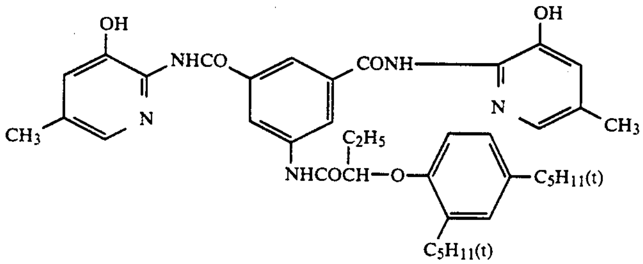
(40)
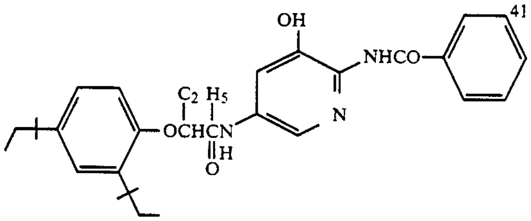
41
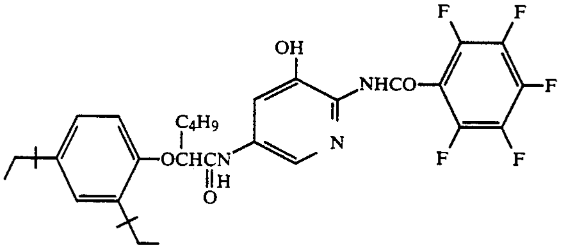
42
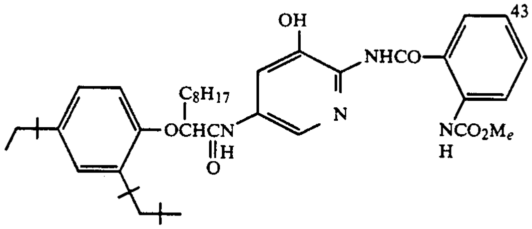
43
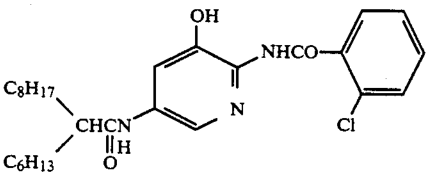
44
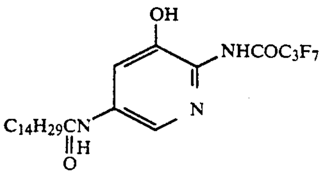
45
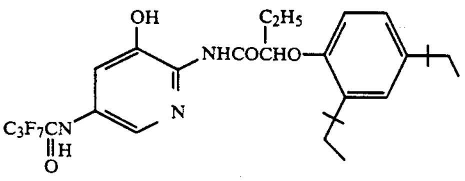
46

-continued
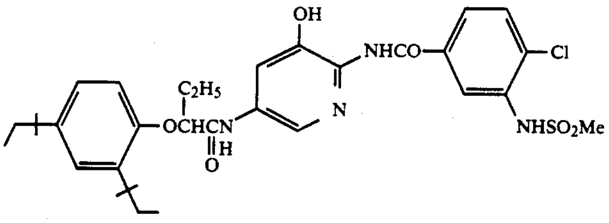
47
48
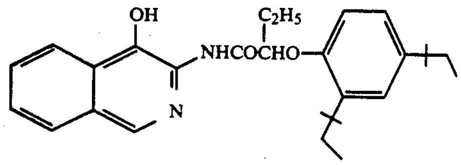
49
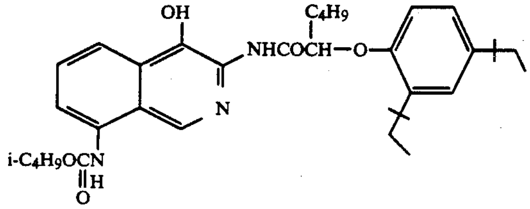
50
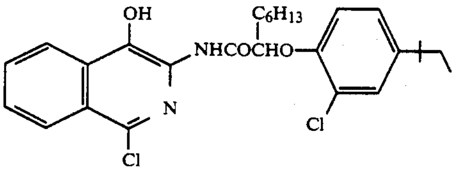
51
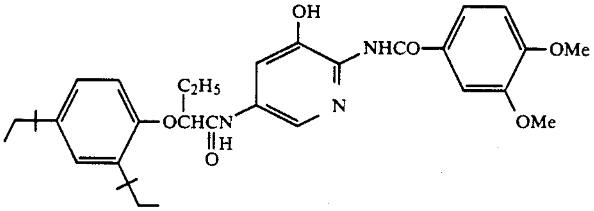
52
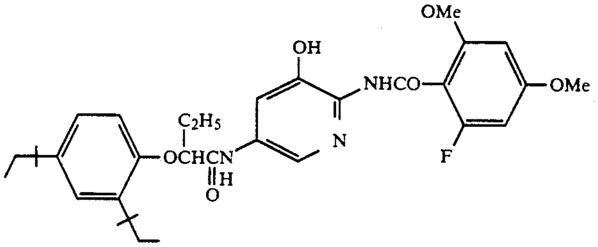
53
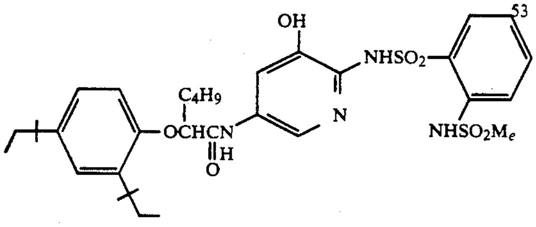
54
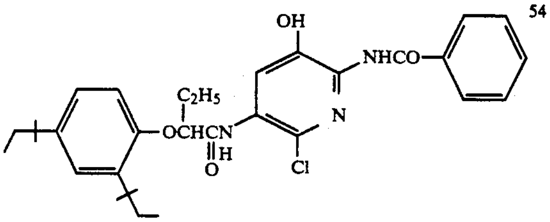
55
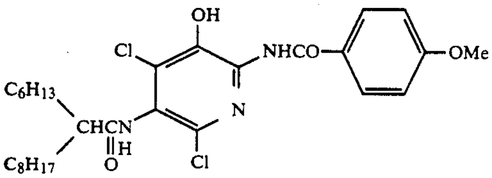
56
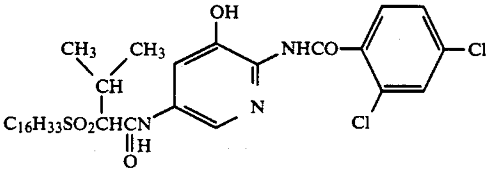

-continued
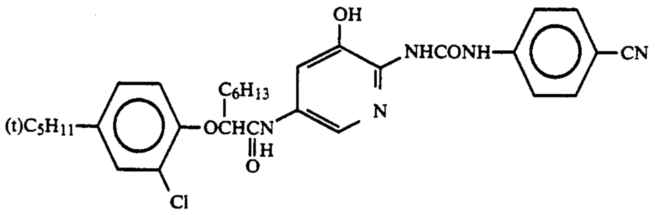
(57)
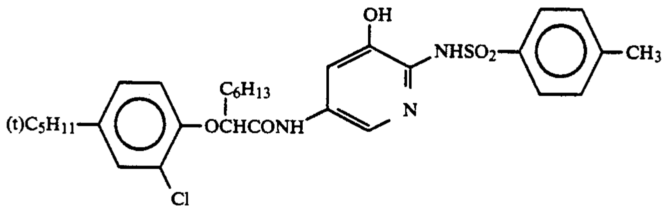
(58)
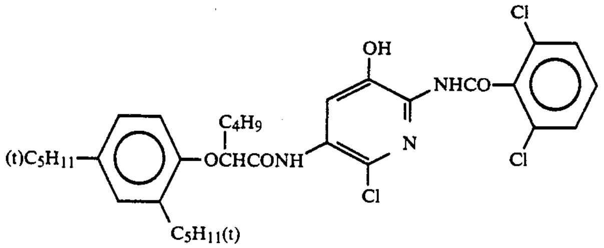
(59)
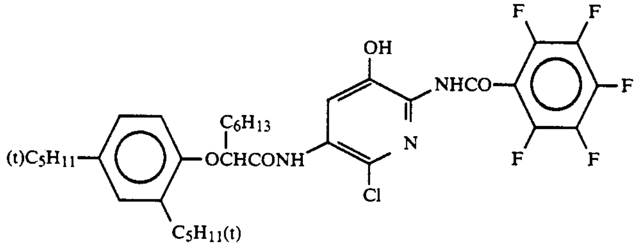
(60)
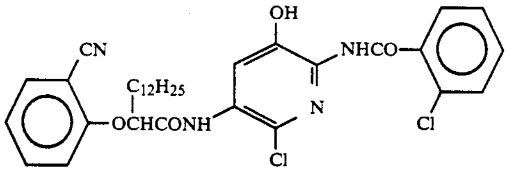
(61)
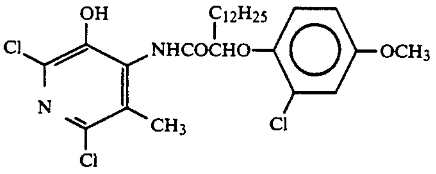
(62)
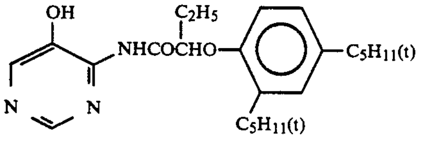
(63)
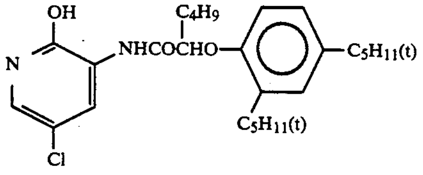
(64)
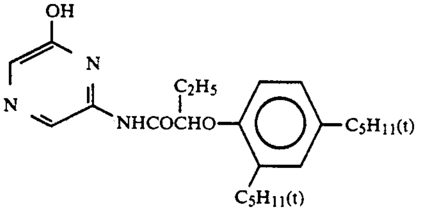
(65)
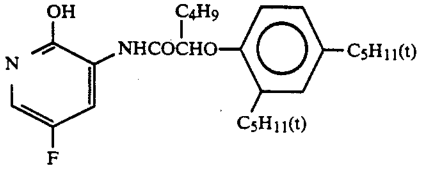
(66)

-continued
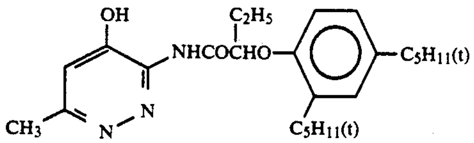
(67)
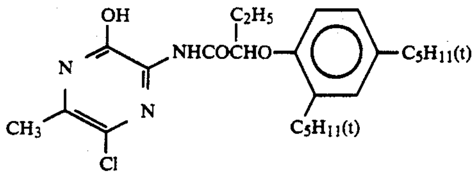
(68)
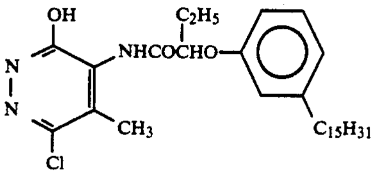
(69)
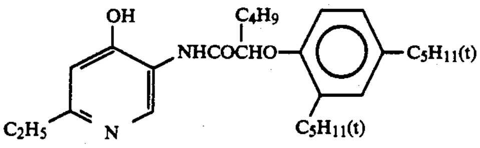
(70)
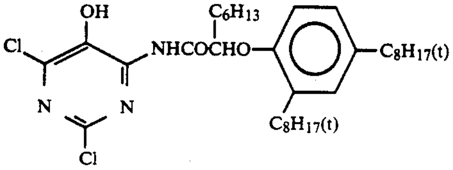
(71)
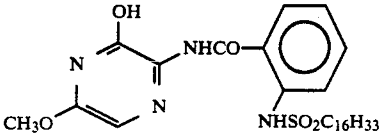
(72)
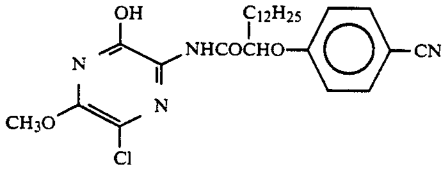
(73)
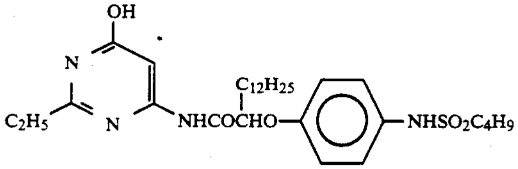
(74)
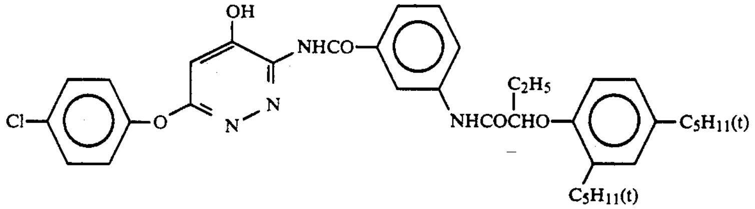
(75)
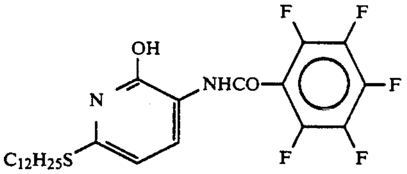
(76)
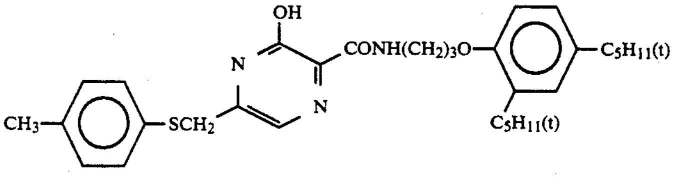
(78)
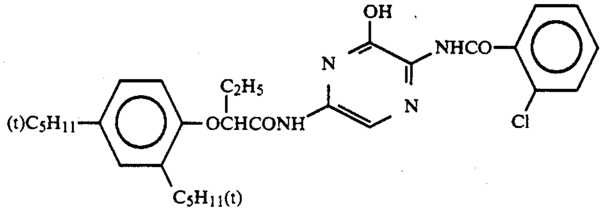
(79)

-continued
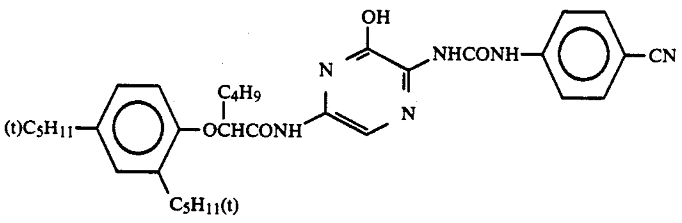
(80)
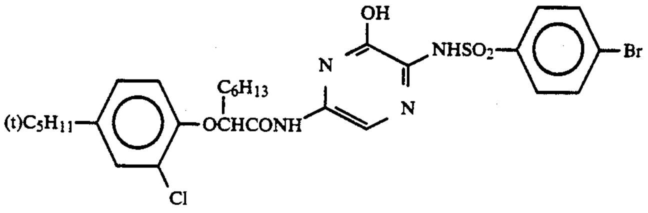
(81)
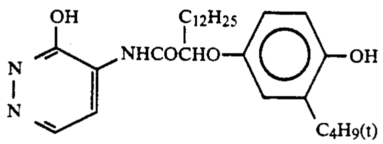
(82)
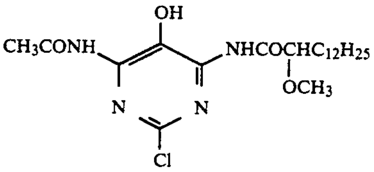
(83)
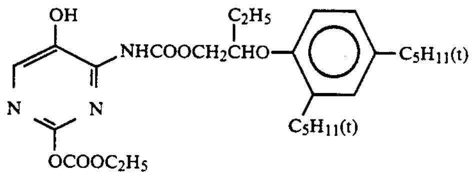
(84)
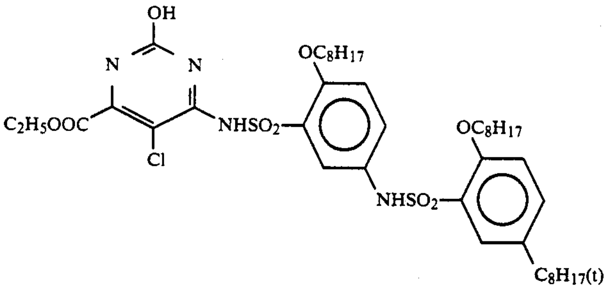
(85)
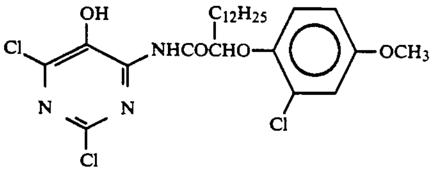
(86)
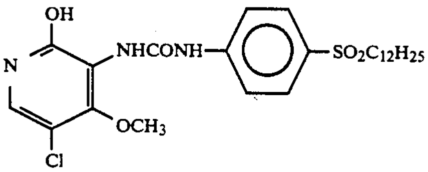
(87)
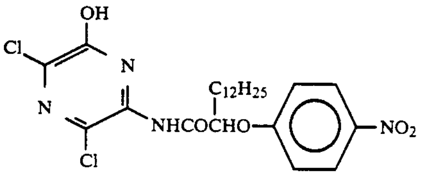
(88)
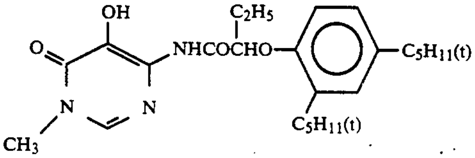
(89)

-continued

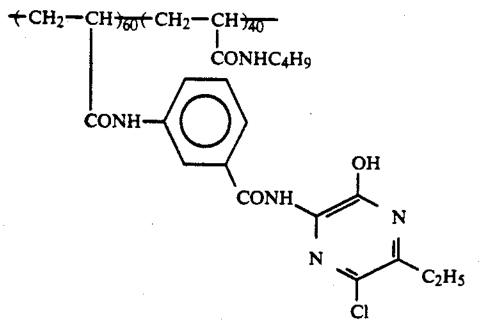

(90)

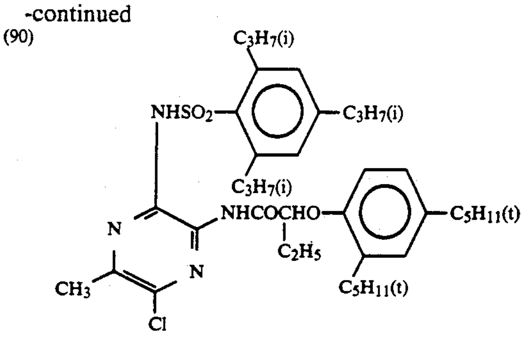

(91)

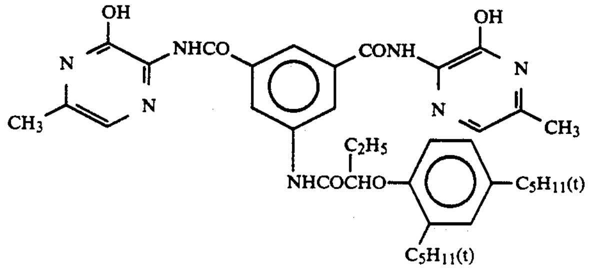

(92)

Methods for preparing the couplers used in the present invention will now be explained in detail below.

The couplers used in the invention can be prepared according to, for instance, a process shown in the following reaction scheme:

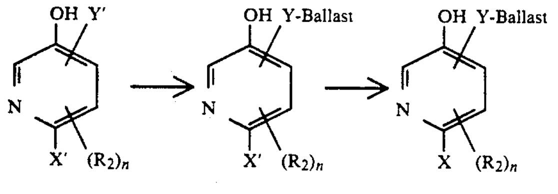

or

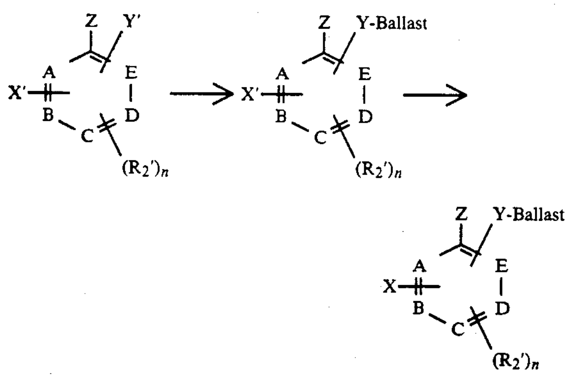

wherein Y' represents an amino group or a carboxyl group, $R_2$ (or $R_2'$) and n are the same as those defined above and X' represents a hydrogen atom or a halogen atom.

When Y' is an amino group, the compound is reacted with an acid chloride, and, on the contrary, when Y' is a carboxyl group, the compound is reacted with an amine to form a bond through a known dehydration-condensation process and a ballast group is introduced therein. Alternatively, an elimination group (X) may be introduced therein before or preferably after the introduction of the ballast group.

The 3-hydroxypyridine derivatives used as the starting compound can be produced by a process described in Beilstein's Handbuch der Organischen Chemie or literatures referred to therein.

The processes used for producing the couplers used in the Present invention will be illustrated in the following preparation Examples.

PREPARATION EXAMPLE 1 (PREPARATION OF EXEMPLIFIED COUPLER (1))

11.0 g of 2-amino-3-hydroxypyridine was dissolved in 100 mλ of acetonitrile and 20 mλ of dimethylacetamide. 38.9 g of 2-(2',4 -di-t-amylphenoxy)butyric chloride was dropwise added to the solution under reflux with heating for additional 2 hours and then cooled. The reaction mixture was dissolved in 250mλ of ethyl acetate. 250 mλ of water was added to the solution. The solution was neutralized and then separated into phases. The ethyl acetate phase was further washed with water and then the solvent was distilled off under a reduced pressure. 200 mλ of acetonitrile was added to the residue to obtain a solution, which was cooled to form crystals. The crystals were recovered by filtration to give 35.1 g of Coupler (1). Melting point (m.p.): 80°-83° C.

Elemental Analysis:

Found: C,72.59%; H,8.69%; N,6.72%;

Calculated: C,72.78%; H,8.80%; N,6.79%.

PREPARATION EXAMPLE 2 (PREPARATION OF EXEMPLIFIED COUPLER (2))

2-(2'(2", 4"-di-t-amylphenoxy)-hexanoic amido)-3-hydroxypyridine was obtained in the same manner used in Preparation Example 1 except that an equimolar amount of 2-(2', 4'-di t amylphenoxy)hexanoic chloride was substituted for 2(2',4'-di-t-amylphenoxy)butyric chloride used in Preparation Example 1.

25 g of 2-(2'-(2", 4"-di-t-amylphenoxy)-hexanoic amido)-3-hydroxypyridine obtained above was dissolved in 200 mλ of methylene chloride. 8.4 g of sulfuryl chloride was dropwise added thereto at room temperature with stirring. 20 minutes after the completion of the dropwise addition, the liquid reaction mixture was poured into water. After extraction with methylene chloride followed by concentration of the extract, the residue was purified by silica gel column chromatography to thus obtain 18 g of Coupler (2) as an oily substance.

PREPARATION EXAMPLE 3 (PREPARATION OF EXEMPLIFIED COUPLER (3))

(i) Preparation of 3-(2'-(2", 5"-di-t-amylphenoxy)butanoic amido)-5-methoxypyridine 10 g of 3-amino-5-methoxypyridine was dissolved in 30 mλ of dimethylacetamide and 13.5 mλ of triethylamine. 27.3 g of 2-(2,5-di t-amylphenoxy)butanoic chloride was dropwise added to the solution with stirring. After conducting the reaction for 20 minutes, the reaction solution was poured into water and then extracted with ethyl acetate. After drying the extract over anhydrous sodium sulfate followed by concentration and purification by silica gel column chromatography, 15 g of 3-(2'-(2", 5"-di-t-amylphenoxy)butanoic amido)-5-methoxypyridine was obtained as an oily substance.

(ii) Preparation of Coupler (3)

9 g of 3-(2'-(2", 5"-di-t-amylphenoxy)butanoic amido)-5-methoxypyridine obtained above and 3 g of methylmercaptan were dissolved in DMF. 2.1 g of 60% sodium hydride was slowly added to the solution with stirring while cooling with ice. After completion of the addition, the mixture was stirred at 80° C. for 2 hours and the liquid reaction mixture was poured into water. The mixture was acidified with acetic acid and then subjected to extraction with ethyl acetate. The resulting organic phase was dried over anhydrous sodium sulfate and then concentrated. The resulting residue was purified by silica gel column chromatography to obtain 4.2 g of the intended compound (Coupler (3)) in the form of a white powder.

PREPARATION EXAMPLE 4 (PREPARATION OF EXEMPLIFIED COUPLER (5))

25.5 g of 6-amino-3 picoline was dissolved in 100 mλ of acetonitrile. 30.5 g of pivalic chloride was dropwise added to the solution at room temperature. After completion of the dropwise addition, the mixture was heated under reflux for 30 minutes and then cooled. It was poured into 100 mλ of water and the pH value thereof was adjusted to 8 with the addition of sodium carbonate. After extraction with chloroform, the solvent was distilled off under a reduced pressure to give 44.7 g of crystalline 6-pivaloylamino 3-picoline. This compound was suspended in 500 mλ of chloroform and then 44 g of m-chloroperbenzoic acid was added in portions thereto. After completion of the addition, the mixture was stirred for 2 hours and then allowed to stand overnight. It was concentrated under a reduced pressure and then dissolved in ethyl acetate. The solution was washed with an aqueous sodium carbonate solution. The solvent was distilled off under a reduced pressure to obtain 44.5 g of solid 6-pivaloylamino-3-picoline oxide. It was dissolved in 200 mλ of chloroform. 54 mλ of acetic anhydride was added to the solution. 43 g of bromine diluted with 100 mλ of chloroform was dropwise added thereto under cooling with ice. After completion of the addition, the mixture was allowed to stand at room temperature for 30 minutes. 23 g of sodium acetate was added thereto and the mixture was heated under reflux for 3 hours. A small amount of water was added thereto. After neutralization with sodium carbonate, the chloroform phase was recovered and concentrated under a reduced pressure. The residue was taken by silica gel column chromatography (solvent: 5% methanol, chloroform) to obtain 28 g of 5 bromo-6-pivaloylamino-3-picoline oxide. It was dissolved in 80 mλ of methanol. 0.15 mole of sodium methoxide was added to the solution and the mixture was heated under reflux for 40 hours. After cooling followed by neutralization with oxalic acid and concentration, the product was dissolved in chloroform and insoluble matters were removed by filtration. The solvent was distilled off under a reduced pressure to obtain 26 g of 5-methoxy-6-pivaloylamino-3-picoline oxide. This product was added to 200 mλ of methanol and 50 mλ of 6N hydrochloric acid and the mixture was heated under reflux for 52 hours. After neutralization of the hydrochloric acid followed by extraction with chloroform, the solvent was distilled off under reduced Pressure. 200 mλ of acetonitrile was added thereto and 33.8 g of 2-(2', 4'-di-t-amylphenoxy)butyric chloride was dropwise added thereto under reflux with heating. The mixture was cooled and the resulting crystals were collected by filtration to obtain 35.4 g of 5-methoxy-6-(2-(2', 4'-di-t-amylphenoxy)butyroylamino) -3 picoline oxide. It was dissolved in 500 mλ of chloroform. 55 g of phosphorus trichloride was added to the solution at room temperature. The mixture was heated under reflux for one hour. After cooling, the mixture was poured into 500 g of ice. pH of the mixture was adjusted to 10 with the addition of aqueous ammonia. After extraction with ethyl acetate, the solvent was distilled off under a reduced pressure to give 31.8 g of 5-methoxy-6-(2-(2', 4'-di-t-amylphenoxy) butyroylamino)-3-picoline. It was dissolved in 200 mλ of chloroform. 22.5 g of boron tribromide was dropwise added thereto under cooling with ice. Then the temperature was slowly elevated to room temperature and the stirring was continued at room temperature for 2 hours. The reaction mixture was poured into ice/water and then neutralized with sodium carbonate. After extraction with chloroform, the solvent was distilled off under a reduced pressure. The residue was taken by silica gel column chromatography (solvent: chloroform). After recrystallization from ethyl acetate/acetonitrile, 22.6 g of Coupler (5) was obtained. m.p.: 91°–95° C.

Elementary Analysis:

Found: C,73.13%; H,8.79%; N,6.62%l

Calculated: C,73.20%; H,8.98%; N,6.57%.

PREPARATION EXAMPLE 5 (PREPARATION OF EXEMPLIFIED COUPLER (6))

19.6 g of 5-hydroxy-6-(2-(2', 4'-di-t-amylphenoxy) hexanoylamino)-3-picoline was formed in the same manner as that used in Preparation Example 4 except that 2-(2', 4'-di-t-amylphenoxy)butyric chloride was replaced with an equimolar amount of 2-(2', 4'-di t amylphenoxy)hexanoic chloride. This compound was dissolved in 80 mλ of methylene chloride. 12.4 g of sulfuryl chloride was dropwise added thereto at room temperature and the mixture was stirred for one hour. After completion of the stirring, the liquid reaction mixture was poured into water. After extraction with methylene chloride followed by concentration, the resulting residue was purified by silica gel column chromatography to give 14.1 g of Coupler (6).

PREPARATION EXAMPLE 6 (PREPARATION OF EXEMPLIFIED COUPLER (7))

Coupler (7) was prepared in the same manner as that used in Preparation Example 5 except that 2-(2', 4'-di t-amylphenoxy) hexanoic chloride was replaced with an equimolar amount of 2-(3-n-pentadecylphenoxy)butyric chloride.

PREPARATION EXAMPLE 7 (PREPARATION OF EXEMPLIFIED COUPLER (8))

Coupler (8) was prepared in the same manner as that used in Preparation Example 4 except that 6-amino-3-picoline wa replaced with an equimolar amount of 6-amino-3-ethylpyridine and that 2-(2', 4'-di-t-amylphenoxy)butyric chloride was replaced with an equimolar amount of 2-(2', 4'-di-t-amylphenoxy)hexanoic chloride.

PREPARATION EXAMPLE 8 (PREPARATION OF EXEMPLIFIED COUPLER (9))

5-Ethyl-3-hydroxy-2-(2-(2', 4'-di-t-octylphenoxy) octanoylamino)pyridine was prepared in the same manner as that used in Preparation Example 7 except that 2 (2', 4'-di-t-amylphenoxy)hexanoic chloride was replaced with an equimolar amount of 2-(2', 4'-di-t-octylphenoxy)octanoic chloride. It was then chlorinated with sulfuryl chloride in methylene chloride to give Coupler (9).

PREPARATION EXAMPLE 9 (COUPLER (16))

12.0 g of Coupler (3) prepared in Preparation Example 3 was dissolved in 40 mλ of acetic acid and 15 mλ of acetic anhydride. 2.3 mλ of concentrated nitric acid was dropwise added to the solution under cooling with water. The mixture was stirred at room temperature for additional 6 hours. It was poured into ice/water and neutralized with sodium carbonate. After extraction with ethyl acetate, the solvent was distilled off under a reduced pressure. The resulting residue was dissolved in 100 mλ of ethanol. 50 mλ of water was added to the solution and then 10 g of sodium hydrosulfite was added, in portions, to the solution under heating with reflux. After conducting the reflux till the yellow color of the reaction mixture substantially disappeared, it was cooled. Water was added to the reaction mixture and the crystals thus formed were taken by filtration. The crystals were dissolved in 30 mλ of dimethylacetamide and 100 mλ of acetonitrile. 5.3 g of o-chlorobenzoyl chloride was dropwise added thereto at 60° C. The mixture was refluxed for 6 hours, then cooled and neutralized with an aqueous sodium hydroxide solution. The crystals thus formed were taken by filtration and recrystallized from acetonitrile to give 9.8 g of Coupler (16). m.p.: 125°-128° C.

Elementary Analysis:

Found: C,67.71%; H,7.03%; N,7.60%;

Calculated: C,67 89%; H,7.12%; N,7.42%.

PREPARATION EXAMPLE 10 (COUPLER (17))

16.4 g of 5-hydroxy-1,2,3,4-tetrahydro-1,7-naphthylidin-2-one was dispersed in 50 mλ of acetic acid and 20 mλ of acetic anhydride. 7.9 mλ of concentrated nitric acid was dropwise added to the dispersion under cooling with water and the mixture was stirred at room temperature for 3 hours. The reaction mixture was poured in ice/water and neutralized with sodium carbonate. After extraction with ethyl acetate, the solvent was distilled off under a reduced pressure. The resulting residue was dissolved in 300 mλ of ethanol. 150 mλ of an aqueous solution of sodium hydrosulfite was slowly added thereto and the mixture was heated under reflux for 30 minutes. After cooling to room temperature, the mixture was poured in 450 mλ of water. The crystals thus formed were taken by filtration and dissolved in 50 mλ of dimethylacetamide and 150mλ of acetonitrile. 31.1 g of 2-(2,4-di-t-amylphenoxy)butyric chloride was dropwise added to the solution with heating under reflux. After completion of the addition, the mixture was refluxed for additional 3 hours. The mixture was cooled to room temperature. 300 mλ of ethyl acetate and 300 mλ of water were added thereto. After the neutralization, the mixture was separated into phases. The ethyl acetate phase was further washed with water and dried over Glauber's salt. The solvent was distilled off under a reduced pressure. The residue was purified by silica gel column chromatography (chloroform/ethyl acetate=5/1) and then recrystallized from a solvent mixture of hexane and ethyl acetate to give 26.4 g of intended Coupler (17).

PREPARATION EXAMPLE 11 (COUPLER (19))

3-(2'-(2'', 4''-di-t-amylphenoxy)hexanoylamino)-5-hydroxypyridine was prepared in the same manner as that used for producing Coupler (3) except that 2-(2', 4'-di-t-amylphenoxy) butanoic chloride used in Preparation Example 3 was replaced with an equimolar amount of 2-(2', 4'-di-t-amylphenoxy)hexanoic chloride. 12.0 g of the product was dissolved in 40 mλ of acetic acid and 15 mλ of acetic anhydride. 2.2 mλ of concentrated nitric acid was dropwise added to the solution under cooling with water. The mixture was stirred at room temperature for 6 hours, then poured into ice/water and neutralized with sodium carbonate. After extraction with ethyl acetate, the solvent was distilled off under a reduced pressure. The residue was dissolved in 100 mλ of ethanol and 50 mλ of water was added thereto. 10 g of sodium hydrosulfite was added in portions thereto with heating under reflux. After performing reflux till the yellow color of the reaction mixture substantially disappeared, it was cooled. The crystals thus formed were taken by filtration. 9.8 g of the crystals were dispersed in 80 mλ of toluene. 3.2 g of p-cyanophenyl isocyanate was added to the dispersion and the mixture was stirred at 80° C. for 3 hours. The reaction mixture was poured into water. After extraction with ethyl acetate, the solvent was distilled off under a reduced pressure. The resulting residue was purified by silica gel column chromatography to give 8.3 g of Coupler (19).

PREPARATION EXAMPLE 12 (COUPLER (20))

3 _(2'-(2''-chloro-4''-t-amylphenoxy)hexanoylamino)-5-hydroxypyridine was prepared in the same manner as that used for the production of Coupler (3) except that 2-(2', 4'-di-t-amylphenoxy)butanoic chloride used in Preparation Example 3 was replaced with an equimolar amount of 2-(2'-chloro-4'-t-amylphenoxy)hexanoic chloride. 12 g of the product was dissolved in 40 mλ of acetic acid and 15 mλ of acetic anhydride. 2.2 mλ of concentrated nitric acid was dropwise added to the solution under cooling with water. The mixture was stirred at room temperature for 6 hours, poured into ice/water and neutralized with sodium carbonate. After extraction with ethyl acetate, the solvent was distilled off under a reduced pressure. The resulting residue was dissolved in 100 mλ of ethanol. 50 mλ of water was added thereto. 12 g of sodium hydrosulfite was added thereto in portions with heating under reflux. After conducting the reflux till the yellow color of the reaction mixture substantially disappeared, it was cooled. The crystals thus formed were taken by filtration. 8 g of the crystals were dissolved in 30 mλ Of acetonitrile. 1.7 mλ of pyridine was added to the solution. A solution of 4.6 g of p-bromobenzenesulfonyl chloride in 10 mλ of acetonitrile wa dropwise added thereto with heating under reflux. After completion of the addition, the reaction mixture was refluxed for 3 hours, cooled and poured into water. After extraction with ethyl acetate, the solvent was distilled off and the residue was purified according to silica gel column chromatography to give 6.1 g of Coupler (20).

PREPARATION EXAMPLE 13 (COUPLER (26))

3-Hydroxy-5-phenoxycarbonylaminopyridine was prepared in the same manner as that used for the production of Coupler (3) (Preparation Example 3) except that 2-(2', 4'-di-t-amylphenoxy) butanoic chloride was replaced with an equimolar amount of phenyl chloroformate. 20 g of the product was dissolved in 80 mλ of acetic acid and 20 mλ of acetic anhydride. 5.5 mλ of concentrated nitric acid was dropwise added to the solution under cooling with ice. The mixture was stirred at room temperature for 4 hours, poured into ice/water and neutralized with sodium carbonate. After extraction with ethyl acetate, the solvent was distilled off under a reduced pressure. The residue was dissolved in 100 mλ of ethanol. 100 mλ of water was added to the solution and then 20 g of sodium hydrosulfite was added thereto in small portions under heating and reflux. After conducting the reflux till the yellow color of the reaction mixture substantially disappeared, it was cooled. 100 mλ of water was added thereto and the crystals thus formed were recovered by filtration. 18 g of the crystals were dissolved in 80 mλ of acetonitrile and 40 mλ of dimethylacetamide. 33.6 g of 3-(1'-dodecylsulfonyl 2'-butanoylamino)benzoyl chloride was added to the solution and the mixture was stirred at 50° C. for one hour. After completion of the reaction, the mixture was poured into water. 9 g of sodium acetate was added thereto. After extraction with ethyl acetate, the solvent was distilled off and the residue was dissolved in 200 mλ of methylene chloride. 11 g of sulfuryl chloride was dropwise added to the solution at room temperature and the mixture was stirred for 3 hours. The liquid reaction mixture was poured into water. After extraction with methylene chloride, the solvent was distilled off and the residue was purified by column chromatography to thus give 12.4 g of 2-chloro-6-(1'-dodecylsulfonyl-2'-butanoylamino)-5-hydroxy-3-phenoxycarbonylaminopyridine. 12 g of the product was dissolved in 50 mλ of chloroform. 1.1 mλ of concentrated nitric acid was dropwise added to the solution at room temperature and the mixture was stirred at room temperature for 3 hours. The reaction mixture was poured into water. After extraction with chloroform, the solvent was distilled off. The residue was dissolved in 200 mλ of ethanol. 1 g of Raney nickel and 1.1 g of acetaldehyde were added to the solution and the catalytic hydrogenation reaction was conducted in an autoclave. The catalyst was removed by filtration. The product was poured into water and the crystals thus formed were recovered by filtration. The resulting crude crystals were recrystallized from acetonitrile to obtain 6 g of Coupler (26).

PREPARATION EXAMPLE 14 (COUPLER (41))

Coupler (41) was prepared according to the method shown in the following reaction scheme:

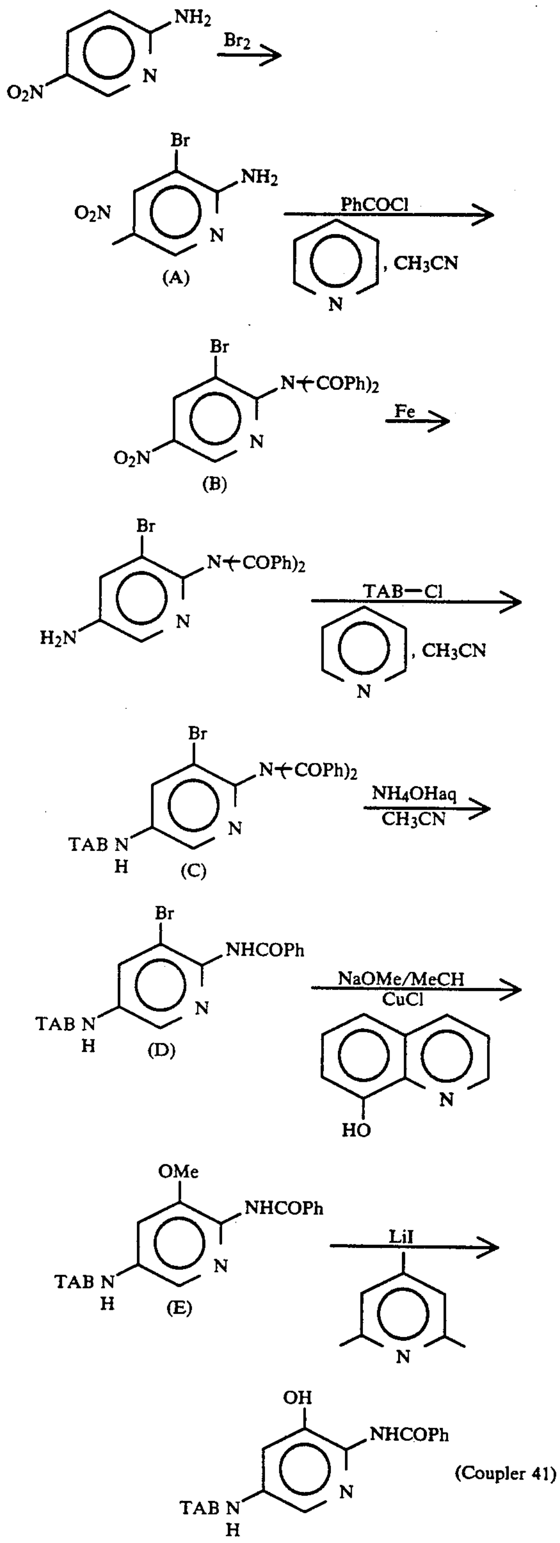

(Coupler 41)

Bromine (62.6 mλ; 1.2 mole) was dropwise added to 2-amino-5-nitropyridine (154.1 g; 1.1 mole) in THF (300 mλ) at room temperature. The resulting mixture was stirred for one hour and then poured into water (3 λ). The crystals thus formed were recrystallized from acetonitrile (500 mλ) to give 2-amino-3-bromo-5-nitropyridine (A) (194.4 g; 80%).

20 mλ of pyridine was added to 2-amino-3-bromo-5-nitropyridine (A) (21.8 g; 0.1 mole) in 300 ,λ of acetonitrile at room temperature in a stream of nitrogen followed by addition of benzoylchloride (24.4 g; 0.2 mole) and agitation for 3 hours. Then dilute hydrochloric acid (0.1N) was added to the resulting mixture. After extraction with ethyl acetate, the resulting ethyl acetate solution was dried over anhydrous sodium sulfate. The solvent was distilled off under a reduced pressure. The residue was recrystallized from methanol to give 3-bromo-2-benzoylamino-5-nitropyridine (B) (28.7 g; 89%).

An isopropyl alcohol (300 mλ) solution containing reduced iron (42.6 g; 0.76 mole), water (42.6 mλ) and ammonium chloride (4.3 g; 81 mole) was refluxed under heating for 10 minutes. Then 3-bromo-2-benzoylamino-5-nitropyridine (B) (42.6 g; 100 mole) was added to the resulting solution and refluxed under heating for 30 minutes. The reaction mixture was filtered through celite and the solvent was distilled off under a reduced pressure. After azeotropic distillation with benzene was performed two times, 2-(2', 4'-di-t-amylphenoxy)butanoyl chloride (33.8 g; 100 mole), acetonitrile (300 mλ) and pyridine (10 mλ) were added to the residue and stirred for one hour Dilute hydrochloric acid (1N) wa added to the resulting mixture. After extraction with ethyl acetate twice, the resulting ethyl acetate phase was dried over anhydrous sodium sulfate. The solvent was distilled off under a reduced pressure. The residue was recrystallized from acetonitrile to give 5-(2-(2', 4'-di-t-amylphenoxy)butanoylamino)-2-dibenzoylamino -3-bromopyridine (C).

28% Aqueous ammonia (20 mλ) was added to an acetonitrile solution (300 mλ) containing the compound (C) obtained above followed by agitation for 15 minutes. The mixture was poured into water and extracted with ethyl acetate twice. The resulting ethyl acetate phase was washed with dilute hydrochloric acid (0. 1N) and an aqueous saturated sodium chloride solution and dried over anhydrous sodium sulfate. The solvent was distilled off under a reduced pressure. The resulting residue was recrystallized from acetonitrile to give 5-(2-(2', 4'-di-t-amylphenoxy)butanoylamino)-2-benzoylamino-3-bromopyridine (D) (19.9 g; 34% on the basis of the compound (B)).

In a stream of nitrogen, 28% sodium methoxide in methanol (7.1 mλ; 36.9 mole), anhydrous cuprous chloride (332 mg; 3.4 mole) and 8-hydroxy quinoline were added to a methanol solution containing compound (D) (19.9 g; 33.5 mole) followed by reflux under heating for 3 hours. Dilute hydrochloric acid was added to the reaction mixture and extracted with ethyl acetate twice. The resulting ethyl acetate phase was washed with an aqueous saturated sodium chloride solution and dried over anhydrous sodium sulfate. The solvent was distilled off and the resulting residue was recrystallized from acetonitrile to give 5-(2-(2', 4'-di-t-amylphenoxy)-butanoylamino)-2-benzoylamino -3-methoxypyridine (E) (10.4 g; 57%).

In a stream of nitrogen, lithium iodide (4.0 g; 29.6 mole) was added to a 2,4,6-collidine solution containing compound (E) (3.9 g; 7.2 mole) followed by reflux under heating for 3 hours. After cooling, dilute hydrochloric acid (0.1N) was added to the reaction mixture. After extraction with ethyl acetate twice, the resulting ethyl acetate phase was washed with an aqueopus saturated sodium chloride solution and dried over anhydrous magnesium sulfate. The solvent was distilled off under a reduced pressure and the residue was recrystallized from acetonitrile to give Coupler (41) (2.9 g; 76%)

Other couplers such as yellow couplers, magenta couplers used in the present invention will now be explained in more detail.

The α-pivaloyl acetoanilide type yellow dye-forming couplers used in the present invention are, for instance, those represented by the following general formula (Y):

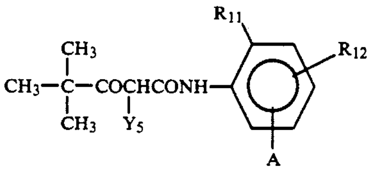
(Y)

in the general formula (Y), $R_{11}$ represents a halogen atom such as F or Cλ, an alkoxy group such as methoxy, ethoxy, methoxyethoxy or benzyloxy group, an aryloxy group such as phenoxy or 4-methoxyphenoxy group or an alkyl group such as methyl, ethyl or trifluoromethyl group; $R_{12}$ represents a hydrogen atom, a halogen atom or an alkoxy group; A represents $-NHCOR_{13}$, $-NH-SO_2-R_{13}$, $-SO_2NHR_{13}$, $-COOR_{13}$ or $-SO_2N(R_{14})R_{13}$ (wherein $R_{13}$ and $R_{14}$ each represents an alkyl group, an aryl group or an acyl group), $-CONR_{13}R_{14}$; $Y_5$ represents an elimination group. $R_{12}$, $R_{13}$ and $R_{14}$ may have substituents and examples of these substituents are the same as those acceptable for $R_1$. The elimination group $Y_5$ is preferably those eliminated at an oxygen or nitrogen atom and in particular those eliminated at the nitrogen atom.

Typical examples of the yellow dye-forming couplers represented by Formula (Y) are as follows:

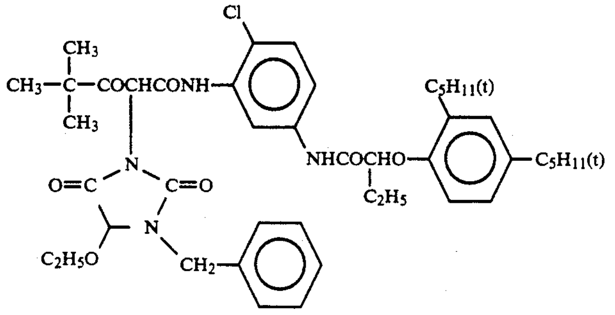
(Y-1)

-continued
(Y-2)
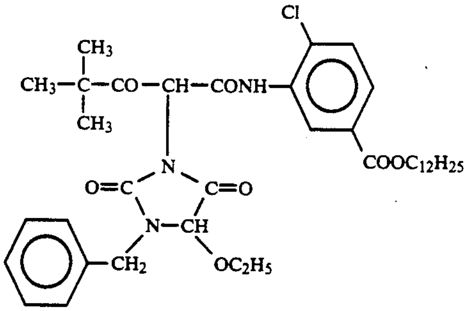
(Y-3)
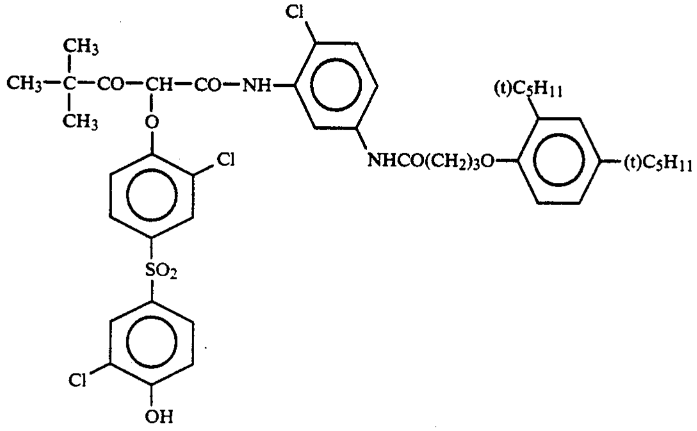
(Y-4)
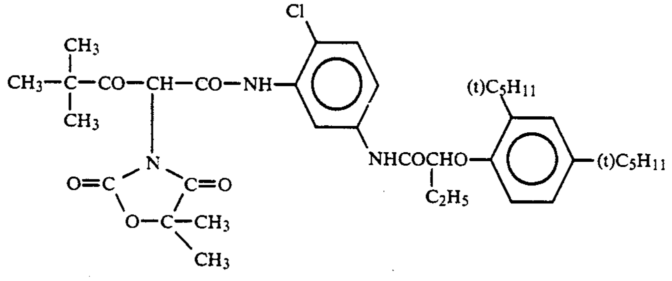
(Y-5)
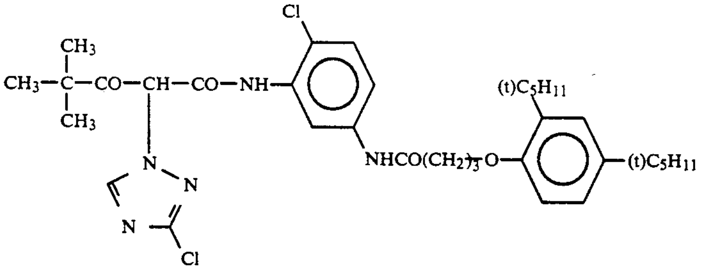
(Y-6)
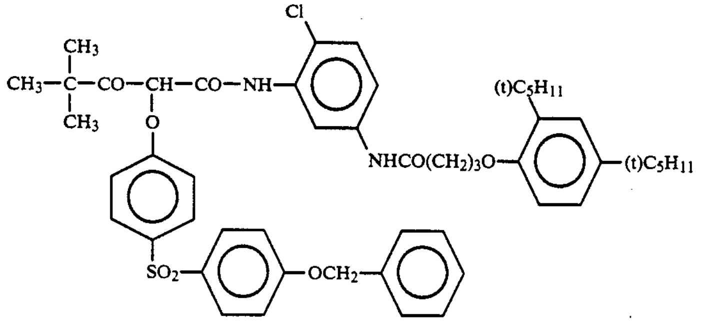

-continued
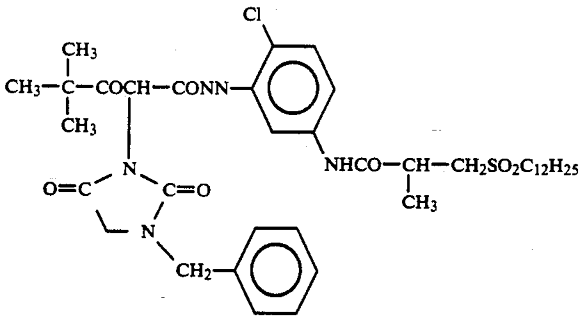
(Y-7)
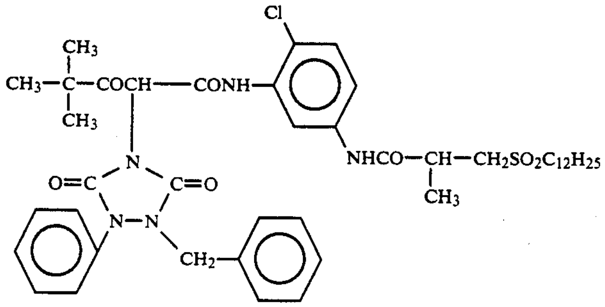
(Y-8)
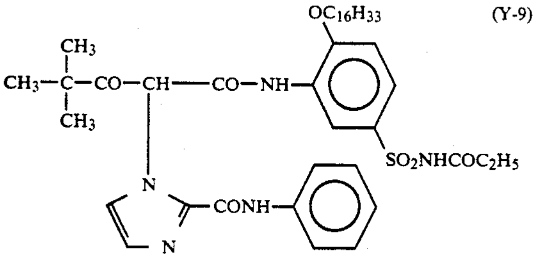
(Y-9)
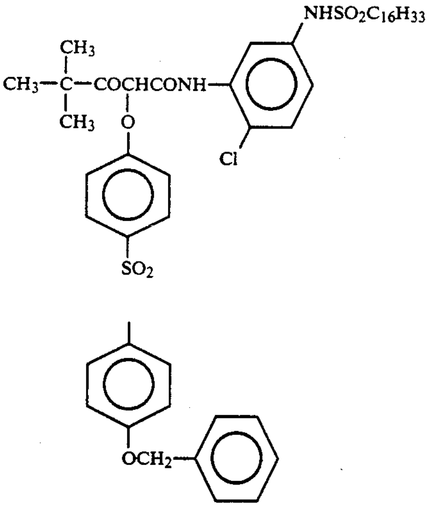
(Y-10)
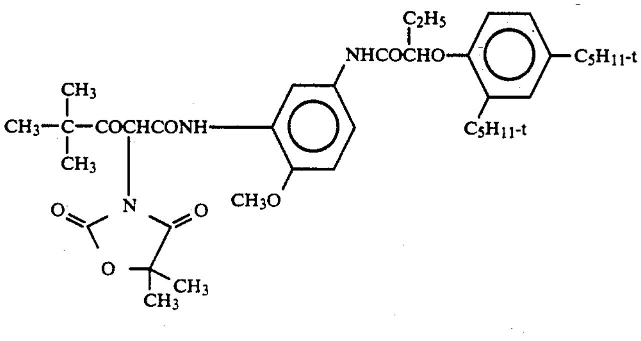
(Y-11)

-continued (Y-12)

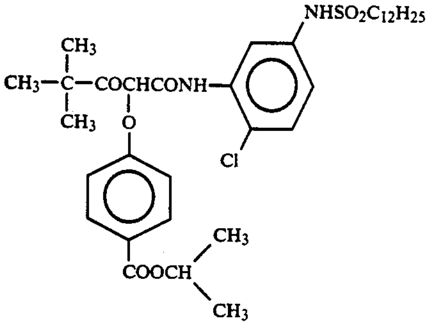

(Y-13)

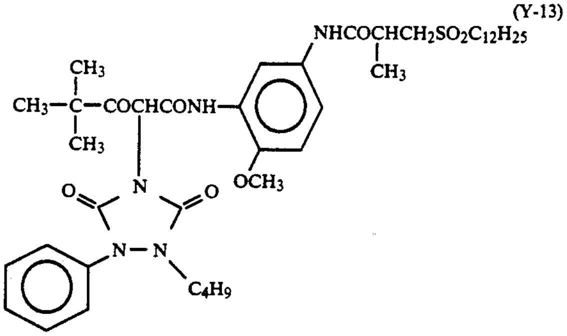

(Y-14)

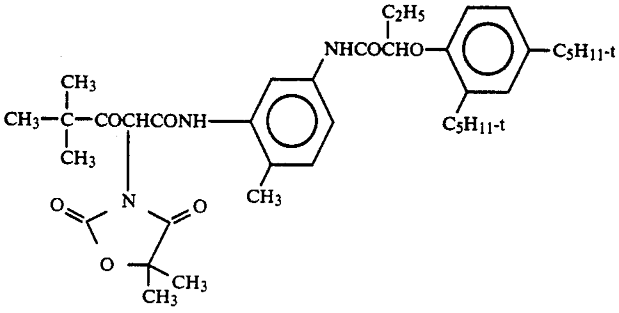

(Y-15)

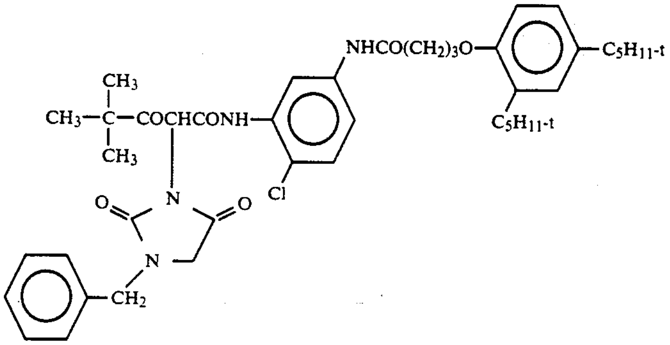

Preferred pyrazoloazole type megenta dye-forming couplers used in the present invention are, for instance, those represented by the following general formula (M)

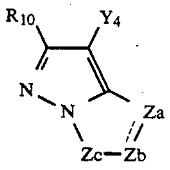

In Formula (M), $R_{10}$ represents a hydrogen atom or a substituent; $Y_4$ represents a hydrogen atom or an elimination group, in particular, a halogen atom or an arylthio group; Za, Zb and Zc each represents a methine, a substituted methine, =N— or —NH—, provided that one of the bonds Za—Zb and Zb—Zc is a double bond and the other is a single bond. When the Zb—Zc bond is a carbon-carbon double bond, the double bond may be a part of the aromatic ring. If a dimer or a higher polymer is formed at the position of $R_{10}$ or $Y_4$ and if Za, Zb or Zc is a substituted methine group, the dimer or the higher polymer may be formed at the substituted methine group.

Among the pyrazoloazole type couplers represented by Formula (M), imidazo [1,2-b] pyrazoles as disclosed in U.S. Pat. No. 4,500,630 are preferable because of low yellow minor absorption of the color developing due and fastness to light and pyrazolo [1,5-b] [1,2,4] triazole disclosed in U.S. Pat. No. 4,540,654 is particularly preferred.

In addition, preferred pyrazoloazole type couplers are, for instance, pyrazolotriazole couplers in which a branched alkyl group is bonded to the pyrazolotriazole ring at the 2, 3 or 6-position thereof as disclosed in Japanese Patent Unexamined Publication (hereinafter referred to as "J.P. KOKAI") No. Sho 61-65245; pyrazolotriazole couplers having a sulfonamido group in the molecule as disclosed in J.P. KOKAI No. Sho 61-65246; pyrazolotriazole couplers having an alkoxyphenylsulfonamido ballast group as disclosed in J.P. KOKAI No. Sho 61-147254; and pyrazolotriazole couplers having an alkoxy or aryloxy group at the 6-position of the pyrazolotriazole ring as disclosed in European Laid-Open Patent Nos. 226,849 and 294,785.

Typical examples of the magenta couplers represented by Formula (M) are as follows:

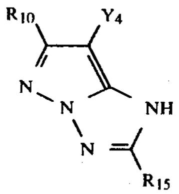
| Compound | $R_{10}$ | $R_{15}$ | $Y_4$ |
|---|---|---|---|
| M-9 | $CH_3$— | 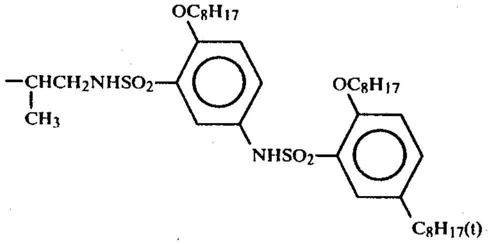 | Cl |
| M-10 | " | 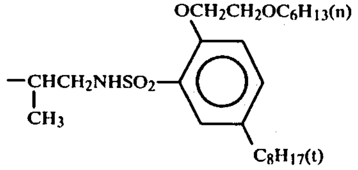 | " |
| M-11 | $(CH_3)_3C$— | 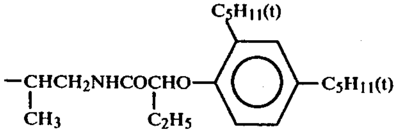 | 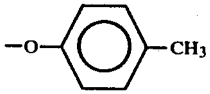 |
| M-12 | 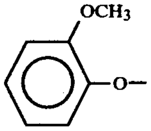 | 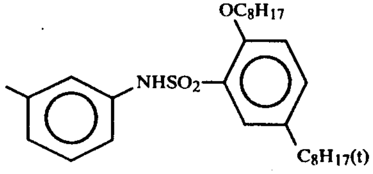 | 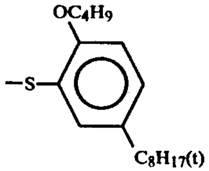 |

-continued
| | | | |
|---|---|---|---|
| M-13 | $CH_3-$ | 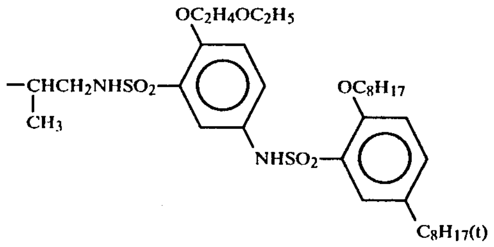 | Cl |
| M-14 | " | 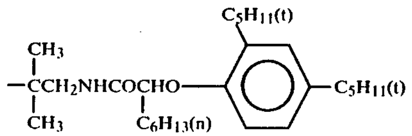 | " |
| M-15 | " | 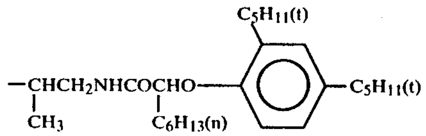 | " |
| M-16 | $CH_3-$ | 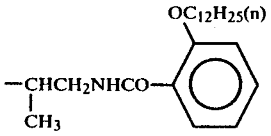 | Cl |
| M-17 | " | 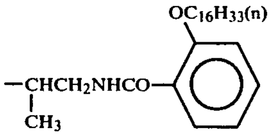 | " |

-continued
| | | | |
|---|---|---|---|
| M-18 | 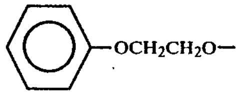 | 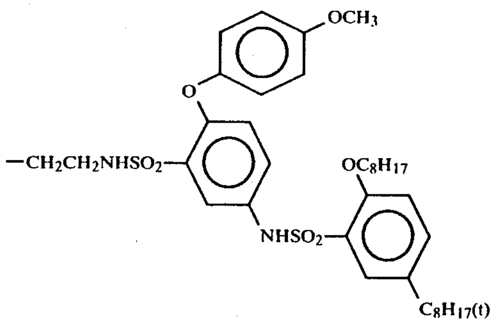 | 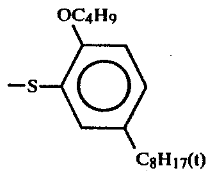 |
| M-19 | $CH_3CH_2O-$ | " | " |
| M-20 | 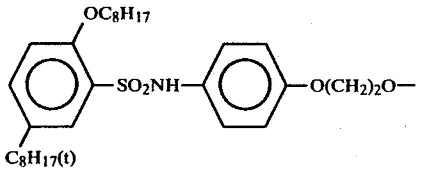 | 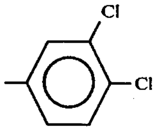 | 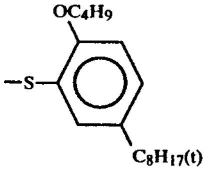 |
| M-21 | 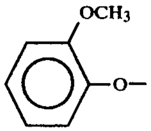 | 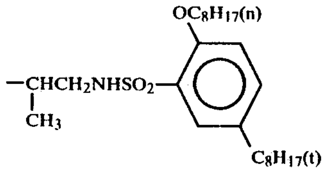 | Cl |
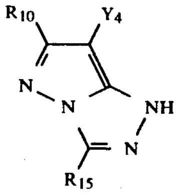
| Compound | $R_{10}$ | $R_{15}$ | $Y_4$ |
|---|---|---|---|

-continued
| | | | |
|---|---|---|---|
| M-22 | $CH_3-$ | 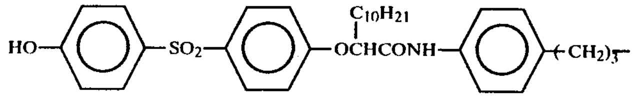 | Cl |
| M-23 | " | 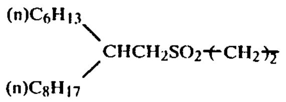 | " |
| M-24 | 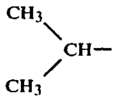 | 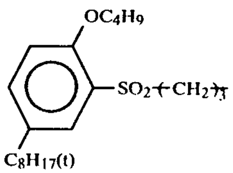 | " |
| M-25 | 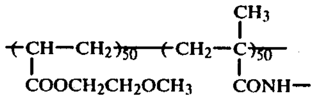 | 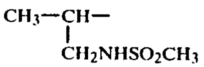 | " |
| M-26 | 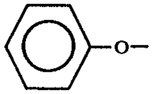 | 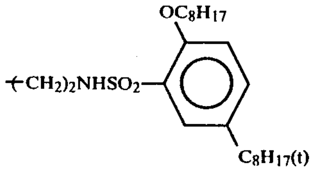 | Cl |
| M-27 | $CH_3-$ | 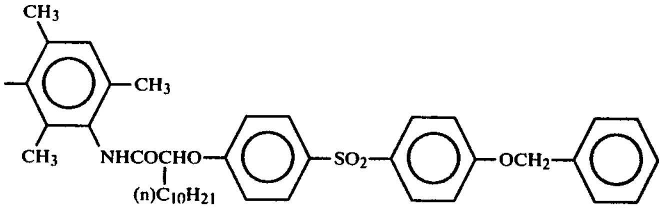 | " |

-continued
| | | | |
|---|---|---|---|
| M-28 | $(CH_3)_3C-$ | 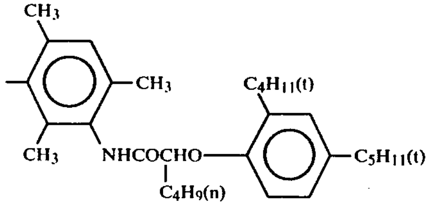 | " |
| M-29 | 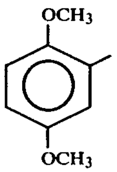 | 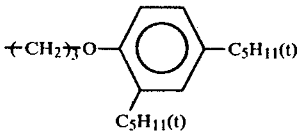 | Cl |
| M-30 | $CH_3-$ | 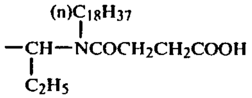 | " |

The water-insoluble and organic solvent-soluble polymers preferably employed in the present invention are those having a glass transition point of not less than 60° C. and more preferably not more than 90° C.

The preferred polymers have the structure comprising the following repeating units:

1) water-insoluble and organic solvent-soluble homopolymers and copolymers whose repeating unit has a —CO— bond in the main chain or the side chain thereof; and more preferably
2) water insoluble and organic solvent-soluble homopolymers and copolymers whose repeating unit has a —COO— bond in the main chain or the side chain thereof.
3) water-insoluble and organic solvent-soluble homopolymers and copolymers whose repeating unit has a group represented by the general formula: $—CO—N(G_1)G_2$ (wherein $G_1$ and $G_2$ each represents a hydrogen atom or a substituted or unsubstituted alkyl or aryl group, provided that $G_1$ and $G_2$ cannot represent a hydrogen atom simultaneously).

More preferably, the polymers comprising the repeating units defined in the foregoing item 3) in which either $G_1$ or $G_2$ is a hydrogen atom and the other represents a substituted or unsubstituted alkyl or aryl group having 3 to 12 carbon atoms.

The polymers used in the present invention will be explained in more detail with reference to specific examples thereof, but the present invention is not restricted to these specific polymers.

(A) vinyl Polymers

Specific examples of monomers from which the vinyl polymers used in the invention are formed are acrylates such as methyl acrylate, ethyl acrylate, n propyl acrylate, isopropyl acrylate, n-butyl acrylate, isobutyl acrylate, secbutyl acrylate, tert-butyl acrylate, amyl acrylate, hexyl acrylate, 2-ethylhexyl acrylate, octyl acrylate, tert-octyl acrylate, 2-chloroethyl acrylate, 2-bromoethyl acrylate, 4-chlorobutyl acrylate, cyanoethyl acrylate, 2-acetoxyethyl acrylate, dimethylaminoethyl acrylate, benzyl acrylate, methoxybenzyl acrylate, 2-chlorocyclohexyl acrylate, cyclohexyl acrylate, furfuryl acrylate, tetrahydrofurfuryl acrylate, phenyl acrylate, 2-hydroxybenzyl acrylate, 2,2-dimethyl-3-hydroxypropyl acrylate, 2-methoxyethyl acrylate, 3-methoxybutyl acrylate, 2-ethoxyethyl acrylate, 2-isopropoxy acrylate, 2-butoxyethyl acrylate, 2-(2-methoxyethoxy)ethyl acrylate, 2-(2-butoxyethoxy)ethyl acrylate, ω-methoxypolyethyle ne glycol acrylate (added molar number (n)=9), 1-bromo-2-methoxyethyl acrylate and 1,1-dichloro-2-ethoxyethyl acrylate. Moreover, it is also possible to use polymers obtained by polymerizing the following monomers:

Methacrylates such as methyl methacrylate, ethyl methacrylate, n-propyl methacrylate, isopropyl methacrylate, n-butyl methacrylate, isobutyl methacrylate, sec-butyl methacrylate, tert butyl methacrylate, amyl methacrylate, hexyl methacrylate, cyclohexyl methacrylate, benzyl methacrylate, chlorobenzyl methacrylate, octyl methacrylate, stearyl methacrylate, sulfopropyl methacrylate, N-ethyl N-phenylaminoethyl methacrylate, 2-(3-phenylpropyloxy)ethyl methacrylate, dimethylaminophenoxyethyl methacrylate, furfuryl methacrylate, tetrahydrofurfuryl methacrylate, phenyl methacrylate, cresyl methacrylate, naphthyl methacrylate, 2-hydroxyethyl methacrylate, 4-hydroxybutyl methacrylate, triethylene glycol monomethacrylate, dipropylene glycol monomethacrylate, 2-methoxyethyl methacrylate, 3-methoxybutyl methacrylate, 2-acetoxyethyl methacrylate, 2-acetoacetoxyethyl methacrylate, 2-ethoxyethyl methacrylate, 2-iso-propoxyethyl methacrylate, 2-butoxyethyl methacrylate, 2-(2-methoxyethoxy) ethyl methacrylate, 2-(2-ethoxyethoxy)ethyl methacrylate, 2-(2-butoxyethoxy)ethyl methacrylate, ω-methoxypolyethylene glycol methacrylate (added molar number (n)=6), allyl methacrylate and methacrylic acid-dimethylaminoethyl methyl chloride salt.

Vinyl esters such as vinyl acetate, vinyl propionate, vinyl butyrate, vinyl isobutyrate, vinyl caprcate, vinyl chloroacetate, vinyl methoxyacetate, vinylphenyl acetate, vinyl benzoate and vinyl salicylate.

Acrylamides such as acrylamide, methyl acrylamide, ethyl acrylamide, propyl acrylamide, butyl acrylamide, tert butyl acrylamide, cyclohexyl acrylamide, benzyl acrylamide, hydroxymethyl acrylamide, methoxyethyl acrylamide, dimethylaminoethyl acrylamide, phenyl acrylamide, dimethyl acrylamide, diethyl acrylamide, β-cyanoethyl acrylamide, N-(2-acetoacetoxyethyl) acrylamide and diacetone acrylamide.

Methacrylamides such as methacrylamide, methyl methacrylamide, ethyl methacrylamide, propyl methacrylamide, butyl methacrylamide, tert-butyl methacrylamide, cyclohexyl methacrylamide, benzyl methacrylamide, hydroxymethyl methacrylamide, methoxyethyl methacrylamide, dimethylaminoethyl methacrylamide, phenyl methacrylamide, dimethyl methacrylamide, diethyl methacrylamide, β-cyanoethyl methacrylamide and N-(2-acetoacetoxyethyl) methacrylamide.

Olefins such as dicyclopentadiene, ethylene, propylene, 1-butene, 1-pentene, vinyl chloride, vinylidene chloride, isoprene, chloroprene, butadiene and 2,3-dimethylbutadiene; styrenes such as styrene, methylstyrene, dimethylstyrene, trimethylstyrene, ethylstyrene, isopropylstyrene, chloromethylstyrene, methoxystyrene, acetoxystyrene, chlorostyrene, dichlorostyrene, bromostyrene methyl vinylbenzoate;

Vinyl ethers such as methyl vinyl ether, butyl vinyl ether, hexyl vinyl ether, methoxyethyl vinyl ether and dimethylaminoethyl vinyl ether;

Other monomers such as butyl crotonate, hexyl crotonate, dimethyl itaconate, dibutyl itaconate, diethyl maleate, dimethyl maleate, dibutyl maleate, diethyl fumarate, dimethyl fumarate, dibutyl fumarate, methyl vinyl ketone, phenyl vinyl ketone, methoxyethyl vinyl ketone, glycidyl acrylate, glycidyl methacrylate, N-vinyloxazolidone, N-vinylpyrrolidone, acrylonitrile, methacrylonitrile, vinylidene chloride, methylene malonitrile and vinylidene.

The monomers used for preparing the polymers employed in the invention (such as those listed above) may be used in combination to obtain copolymers, if necessary, for various purposes, for instance, of improving the solubility of the coupler. In addition, the following monomers having an acidic group in the molecule may also be used in the form of a co-monomer for the purpose of improving the color developability and solubility of the couplers so far as the resulting copolymer is not soluble in water.

Acrylic acid; methacrylic acid; itaconic acid; maleic acid, monoalkyl itaconates such as monomethyl itaconate, monoethyl itaconate and monobutyl itaconate; monoalkyl maleates such as monomethyl maleate, monoethyl maleate and monobutyl maleate; citraconic acid; styrenesulfonic acid; vinylbenzylsulfonic acid; vinylsulfonic acid; acryloyloxy alkylsulfonic acids such as acryloyloxy methylsulfonic acid, acryloyloxy ethylsulfonic acid and acryloyloxy propylsulfonic acid; methacryloyloxy alkylsulfonic acids such as methacryloyloxy methylsulfonic acid, methacryloyloxy ethylsulfonic acid and methacryloyloxy propylsulfonic acid; acrylamidoalkylsulfonic acids such as 2-acrylamido-2-methylethanesulfonic acid, 2-acrylamido 2-methylpropanesulfonic acid and 2-acrylamido-2-methylbutanesulfonic acid; methacrylamidoalkylsulfonic acids such as 2 methacrylamido-2-methylethanesulfonic acid, 2-methacrylamido-2-methylpropanesulfo nic acid and 2-methacrylamido-2-methylbutanesulfonic acid. These acids may be in the form of alkali metal (such as Na and K) or ammonium salts.

The vinyl monomers listed above as well as Other hydrophilic vinyl monomers (in other words, those which provide water-soluble homopolymers) are used as comonomers, the rate of the hydrophilic monomers is not restricted to a specific level so far as the resulting copolymer is not soluble in water, but the amount thereof is preferably not more than 40 mole%, more preferably not more than 20 mole% and most preferably not more than 10 mole%. On the other hand, if the hydrophilic co-monomer which is copolymerized with the monomer listed above has an acidic group, the amount of the co-monomer having an acidic group is in general not more than 20 mole%, preferably not more than 10 mole% and most preferably zero from the viewpoint of storability of images.

The monomers of the present invention in the polymers are preferably methacrylates, acrylamides and methacrylamides, in particular acrylamides and methacrylamides.

(B) Polymers Obtained Through Polycondensation and Addition

Polymerization

As polymers obtained by polycondensation, there have generally been known, for instance, polyesters of polyhydric alcohols with polybasic acids; and polyamides of diamines, dibasic acids and ω-amino- ω'-carboxylic acid. On the other hand, as polymers obtained by addition polymerization, there have been known, for instance, polyurethanes of diisocyanates with secondary alcohols.

Polyhydric alcohols effectively used in the invention are, for instance, glycols represented by the general formula: $HO—R_1—OH$ (wherein $R_1$ represents a hydrocarbon chain having 2 to about 12 carbon atoms, in particular an aliphatic hydrocarbon chain) or polyalkylene glycols and polybasic acids effectively used in the invention are, for instance, those represented by the general formula: $HOOC—R_2—COOH$ (wherein $R_2$ represents a single bond or a hydrocarbon group having 1 to about 12 carbon atoms).

Specific examples of such polyhydric alcohols are ethylene glycol, diethylene glycol, triethylene glycol, 1,2-propylene glycol, 1,3-propylene glycol, trimethylolpropane, 1,4 butanediol, isobutylenediol, 1,5-pentanediol, neopentyl glycol, 1,6-hexanediol, 1,7-heptanediol, 1,8 octanediol, 1,9-nonanediol, 1,10-decanediol, 1,11-undecanediol, 1,12-dodecanediol, 1,13-tridecanediol, 1,14-tetradecanediol, glycerin, diglycerin, triglycerin, 1-methylglycerin, erythrite, mannite and sorbite.

Specific examples of the polybasic acids are oxalic acid, succinic acid, glutaric acid, adipic acid, pimelic acid, cork acid, azelaic acid, sebacic acid, nonane dicarboxylic acid, decane dicarboxylic acid, undecane dicarboxylic acid, dodecane dicarboxylic acid, fumaric acid, maleic acid, itaconic acid, citraconic acid, phthalic acid, isophthalic acid, terephthalic acid, tetrachlorophthalic acid, mesaconic acid, isopiperic acid, cyclopentadiene-maleic anhydride adduct and rosin-maleic anhydride adduct.

(C) Other Polymers

For instance, polyesters obtained by the following ring-opening polymerization:

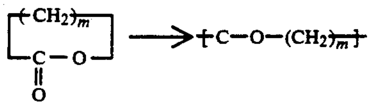

In the foregoing formula, m is an integer ranging from 4 to 7 and $—CH_2—$ chains may be branched ones.

Examples of monomers suitably used for preparing such polyesters are β-propiolactone, ε-caprolactone and dimethylpropiolactone.

The foregoing polymers may be used in any combination in the silver halide photographic light-sensitive material of the present invention.

The effects attained by the present invention are not greatly affected by the molecular weight and degree of polymerization of these polymers, but as the molecular weight thereof increases, various problems arise. For instance, it takes a long time period to perform the operation for solubilizing them in a co-solvent, it is difficult to emulsify and disperse them because of high viscosity, they easily form coarse particles and, as a result, the color developability is lowered and they have insufficient coating properties. The use Of a large amount of a CO solvent allows for the polymer to reduce the viscosity, but a new problem arises correspondingly. In the light of the foregoing problems, the viscosity of the polymer used which is determined by using a solution of 30 g of the polymer in 100 cc of a co-solvent is preferably not more than 5,000 cps, more preferably not more than 2,000 cps. The molecular weight of the polymers used in the invention is preferably not more than 150,000 and more preferably not more than 100,000.

The water-insoluble polymer herein means those having a solubility in water of not more than 3 g, preferably not more than 1 g per 100 g of distilled water.

The ratio of the amount of the polymer to that of a co-solvent widely varies depending on the kinds of the polymers used, the solubility thereof in a co-solvent, the degree of polymerization, the solubility of the coupler used in a co-solvent. In general, the co-solvent is used in an amount required for sufficiently lowering the viscosity of a solution comprising at least a coupler, a high boiling point solvent for the coupler and a polymer so that the solution can easily be dispersed in water or an aqueous hydrophilic colloid solution. Since the viscosity of the solution becomes high as the degree of polymerization increases, it is difficult to uniquely determine the ratio of the polymer to a co solvent irrespective of the kinds of the polymers, but the ratio is generally in the range of from about 1:1 to 1:50 (weight ratio), preferably 1:20 to 20:1 and more preferably 1:10 to 10:1.

The amount of the coupler represented by Formula (II) in general ranges from $2\times10^{-3}$ to $5\times10^{-1}$, preferably $1\times10^{-2}$ to $5\times10^{-1}$ per mole of the silver halide present in the silver halide emulsion layer.

A part of specific examples of the polymers used in the invention are as follows, but the present invention is not restricted to these specific ones.

| | |
|---|---|
| P-1) | Polyvinyl acetate; |
| P-2) | Polyvinyl propionate; |
| P-3) | Polymethyl methacrylate; |
| P-4) | Polyethyl methacrylate; |
| P-5) | Polyethyl acrylate; |
| P-6) | Vinyl acetate/vinyl alcohol copolymer (95:5); |
| P-7) | Poly(n-butyl acrylate); |
| P-8) | Poly(n-butyl methacrylate); |
| P-9) | Poly(isobutyl methacrylate); |
| P-10) | Poly(isopropyl methacrylate); |
| P-11) | Poly(decyl methacrylate); |
| P-12) | n-Butyl acrylate/acrylamide copolymer (95:5); |
| P-13) | Poly(methyl chloroacrylate); |
| P-14) | 1,4-Butanediol/adipic acid polyester; |
| P-15) | Ethylene glycol/sebacic acid polyester; |
| P-16) | Polycaprolactone; |
| P-17) | Poly(2-tert-butylphenyl acrylate); |
| P-18) | Poly(4-tert-butylphenyl acrylate); |
| P-19) | Copolymer of n-butyl methacrylate/N-vinyl-2-pyrrolidone (90:10); |
| P-20) | Methyl methacrylate/vinyl chloride copolymer (70:30); |
| P-21) | Methyl methacrylate/styrene copolymer (90:10) |
| P-22) | Methyl methacrylate/ethyl acrylate copolymer (50:50) |
| P-23) | n-Butyl methacrylate/methyl methacrylate/styrene copolymer (50:30:20); |
| P-24) | Vinyl acetate/acrylamide copolymer (85:15); |
| P-25) | Vinyl chloride/vinyl acetate copolymer (65:35); |
| P-26) | Methyl methacrylate/acrylonitrile copolymer (65:35); |
| P-27) | Diacetoneacrylamide/methyl methacrylate copolymer (50:50); |
| P-28) | Vinyl methyl ketone/isobutyl methacrylate copolymer (55:45); |
| P-29) | Ethyl methacrylate/n-butyl acrylate copolymer (70:30); |
| P-30) | Diacetoneacrylamide/n-butyl acrylate copolymer (60:40); |
| P-31) | Methyl methacrylate/cyclohexyl methacrylate copolymer (50:50); |
| P-32) | n-Butyl acrylate/styrene methacrylate/diacetoneacrylami de copolymer (70:20:10); |
| P-33) | N-tert-butylmethacrylamide/methyl methacrylate/acrylic acid copolymer (60:30:10); |
| P-34) | Methyl methacrylate/styrene/vinylsulfonamide copolymer (70:20:10); |
| P-35) | Methyl methacrylate/phenyl vinyl ketone copolymer (70:30); |
| P-36) | n-Butyl acrylate/methyl methacrylate/n-butyl methacrylate copolymer (35:35:30); |
| P-37) | n-Butyl methacrylate/benzyl methacrylate/N-vinyl-2-pyrrolidone copolymer (38:38:24); |
| P-38) | Methyl methacrylate/n-butyl methacrylate/isobutyl methacrylate/acrylic acid copolymer (37:29:25:9); |
| P-39) | n-Butyl methacrylate/acrylic acid copolymer (95:5); |
| P-40) | Methyl methacrylate/acrylic acid copolymer (95:5); |
| P-41) | Benzyl methacrylate/acrylic acid copolymer (90:10); |
| P-42) | n-Butyl methacrylate/methyl methacrylate/benzyl methacrylate/acrylic acid copolymer (35:35:25:5); |
| P-43) | n-Butyl methacrylate/methyl methacrylate/benzyl methacrylate copolymer (35:35:30); |
| P-44) | Poly(3-benzyl acrylate); |
| P-45) | Cyclohexyl methacrylate/methyl methacrylate/n-propyl methacrylate copolymer (37:29:34); |
| P-46) | Poly(benzyl methacrylate); |
| P-47) | Methyl methacrylate/n-butyl methacrylate copolymer (65:35); |
| P-48) | Vinyl acetate/vinyl propionate copolymer (75:25); |
| P-49) | n-Butyl methacrylate/sodium 3-acryloxybutane-1-sulfonate copolymer (97:3); |
| P-50) | n-Butyl methacrylate/methyl methacrylate/acrylamide copolymer (35:35:30); |
| P-51) | n-Butyl methacrylate/methyl methacrylate/vinyl chloride copolymer (37:36:27); |
| P-52) | n-Butyl methacrylate/styrene copolymer (90:10); |
| P-53) | Methyl methacrylate/N-vinyl-2-pyrrolidone copolymer (90:10); |
| P-54) | n-Butyl methacrylate/vinyl chloride copolymer (90:10); |
| P-55) | n-Butyl methacrylate/styrene copolymer (70:30); |
| P-56) | Poly(N-sec-butyl acrylamide); |

-continued

| | |
|---|---|
| P-57) | Poly(N-tert-butyl acrylamide); |
| P-58) | Diacetoneacrylamide/methyl methacrylate copolymer (62:38); |
| P-59) | Cyclohexyl methacrylate/methyl methacrylate copolymer (60:40); |
| P-60) | N-tert-Butyl acrylamide/methyl methacrylate copolymer (40:60); |
| P-61) | Poly(N-n-butyl acrylamide); |
| P-62) | (tert-butyl methacrylate)/N-tert-butyl acrylamide copolymer (50:50); |
| P-63) | tert-Butyl methacrylate/methyl methacrylate copolymer (70:30); |
| P-64) | Poly(N-tert-butyl methacrylamide); |
| P-65) | N-tert-Butyl acrylamide/methyl methacrylate copolymer (60:40); |
| P-66) | Methyl methacrylate/acrylonitrile copolymer (70:30); |
| P-67) | Methyl methacrylate/vinyl methyl ketone copolymer (38:62); |
| P-68) | Methyl methacrylate/styrene copolymer (75:25); |
| P-69) | Methyl methacrylate/hexyl methacrylate copolymer (70:30); |
| P-70) | Poly(benzyl acrylate); |
| P-71) | Poly(4-biphenyl acrylate); |
| P-72) | Poly(4-butoxycarbonylphenyl acrylate); |
| P-73) | Poly(sec-butyl acrylate); |
| P-74) | Poly(tert-butyl acrylate); |
| P-75) | Poly(3-chloro-2,2-bis(chloromethyl)propyl acrylate); |
| P-76) | Poly(2-chlorophenyl acrylate); |
| P-77) | Poly(4-chlorophenyl acrylate); |
| P-78) | Poly(pentachlorophenyl acrylate); |
| P-79) | Poly(4-cyanobenzyl acrylate); |
| P-80) | Poly(cyanoethyl acrylate); |
| P-81) | Poly(4-cyanophenyl acrylate); |
| P-82) | Poly(4-cyano-3-thiabutyl acrylate); |
| P-83) | Poly(cyclohexyl acrylate); |
| P-84) | Poly(2-ethoxycarbonylphenyl acrylate); |
| P-85) | Poly(3-ethoxycarbonylphenyl acrylate); |
| P-86) | Poly(4-ethoxycarbonylphenyl acrylate); |
| P-87) | Poly(2-ethoxyethyl acrylate); |
| P-88) | Poly(3-ethoxyethyl acrylate); |
| P-89) | Poly(1H,1H,5H-octafluoropentyl acrylate); |
| P-90) | Poly(heptyl acrylate); |
| P-91) | Poly(hexadecyl acrylate); |
| P-92) | Poly(hexyl acrylate); |
| P-93) | Poly(isobutyl acrylate); |
| P-94) | Poly(isopropyl acrylate); |
| P-95) | Poly(3-methoxybutyl acrylate); |
| P-96) | Poly(2-methoxycarbonylphenyl acrylate); |
| P-97) | Poly(3-methoxycarbonylphenyl acrylate); |
| P-98) | Poly(4-methoxycarbonylphenyl acrylate); |
| P-99) | Poly(2-methoxyethyl acrylate); |
| P-100) | Poly(4-methoxyethyl acrylate); |
| P-101) | Poly(3-methoxyethyl acrylate); |
| P-102) | Poly(3,5-dimethyladamantyl acrylate); |
| P-103) | Poly(3-dimethylaminophenyl acrylate); |
| P-104) | Poly(vinyl-tert-butylate); |
| P-105) | Poly(2-methylbutyl acrylate); |
| P-106) | Poly(3-methylbutyl acrylate); |
| P-107) | Poly(1,3-dimethylbutyl acrylate); |
| P-108) | Poly(2-methylpentyl acrylate); |
| P-109) | Poly(2-naphthyl acrylate); |
| P-110) | Poly(phenyl methacrylate); |
| P-111) | Poly(propyl acrylate); |
| P-112) | Poly(m-tolyl acrylate); |
| P-113) | Poly(o-tolyl acrylate); |
| P-114) | Poly(p-tolyl acrylate); |
| P-115) | Poly(N,N-dibutyl acrylamide); |
| P-116) | Poly(isohexyl acrylamide); |
| P-117) | Poly(isooctyl acrylamide); |
| P-118) | Poly(N-methyl-N-phenyl acrylamide); |
| P-119) | Poly(adamantyl methacrylate); |
| P-120) | Poly(benzyl methacrylate); |
| P-121) | Poly(2-bromoethyl methacrylate); |
| P-122) | Poly(2-N-tert-butylaminoethyl methacrylate); |
| P-123) | Poly(sec-butyl methacrylate); |
| P-124) | Poly(tert-butyl methacrylate); |
| P-125) | Poly(2-chloroethyl methacrylate); |
| P-126) | Poly(2-cyanoethyl methacrylate); |
| P-127) | Poly(2-cyanomethylphenyl methacrylate); |
| P-128) | Poly(4-cyanophenyl methacrylate); |
| P-129) | Poly(cyclohexyl methacrylate); |
| P-130) | Poly(dodecyl methacrylate); |

-continued

| | |
|---|---|
| P-131) | Poly(diethylaminoethyl methacrylate); |
| P-132) | Poly(2-ethylsulfinylethyl methacrylate); |
| P-133) | Poly(hexadecyl methacrylate); |
| P-134) | Poly(hexyl methacrylate); |
| P-135) | Poly(2-hydroxypropyl methacrylate); |
| P-136) | Poly(4-methoxycarbonylphenyl methacrylate); |
| P-137) | Poly(3,5-dimethyladamantyl methacrylate); |
| P-138) | Poly(dimethylaminoethyl methacrylate); |
| P-139) | Poly(3,3-dimethylbutyl methacrylate); |
| P-140) | Poly(3,3-dimethyl-2-butyl methacrylate); |
| P-141) | Poly(3,3,5-trimethylhexyl methacrylate); |
| P-142) | Poly(octadecyl methacrylate); |
| P-143) | Poly(tetradecyl methacrylate); |
| P-144) | Poly(4-butoxycarbonylphenyl methacrylamide); |
| P-145) | Poly(4-carboxyphenyl methacrylamide); |
| P-146) | Poly(4-ethoxycarbonylphenyl methacrylamide); |
| P-147) | Poly(4-methoxycarbonylphenyl methacrylamide); |
| P-148) | Poly(butylbutoxycarbonyl methacrylamide); |
| P-149) | Poly(butyl chloroacrylate); |
| P-150) | Poly(butyl cyanoacrylate); |
| P-151) | Poly(cyclohexyl chloroacrylate); |
| P-152) | Poly(ethyl chloroacrylate); |
| P-153) | Poly(ethylethoxycarbonyl methacrylate); |
| P-154) | Poly(ethyl methacrylate); |
| P-155) | Poly(ethyl fluoromethacrylate); |
| P-156) | Poly(hexylhexyloxycarbonyl methacrylate); |
| P-157) | Poly(isobutyl chloroacrylate); |
| P-158) | Poly(isopropyl chloroacrylate); |
| P-159) | Trimethylenediamine/glutaric acid polyamide; |
| P-160) | Hexamethylenediamine/adipic acid polyamide; |
| P-161) | Poly(α-pyrrolidone); |
| P-162) | Poly(ε-caprolactam); |
| P-163) | Hexamethylenediisocyanate/1,4-butanediol polyurethane; |
| P-164) | p-Phenylenediisocyanate/ethylene glycol polyurethane. |

PREPARATION EXAMPLE A: POLY(METHYL METHACRYLATE) (P-3)

50.0 g of methyl methacrylate, 0.5 g of sodium polyacrylate and 200 mλ of distilled water were introduced into a 500 mλ volume three-necked flask and heated to 80° C. in a nitrogen stream with stirring. 500 mg of dimethyl azobisisobutyrate as a poolymerization initiator was added to the mixture to initiate the polymerization reaction.

After the polymerization reaction was continued for 2 hours, the polymerization solution was cooled, the resulting polymer in the form of beads was recovered by filtration and washed to give 48.7 g of P-3.

PREPARATION EXAMPLE B: POLY(T-BUTY ACRYLAMIDE) (P-75)

A mixture of 50.0 g of t butyl acrylamide and 250 mλ of toluene was introduced into a 500 mλ volume three-necked flask and heated to 80° C. in a nitrogen stream with stirring. 10 mλ of a solution of 500 mg of azobisisobutyronitrile as a polymerization initiator in toluene was added to the mixture to initiate the polymerization reaction.

After the polymerization reaction was continued for 3 hours, the polymerization solution was cooled and poured into 1 λ of hexane. The resulting solid precipitated was filtered off, washed with hexane and heated under a reduced pressure to dry the solid to thus give 47.9 g of P-57.

The couplers represented by Formula (I) will hereunder be described in detail.

Most of these couplers are soluble in an oil. Usually, it is preferred that the coupler be dissolved in a high boiling solvent (if necessary, in combination with a low boiling solvent), the solution is emulsified or dispersed in an aqueous gelatin solution and the emulsion or suspension is added to a silver halide emulsion. When the coupler is soluble in an aqueous alkali solution, it is dissolved therein together with a developing agent and other additives and the solution is used for forming an image by so called coupler-in-developer process.

Further the coupler can be used together with the developing agent and the alkali (if necessary, in the presence of an Organic solvent) for an oxidation coupling with an oxidizing agent (such as a persulfate, silver nitrate, nitrous acid or a salt thereof). When X of Formula (I) is a hydrogen atom, it can form a colorant by condensation with a p-nitrosoaniline in the presence of an alkali or acetic anhydride. The cyan dye thus formed is usable widely as, for instance, dye for filter, paint, ink, image-formation information recording and printing.

When the coupler is added to the silver halide emulsion, a hydroquinone derivative, U.V. absorber or known fading inhibitor can be used, if necessary, for controlling or improving the color developability.

The foregoing high-boiling solvents are those having a melting point of 100° C. or less (preferably 80° C. or less) and a boiling point of 140° C. or higher (preferably 160° C. or higher) and in which the coupler is soluble. They include, for instance, phosphoric esters such as tricresyl phosphate, trioctyl phosphate and tricyclohexyl phosphate; organic acid esters such as dibutyl phthalate, dioctyl phthalate, dicyclohexyl phthalate, dodecyl benzoate and bis(2-ethylhexyl)sebacate; ethers including epoxy compounds; amides and amines. They further include cyclic compounds. In addition, high-boiling organic solvents used in an oil-in-water dispersion methods can also be used.

The silver halide color photographic light-sensitive material containing the coupler represented by Formula(I) of the present invention will be described below in detail.

The cyan dye-forming coupler of Formula (I) is contained in at least one layer of the silver halide light-sensitive material for color photographs of the present invention.

The silver halide light-sensitive material for color or photographs of the present invention can be a multilayer, multi-color photographic material comprisingat least two layers having different spectral sensitivities formed on a substrate. Multi-layer, natural color photographic materials comprise at least one red sensitive emulsion layer, at least one green-sensitive emulsion layer and at least one blue-sensitive emulsion layer formed or a substrate. The arrangement of these layers may be any order properly selected. A preferred arrangement of the layers is a structure of a red-sensitive layer, a green-sensitive layer and a blue-sensitive layer in order from the side of the substrate; a blue-sensitive layer, a green-sensitive layer and a red-sensitive layer in order from the side of the substrate; or a blue-sensitive layer, a red-sensitive layer and a green-sensitive layer in order from the side of the substrate. Any color sensitive emulsion layer may comprise two or more sub-emulsion layers sensitive to the same color but having different sensitivity in order to improve the sensitivity. Further, an emulsion layer may comprise three sublayers in order to improve the graininess. A non-light-sensitive layer may be placed between or among two or more emulsion layers sensitive to the same color. In another structure, an emulsion layer sensitive to a different color may be placed between two emulsion layers sensitive to the Same color. A reflective layer comprising, for instance, fine silver halide grains may be placed below a highly sensitive layer, particularly highly blue-sensitive layer to improve the sensitivity. A yellow filter layer may also be formed.

Usually, the red-sensitive emulsion layer contains a cyan-forming coupler, the green-sensitive emulsion layer contains a magenta-forming coupler and the blue-sensitive emulsion layer contains a yellow-forming coupler. A cyan coupler of Formula (I) can be used as the whole cyan forming coupler or as a part thereof. If necessary, other combinations are also Possible. For instance, an infrared ray-sensitive layer can be used for the exposure of pseudo color prints or semiconductor laser. In a typical example, the cyan coupler used in the present invention is incorporated as a main coupler in the red-sensitive emulsion layer or a layer adjacent thereto. Further the cyan coupler used in the present invention can be incorporated as the main coupler in the blue-sensitive, green-sensitive or red-sensitive emulsion layer. In addition, it is usable in combination with another main coupler.

The standard amount of the cyan coupler used in the invention is in the range of from 0.001 to 1 mole, preferably 0.003 to 0.3 mole per mole of the light-sensitive silver halide.

The cyan coupler used in the present invention is also usable in combination with a magenta coupler or a yellow coupler in an emulsion layer sensitive to a color different from the color to which the cyan-coupler-containing emulsion layer is sensitive. Another known cyan coupler can also be incorporated in the same layer or another layer so far as the effect of the invention is not impaired. The cyan, magenta and yellow couplers usable in the invention in combination with the coupler of Formula (I) include those represented by the general formulae (I) to (v) shown on page 4 and 5 of EP 0231832 A 2. In particular, the cyan couplers are described on page 12 to 24, magenta couplers on pages 25 to 43 and yellow couplers on page 44 to 64 of the EP patent.

The color light-sensitive material of the invention containing a coupler of Formula (I) is usable in various fields. For instance, it is usable as a material for ordinary or movie negative color films and reversal color films for slides and televisions. It is also usable as a material for color paper, positive color films and reversal color paper. The light-sensitive material of the invention is also usable as a monochromatic light-sensitive material according to a technique of mixing three color couplers as described in Research Disclosure No. 17123 (July, 1987).

The silver halide emulsions used for forming the light-sensitive material of the invention are not particularly limited and those known in the art can be used. For instance, the silver halide emulsions disclosed in J.P. KOKAI No. Sho 61-198236 (corresponding to U.S. Pat. No. 4,707,436) a In particular, silver halides described from line 10, upper right column, to line 7, lower left column, page 5 of the Patent Gazette; silver halide emulsions described from line 8, lower left column, page 5 to line 3, lower right column, page 7; couplers described from line 4, lower right column, page 7 to line 2, lower left column, page 8; and additives such as color antifoggant described from line 3, lower left column, page 8 to line 11, upper left column, page 9 are usable.

In particular, when the silver halide light-sensitive material of the invention is used for a direct positive color film or a direct positive color paper, direct positive silver iodide of internal latent image type is preferably used as silver halide. Further, when the silver halide light-sensitive material of the invention is used for a reversal color film, silver bromoiodide (content of silver iodide preferably ranges from 2 to 15 mole%) is preferably used as silver halide. Moreover, when the silver halide light sensitive material of the invention is used for color paper or a light sensitive material for color printing, a silver halide emulsion containing silver chloride or silver chlorobromide substantially free of silver iodide is preferably used. The silver iodide content of the silver chlorobromide substantially free of silver iodide is 1 mole% or less, preferably 0.2 mole% or less. Although halogen composition of the emulsion may be identical or different between grains, an emulsion having an identical halogen composition between grains easily makes properties of grains uniform. As for halogen distribution in grains contained in a silver halide emulsion, suitable grains can be selected from the following group: so-called uniform structure grains with homogeneous composition; so-called core/shell structure grains of which halogen composition is different between core or internal part of a silver halide grain and shell part (consisting of one or more layers) surrounding the core part; and grains having a non lamellar part(s) with different halogen composition in an internal part of the grains or on the surface of the grains (when the grains have the non-lamellar part on the surface, such a part is conjugated at the edge or the corner, or on the plain surface). The two latter grains are advantageous rather than the former one (the uniform structure grains) for high sensitivity, and they are also preferred from the viewpoint of the pressure resistance. When the silver halide grains have the foregoing structures, the boundary between two different halogen compositions may be clear, or unclear boundary may be formed by mixture of crystals with different compositions, or the composition of the boundary may be continuously changed by intention.

The silver bromide/silver chloride ratio of the silver chlorobromide emulsion can be optionally selected. This ratio can be changed widely according to the purpose and the silver chloride content is preferably 2% or more.

So-called high silver chloride content emulsion with high silver chloride concentration is preferably used for light-sensitive material suitable to a rapid processing. The silver chloride content thereof is preferably 90 mole% or more, more preferably 95 mole% or more.

In the high silver chloride content emulsion, silver bromide localizing layer is preferably located in an internal part of a silver halide grain and/or on the surface thereof in the lamellar or non-lamellar state. As for halogen composition of the localizing layer, silver bromide content is preferably at least 10 mole%, more preferably more than 20 mole%. The localizing layer may be present in the grain core, at the edge or corner of the grain surface, or on the grain surface and is preferably be conjugated by epitaxial growth on the corner of the grain.

The uniform structure-grains of which halogen distribution in grains is small is preferably used for a high silver chloride emulsion with 90 mole% or more silver chloride content for the purpose of inhibiting reduction of sensitivity when a light sensitive material is pressed.

It is advantageous to further increase the silver chloride content in the silver halide emulsion for the purpose of reducing a replenisher for development. In this case, a pure silver chloride emulsion containing 98 to 99.9 mole% of silver chloride is also used preferably.

Mean particle size of silver halide grains contained in the silver halide emulsion of the invention, which is a number average particle size calculated in terms of diameter of circle obtained from projected area of particles, is preferably from 0. 1 to 2 μm.

As for particle size distribution of the grains, so-called monodispersed emulsion with the degree of variability of 20% or less, preferably 15% or less (the degree is obtained by division of standard deviation of particle size by average particle size) is preferred. In this case, the foregoing monodispersed emulsions may be blended and contained in an emulsion layer, or the emulsions may be contained in two or more emulsion layers in order to obtain wide latitude.

Silver halide grains in the photographic emulsion may be so-called regular grains which have a regular crystal shape such as cubic, octahedron or tetradecahedron, grains having an irregular crystal shape such as sphere or tabula, or grains having a composite shape thereof. Further silver halide grains may be a mixture of grains with various crystal shape. In the present invention, an emulsion containing 50% or more, preferably 70% or more, more preferably 90% or more of the grains having a regular crystal shape.

An emulsion containing more than 50% (on the basis of the projected area of the whole grains) of flat grains which have an aspect ratio (diameter calculated in terms of circle/thickness) of 5 or more, preferably 8 or more, is also used preferably.

Silver halide emulsions used for the present invention may contain various polyvalent metal ion impurities during process for forming emulsified particles or physical ripening. Examples of compounds used include cadmium, zinc, lead, copper and thallium salts, and salts or complex salts of Group VIII elements such as iron, ruthenium, rhodium, palladium, osmium, iridium and platinum. Particularly, elements belonging to Group VIII of the Periodic Table are preferably used. An added amount of the foregoing salts may widely vary depending on the purposes of using the same and preferably ranges from $10^{-9}$ to $10^{-2}$ mole% on the basis of the silver halide used.

The silver halide emulsion used in the invention may be chemically or spectrally sensitized.

In the case of chemical sensitization, sulfur sensitization typically using unstable sulfur compounds, noble metal sensitization such as gold sensitization, or reduction sensitization or combination thereof may be used.

Compounds described in J.P. KOKAI No. Sho 62-215272 (p. 18, right-lower column to p. 22, right upper column) are preferably used.

The coupler of Formula (I) used in the invention can be introduced into the light-sensitive material according to various known dispersion methods such as oil-in-water dispersion method.

High boiling organic solvents having a boiling point under atmospheric pressure of at least 175° C. used in the oil-in water dispersion method include, for instance, phthalic esters such as dibutyl phthalate, dicyclohexyl phthalate, di-2-ethylhexyl phthalate, decyl phthalate, bis(2,4-di-t-amylphenyl) phthalate, bis(2,4-di-t-amylphenyl) isophthalate and bis(1,1-diethylpropyl) phthalate; phosphoric and phosphonic esters such as triphenyl phosphate, tricresyl phosphate, 2-ethylhexyldiphenyl phosphate, tricyclohexyl phosphate, tri-2-ethylhexyl phosphate, tridodecyl phosphate, tributoxyethyl phosphate, trichloropropyl phosphate and di-2-ethylhexylphenyl phosphonate; benzoic esters such as 2-ethylhexyl benzoate, dodecyl benzoate and 2-ethylhexyl-p-hydroxybenzoate; amides such as N,N-diethyldodecaneamide, N,N-diethyllaurylamide and N-tetradecylpyrrolidone; alcohols and phenols such as isostearyl alcohol and 2,4-di-t-amylphenol; aliphatic carboxylic esters such as bis(2-ethylhexyl) sebacate, dioctyl azelate, glycerol tributyrate, isostearyl lactate and trioctyl citrate; aniline derivatives such as N,N-dibutyl-2-butoxy-5-t-octylaniline; and hydrocarbons such as paraffin, dodecylbenzene and diisopropylnaphthalene. Co-solvent usable herein include, for instance, organic solvents having a boiling point of at least about 30° C., preferably in the range of from 50° C. to about 160° C. Typical examples thereof include ethyl acetate, butyl acetate, ethyl propionate, methyl ethyl ketone cyclohexanone, 2-ethoxyethyl acetate and dimethylformamide.

When the coupler of Formula (I) is to be dispersed according to the oil-in-water dispersion method, the high-boiling organic solvent used therein is preferably at least one of the compounds of the following formulae (VI) and (VII) and particularly further with a co-solvent (such as ethyl acetate). The weight ratio of the high-boiling organic solvent to the coupler is preferably 0.6 or less and more preferably 0.4 or less. Namely, the co-solvent can be used alone for the dispersion to obtain excellent results.

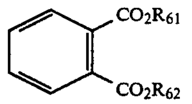

(VI)

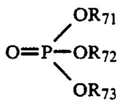

(VII)

Wherein $R_{61}$ and $R_{62}$ may be the same or different and each represents an alkyl group, a cycloalkyl group, an alkenyl group or an aryl group, provided that the number of total carbon atoms in $R_{61}$ and $R_{62}$ is 4 to 30; $R_{71}$, $R_{72}$ and $R_{73}$ may be the same or different and each represents an alkyl group, a cycloalkyl group, an alkenyl group or an aryl group, provided that the number of total carbon atoms in $R_{71}$, $R_{72}$ and $R_{73}$ is 12 to 60.

The steps of the latex dispersion method, the effects thereof and the kinds of the latexes usable for the impregnation are described in, for instance, U.S. Pat. No. 4,199,363 and German Patent Appln (OLS) Nos. 2,541,274 and 2,541,230.

The suitable substrate for the silver halide light-sensitive material usable in the present invention are those disclosed on page 28 of the aforementioned RD. No. 17643, and from the right column, page 647 to the left column, page 648 of RD. No. 18716.

The color photographic material according to the present invention can be developed by an ordinary method described on pages 28 to 29 of the foregoing RD. No. 17643 and from the left column to the right column, page 651 of RD. No. 18716.

The silver halide light-sensitive material of the invention for color photographs is usually subjected to a desilverization treatment, washed with water and/or subjected to a stabilization step. The amount of water used in the washing step is variable over a wide range depending on the properties of the light-sensitive material (due to couplers, etc. used), the use, temperature of water, number of washing tanks (number of stages), feeding system (either countercurrent or parallelflow system) and various other conditions. Among them, the relationship between the number of tanks for washing water and the amount of water in the multi-stage countercurrent system can be determined by a method disclosed in "Journal of the Society of Motion Picture and Television Engineers", vol. 64, pp. 284-253 (May, 1955).

Although the amount of water used for washing can be remarkably reduced by the multi-stage countercurrent method described in the foregoing literature, a problem that bacteria propagate arises because of a prolonged residence time of water in the tanks and, therefore, the suspended matter thus formed contaminates the light-sensitive material. In the treatment of the color light-sensitive material of the present invention, the problem can be solved by a method disclosed in J.P. KOKAI No. Sho 62-288838 wherein the amount of calcium ions and magnesium ions is reduced. Further germicides can be used. The germicides usable herein include, for instance, isothiazolone compounds and thiabendazoles described in J.P. KOKAI No. Sho 57 8542, chlorine atom-containing germicides such as chlorinated sodium isocyanurate, and germicides described in Hiroshi HORIGUCHI, "Bokin Bobai No Kagaku", "Biseibutsu No Mekkin, Sakkin, Bobai Gijutsu", edited by "Eisei Gijutsu-Kai and Bokin Bobaizai Jiten", edited by Nippon Bokin Bobai Gakkai such as benzotriazole.

pH of water used for washing in the treatment of the light-sensitive material of the invention ranges from 4 to 9, preferably 5 to 8. The temperature of water and the washing time may vary depending on the properties of the light-sensitive material and the use thereof. Usually, the temperature and the time range from 15° to 45° C. and 20 sec to 10 min, preferably 25° to 40° C. and 30 sec to 5 min, respectively. Further the light-sensitive material of the invention can be treated directly with a stabilizer in place of washing with water. In the stabilization treatment, any of known methods as described in J.P. KOKAI Nos. Sho 57-8543, Sho 58-14834 and Sho 60-200345 can be employed.

If necessary, the light sensitive material is stabilized after washing with water. The stabilization bath usable herein is, for instance, a bath containing formalin and a surfactant usually used as a final bath for photographic color light-sensitive materials. The stabilization bath may also contain chelating agents and antifungal agents.

The overflow generated during the water washing process and/or feeding of the stabilizer can be reused in other steps such as the desilverization step.

The silver halide color light sensitive material of the invention may contain a color developing agent in order to facilitate or accelerate the treatment. The color developing agent to be incorporated therein are preferably in the form of precursors thereof. They include, for instance, indoaniline compounds described in U.S. Pat. No. 3,342,597; Schiff base-type compounds as described in U.S. Pat. No. 3,342,599 and Research Disclosure Nos. 14850 and 15159; aldole compounds as disclosed in Research Disclosure No. 13924; metal salt complexes as disclosed in U.S. Pat. No. 3,719,492; and urethane compounds disclosed in J.P. KOKAI No. Sho 53 135628.

The silver halide color light-sensitive material of the present invention may contain a 1-phenyl-3 pyrazolidone compound in order to accelerate the color development, if necessary. Typical examples thereof are those disclosed in J.P. KOKAI Nos. Sho 56-64339, Sho 57-144547 and Sho 58-115438.

The temperature of the liquids used for the treatments in the present invention is 10° to 50° C., usually 33° to 38° C. A higher temperature may also be used in order to accelerate the treatments or to reduce the treatment time or, on the contrary, a lower temperature can be used in order to improve the quality of the image or stability of the treating solution. Cobalt intensifiers or hydrogen peroxide intensifiers described in German Patent No. 2,226,770 and U.S. Pat. No. 3,674,499 can be used for saving silver in the light sensitive material.

The silver halide light-sensitive material of the invention is also usable as a heat development type light-sensitive material described in U.S. Pat. No. 4,500,626; J.P. KOKAI Nos. Sho 60-133449, Sho 59-218443 and Sho 61-238056, European Patent No. 210,660 A2, and so on.

The silver halide color photographic light-sensitive material of the invention in which the coupler of Formula (II) is incorporated will now be described in detail.

The compounds of the invention are oil-soluble. Therefore, in general the compound is preferably dissolved or dispersed in a high-boiling solvent (if necessary, in combination with a low-boiling solvent) together with the cyan coupler of the invention and then incorporated into the silver halide emulsion and at this stage, hydroquinone derivatives, U.V. absorbers or known fading inhibitors may be incorporated, if necessary and the compound of the invention may be used alone or in combination. When the compound is incorporated into the silver halide emulsion, one or more of the compounds and optional hydroquinone derivatives, U.V. absorbers or known fading inhibitors are dissolved in a high-boiling solvent, optionally used in combination with a low boiling solvent, mixed with an aqueous solution containing a hydrophilic binder, emulsified and dispersed with a high speed rotating mixer, a colloid mill, an ultrasonic dispersion apparatus or the like and then added to the silver halide emulsion. The high boiling solvent herein usable are, for instance, organic acid amides, carbamates, esters, ketones, urea derivatives, in particular di-n butyl phthalate, tri-cresyl phosphate, di-isooctyl azelate, di-n-butyl sebacate, tri-n-hexyl phosphate, N,N-di-ethylcaprylamide butyl, n-pentadecyl phenyl ether or fluorinated paraffins; examples of the low-boiling solvents are ethyl acetate, butyl acetate, butyl propionate, cyclohexanol, cyclohexane, tetrahydrofuran. These high- and low-boiling solvents may be used alone or in combination. The hydrophilic binder used in the invention are, for instance, gelatin or the like and the aqueous solution thereof may comprise an anionic surfactant such as alkylbenzene-sulfonic acid, alkylnaphthalenesulfonic acid and/or a nonionic surfactant such as sorbitan sesquioleate and sorbitan monolaurate.

In the present invention the couplers represented by the following general formulae (C-I), (C-II) or (M-I) may be used in addition to the foregoing couplers of Formula (II), (Y) or (M).

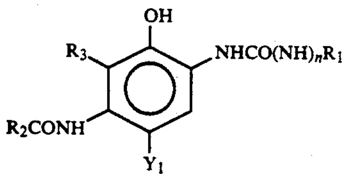

General Formula (C-I)

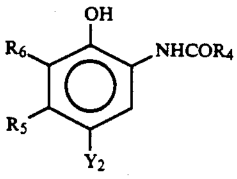

General Formula (C-II)

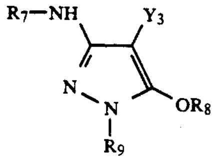

General Formula (M-1)

In the general formulae (C-I) and (C-II), R,. R, and R. each represents a substituted or unsubstituted aliphatic, aromatic or heterocyclic group; $R_3$, $R_5$ and $R_6$ each represents a hydrogen atom, a halogen atom, an aliphatic group, an aromatic group or an acylamino group, $R_3$ may be a non-metal atomic group which can form, together with $R_2$, a 5- or 6-membered ring containing a nitrogen atom; $Y_1$ and $Y_2$ each represents a hydrogen atom or an elimination group which is removed during the coupling reaction thereof with the oxidized form of a developing agent; and n is 0 or 1.

$R_5$ in Formula (C-II) is preferably an aliphatic group such as a methyl, ethyl, propyl, butyl, pentadecyl, tert-butyl, cyclohexyl, cyclohexylmethyl, phenylthiomethyl, dodecyloxyphenyl thiomethyl, butaneamidomethyl or methoxymethyl group.

Preferred examples of the cyan couplers represented by the foregoing general formula (C-1) or (C-11) are as follows; $R_1$ in Formula (C-I) is preferably an aryl or heterocyclic group, more preferably an aryl group which may be substituted with halogen atoms, alkyl groups, alkoxy groups, aryloxy groups, acylamino groups, acyl groups, carbamoyl groups, sulfonamido group, sulfamoyl groups, sulfonyl groups, sulfamido groups, oxycasbonyl groups and/or cyano groups.

When $R_3$ and $R_2$ in Formula (C-I) do not form a ring, $R_2$ preferably represents a substituted or unsubstituted alkyl or aryl group and more preferably an alkyl group substituted with a substituted aryloxy group while $R_3$ is preferably a hydrogen atom.

$R_4$ in Formula (C-II) preferably represents a substituted or unsubstituted alkyl or aryl group and more preferably an alkyl group substituted with a substituted aryloxy group $R_5$ in Formula (C-II) preferably represents an alkyl group having 2 to 15 carbon atoms or a methyl group carrying a substituent having one or more carbon atoms. Examples of such substituents of methyl group preferably an arylthio, alkylthio, acylamino, aryloxy or alkyloxy group.

$R_5$ in Formula (C-II) more preferably represents an alkyl group having 2 to 15 carbon atoms and most preferably an alkyl group having 2 to 4 carbon atoms.

$R_6$ in Formula (C-II) is preferably a hydrogen or halogen atom and in particular a chlorine or fluorine atom. $Y_1$ and $Y_2$ in Formulae (C-I) and (C-II) each preferably represents a hydrogen atom, a halogen atom, an alkoxy group, an aryloxy group, an acyloxy group or a sulfonamido group.

$R_7$ and $R_9$ in Formula (M-I) each represents an aryl group; $R_8$ represents a hydrogen atom, an aliphatic or aromatic acyl group or an aliphatic or aromatic sulfonyl group; $Y_3$ represents a hydrogen atom or an elimination group. Examples of substituents for the aryl group (preferably a phenyl group) represented by $R_7$ and $R_9$ are the same as those acceptable for $R_1$ and if there are two or more substituents, they may be the same or different. $R_8$ preferably represents a hydrogen atom or an aliphatic acyl or sulfonyl group, in particular a hydrogen atom. Preferred $Y_3$ is one which is eliminated at a sulfur, oxygen or nitrogen atom, in articular those eliminated at a sulfur atom such as those disclosed in, for instance, U.S. Pat. NO. 4,351, 897 and International Laid-Open WO88/04795.

Specific examples of the couplers represented by Formulae (C-I), (C-II) and (M-I) will be listed below.

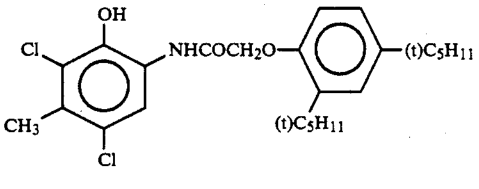

(C-1)

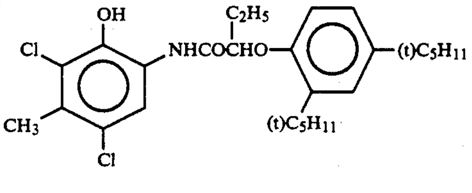

(C-2)

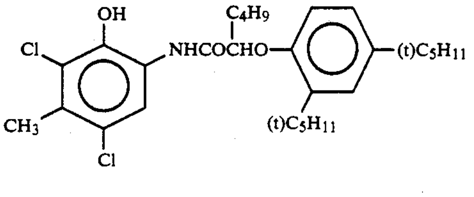

(C-3)

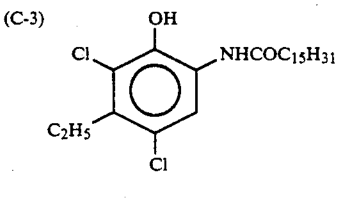

(C-4)

-continued
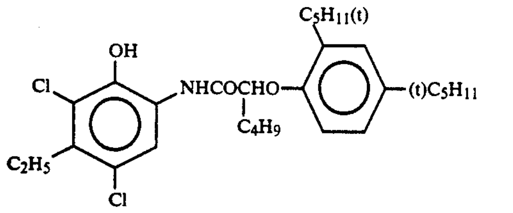
(C-5)
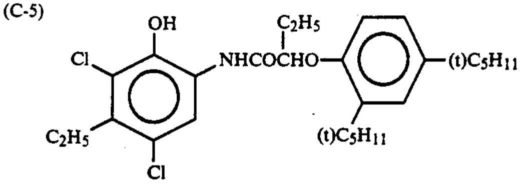
(C-6)
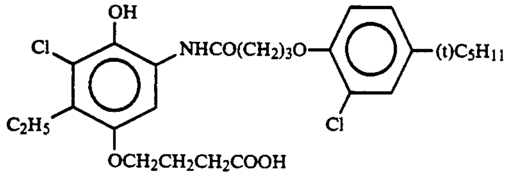
(C-7)
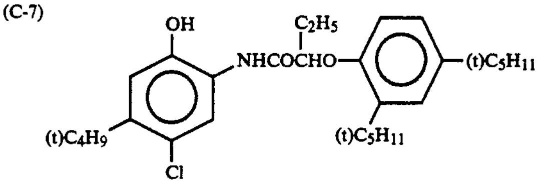
(C-8)
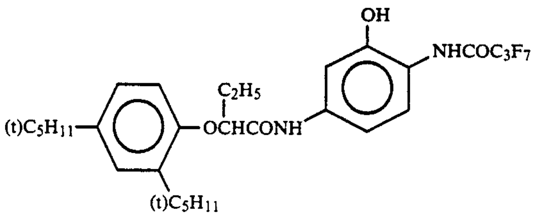
(C-9)
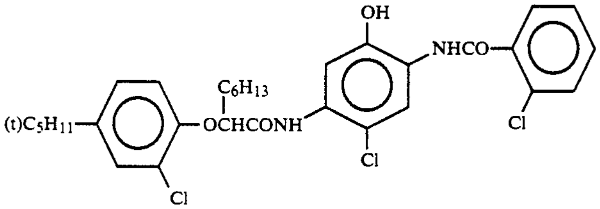
(C-10)
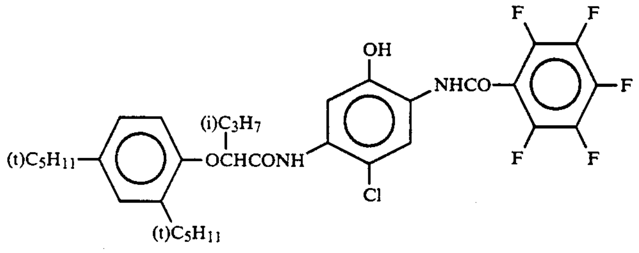
(C-11)
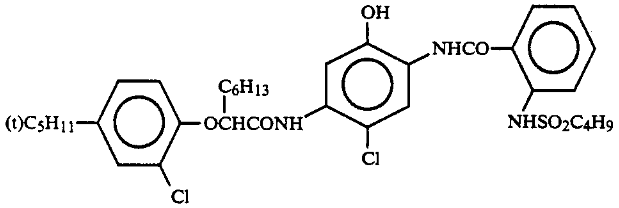
(C-12)
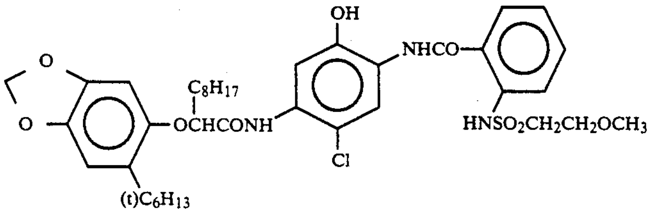
(C-13)

-continued
(C-14)
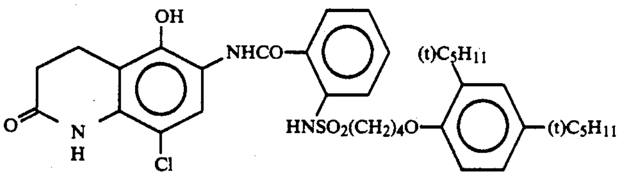
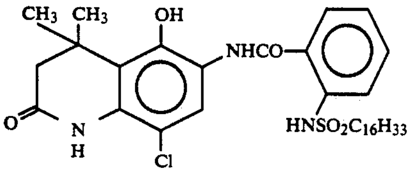
(C-15)
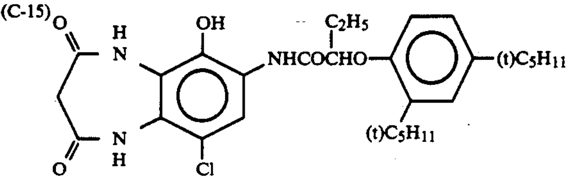
(C-16)
(C-17)
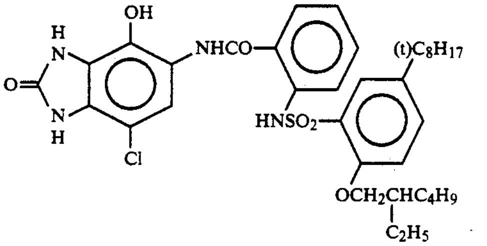
(C-18)
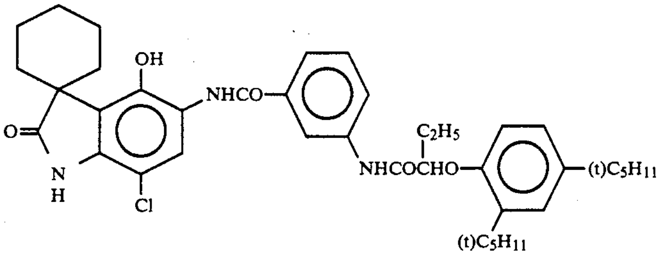
(C-19)
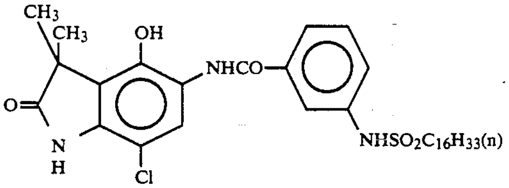
(C-20)
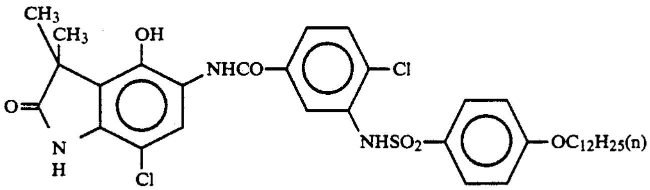
(C-21)
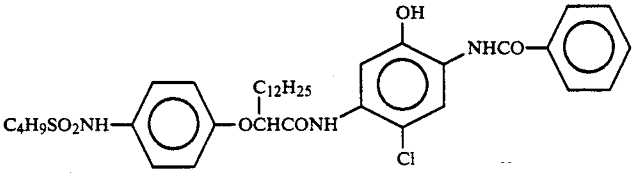

-continued
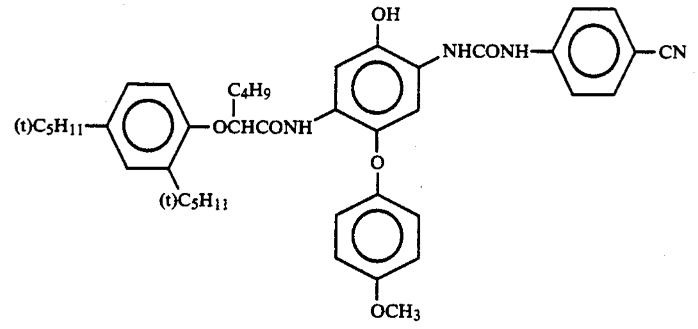
(C-22)
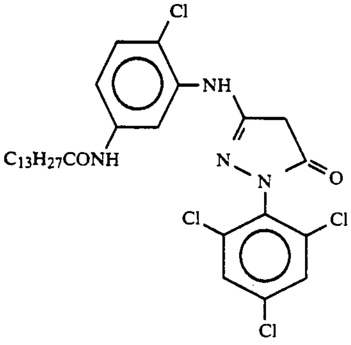
(M-1)
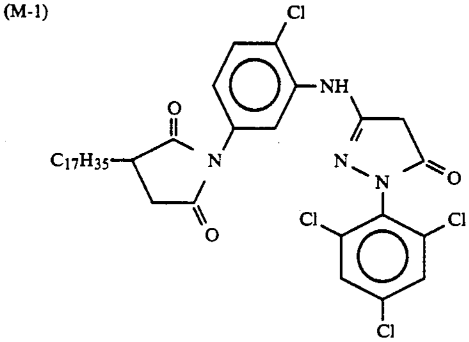
(M-2)
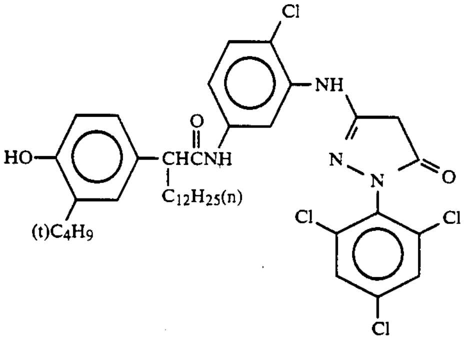
(M-3)
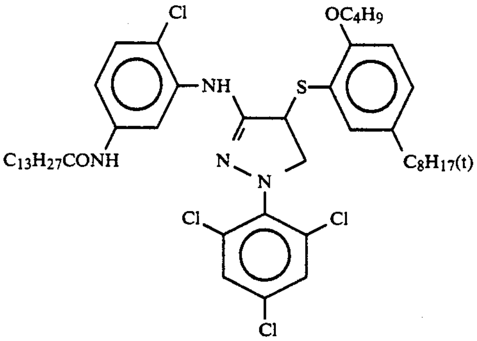
(M-4)
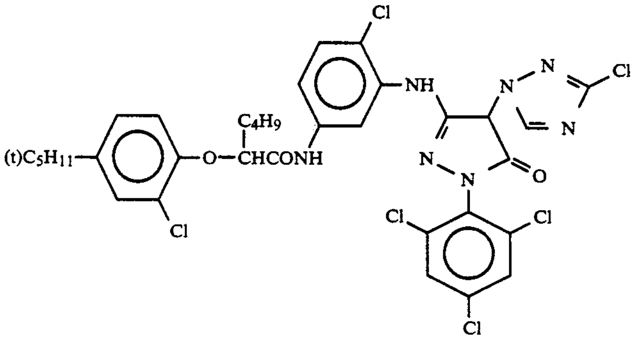
(M-5)

-continued
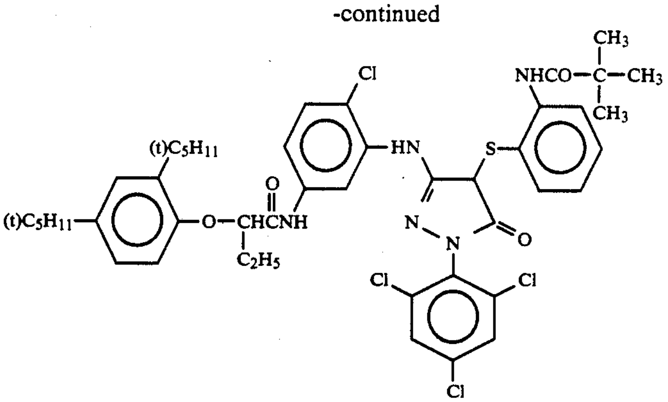
(M-6)
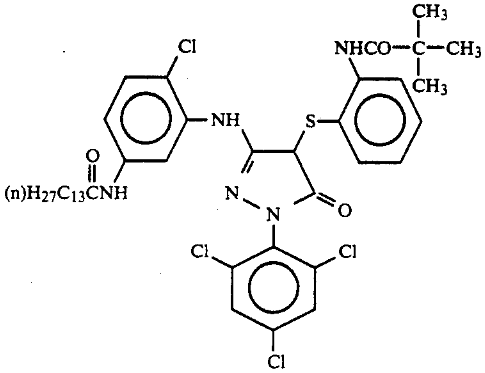
(M-7)
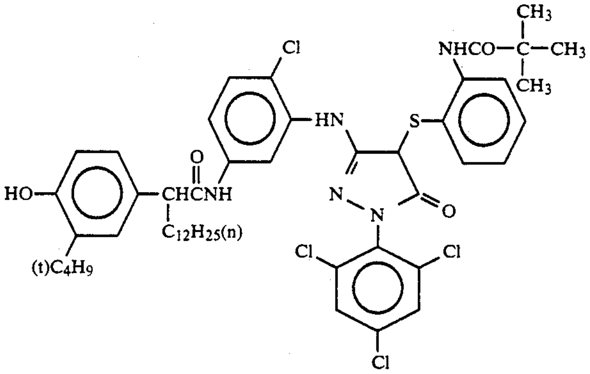
(M-8)
The cyan dye-forming coupler of Formula (II) may be used in combination with phenols and ureides, sulfonamides and carbonamides such as those disclosed in EP Nos. 309,158 A, 309,159 A and 309,160 A, for the purpose of controlling the hue of the couplers. Specific examples of these compounds for controlling the hue are those listed below:
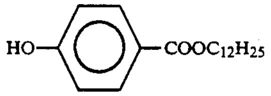
(B-1)
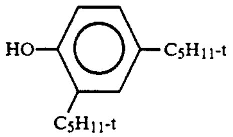
(B-2)
-continued
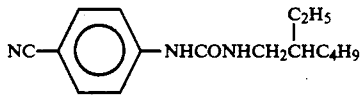
(B-3)
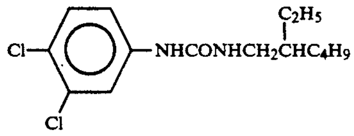
(B-4)
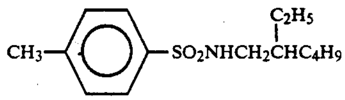
(B-5)
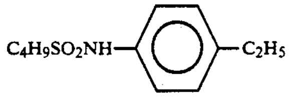
(B-6)

-continued

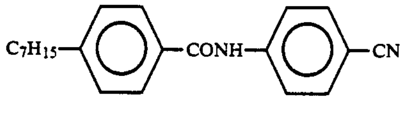
(B-7)

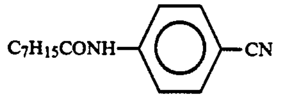
(B-8)

The couplers represented by the foregoing Formulae (II), (Y), (M), (C-I), (C-II) and (M-I) are in general added to the silver halide emulsion from which the light-sensitive layer is formed in an amount ranging from 0.1 to 1.0 mole, preferably 0.1 to 0.5 mole per mole of the silver halide present in the silver halide emulsion.

In the present invention, the couplers may be added to the light-sensitive layer according to various known methods. In general, they can be added to the light-sensitive layer through an oil-in-water dispersion method (usually known as oil protect method), in which the coupler is dissolved in a solvent and then emulsified and dispersed in a gelatin aqueous solution containing a surfactant. Alternatively, water or a gelatin aqueous solution is added to a coupler solution containing a surfactant followed by phase reversal of emulsion to thus give an oil-in-water dispersion.

Moreover, if the coupler is soluble in an alkali, it can be dispersed according to so-called Fisher dispersion method. The coupler dispersion may be mixed with a photographic emulsion after removing the low-boiling organic solvent from the dispersion by a method such as distillation, Noudle water washing or ultrafiltration.

According to the oil in-water dispersion method as disclosed in U.S. Pat. No. 2,322,027, a lipophilic photographic organic compound is dissolved in a high boiling organic solvent having a boiling point at ordinary pressure of about 175° C. or higher and/or a low-boiling organic solvent having a boiling point at ordinary pressure of from about 30° C. to about 160° C. and then emulsified and dispersed in a hydrophilic colloid such as gelatin. Examples of the high-boiling organic solvent are phthalates, phosphates, benzoates, fatty acid esters, amides, phenols, alcohols, carboxylic acids, N,N-dialkylanilines, hydrocarbons, oligomers or polymers; and those of the low-boiling organic solvents are esters such as ethyl acetate, butyl acetate, ethyl propionate, β-ethoxyethyl acetate or methyl cellosolve acetate, alcohols such as secbutyl alcohol, ketones such as methyl isobutyl ketone, methyl ethyl ketone or cyclohexanone, amides such as dimethylformamide or N-methylpyrrolidone and ethers such as tetrahydrofuran or dioxane. The processes and effects of the latex dispersion method as well as specific examples of latexes for impregnation are detailed in, for instance, U.S. Pat. No. 4,199,363; OLS Nos. 2,541,274 and 2,541,230 and European Patent No. 294,104 A. These high-boiling Organic solvents and latexes not only serve as a dispersing agents but also serve to improve physical properties of the gelatin film, to accelerate the color development, to control the hue of the developed color images, to improve the fastness of the color images or the like if the structure thereof is properly selected. The high-boiling organic solvents may be in any form such as liquids, waxes or solids and preferred examples thereof are those represented by the following general formulae (S-1) to (S-9):

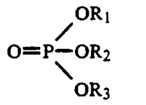
(S-1)

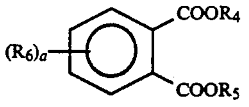
(S-2)

$(Ar-COO)_b-R_7$ (S-3)

$(R_8-COO)_c-R_9$ (S-4)

$R_{10}-(COO-R_{11})_4$ (S-5)

$R_{12}-CON(R_{13})R_{14}$ (S-6)

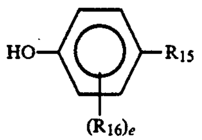
(S-7)

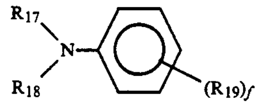
(S-8)

$-(A_1)_{a1}-(A_2)_{a2}-\ldots-(A_a)_{an}-$ (S-9)

In Formula (S-1), $R_1$, $R_2$ and $R_3$ each independently represents an alkyl group, a cycloalkyl group or an aryl group.

In Formula (S-2), $R_4$ and $R_5$ each independently represents an alkyl group, a cycloalkyl group or an aryl group; $R_6$ represents a halogen atom such as F, Cλ, Br or I (the same will apply to the following), an alkyl group, an alkoxy group, an aryloxy group or an alkoxycarbonyl group; and a is an integer ranging from 0 to 3; provided that if a is more than 1, a plurality of $R_6$s may be the same or different.

In Formula (S-3), Ar represents an aryl group; b is an integer ranging from 1 to 6; and $R_7$ represents a hydrocarbon group or that carrying an ether bond having a valency of b.

In Formula (S-4), $R_8$ represents an alkyl group or a cycloalkyl group; C represents an integer ranging from 1 to 6; and $R_9$ represents a hydrocarbon group or that carrying an ether bond having a valency of C.

In Formula (S-5), d is an integer ranging from 2 to 6; $R_{10}$ represents a hydrocarbon group having a valency of d except for an aromatic group; and $R_{11}$ represents an alkyl group, a cycloalkyl group or an aryl group.

In Formula (S-6), $R_{12}$, $R_{13}$ and $R_{14}$ each independently represents an alkyl group, a cycloalkyl group or an aryl group, with the proviso that $R_{12}$ and $R_{13}$, or $R_{13}$ and $R_{14}$ may be bonded together to form a ring.

In Formula (S 7), $R_{15}$ represents an alkyl, cycloalkyl, alkoxycarbonyl, alkylsulfonyl, arylsulfonyl, aryl or cyano group; $R_{16}$ represents a halogen atom or an alkyl, cycloalkyl, aryl, alkoxy or aryloxy group; and e is an integer ranging from 0 to 3, provided that if e is more than 1, a plurality of $R_{16}$s may be the same or different.

In Formula (S-8), $R_{17}$ and $R_{18}$ each independently represents an alkyl group, a cycloalkyl group or an aryl group; $R_{19}$ represents a halogen atom or an alkyl, cycloalkyl, aryl, alkoxy or aryloxy group; and f is an integer ranging from 0 to 4, provided that if f is more than 1, a plurality of $R_{19}$s may be the same or different.

In Formula (S-9), $A_1$, $A_2$, ..., and $A_n$ each represents a repeating unit different from one another, each derived from non-dye-forming ethylenic monomer, $a_1$, $a_2$, ..., and $a_n$ each represents the weight fraction of the corresponding repeating unit; and n is an integer ranging from 1 to 30.

Specific examples of the high-boiling organic solvents are as follows:

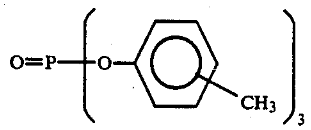
S-1

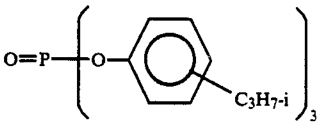
S-2

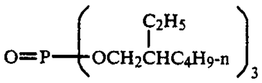
S-3

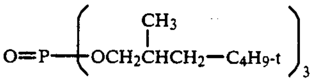
S-4

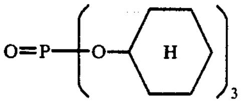
S-5

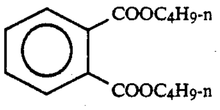
S-6

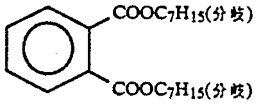
S-7

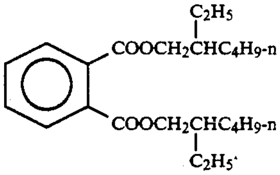
S-8

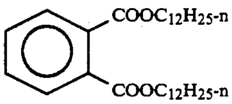
S-9

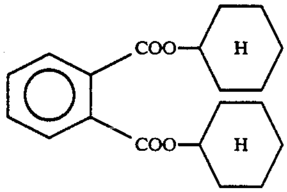
S-10

-continued

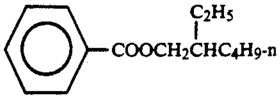
S-11

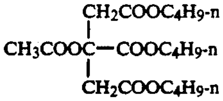
S-12

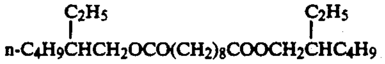
S-13

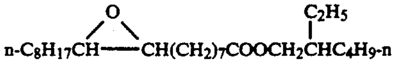
S-14

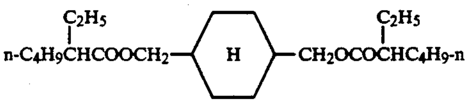
S-15

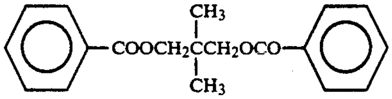
S-16

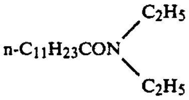
S-17

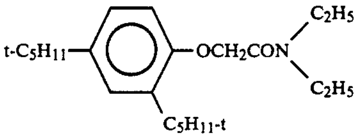
S-18

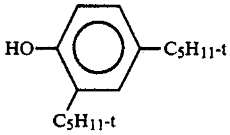
S-19

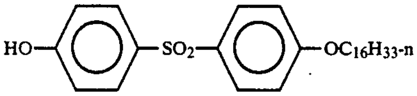
S-20

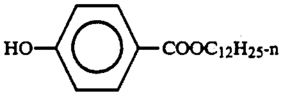
S-21

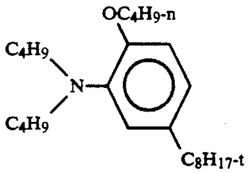
S-22

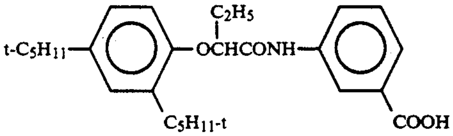
S-23

Polymethyl methacrylate (average molecular S-24

-continued

| | |
|---|---|
| weight = 20,000) | |
| Poly(N-t-butyl acrylamide (average molecular weight = 60,000) | S-25 |
| Chlorinated paraffin (average composition: $C_{12}H_{18}Cl_8$) | S-26 |

Examples of the high-boiling organic solvents other than the foregoing ones and/or methods for preparing these high-boiling organic solvents are disclosed in, for instance, U.S. Pat. Nos. 2,322,027; 2,533,514; 2,772,163; 2,835,579; 3,676,137; 3,912,515; 3,936,303; 4,080,209; 4,127,413; 4,193,802; 4,239,851; 4,278,757; 4,363,873; 4,483,918; and 4,745,049; European Patent No. 276,319 A; J.P. KOKAI Nos. Sho 48-47335, Sho 51-149028, Sho 61-84641, Sho 62-118345, Sho 62-247364, Sho 63-167357, Sho 64-68745 and Hei 1-101543.

In the present invention, a fading inhibitor may be used optionally. The fading inhibitors usable in the invention are, for instance, those represented by the following general formulae (A-I) to (A-IV).

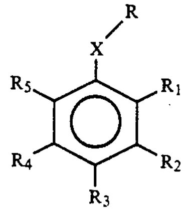
(A-I)

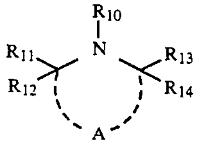
(A-II)

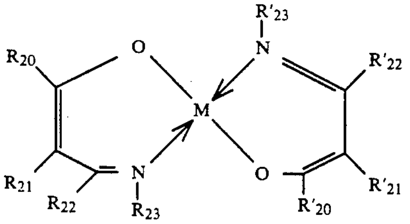
(A-III)

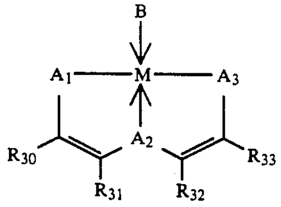
(A-IV)

In the general formulae (A-I) to (A-IV), R represents a hydrogen atom, an alkyl, alkenyl, aryl, heterocyclic, silyl or phosphono group or a protective group which can be eliminated under an alkaline condition; X is —O—, —S— or —N(R')—; R' has the same meaning as that defined above in connection with R; $R_1$ to $R_5$ may be the same or different and each represents a hydrogen atom, —X—R, an alkyl group, an alkenyl group, an aryl group, a heterocyclic group, an alkyloxycarbonyl group, an aryloxycarbonyl group, a halogen atom, an acyl group, a sulfonyl group, a carbamoyl group, a sulfamoyl group, a cyano group, a nitro group, a sulfo group or a carboxyl group; provided that two of —X—R and $R_1$ to $R_5$ which are in ortho-relation in Formula (A-I) may be bonded to form a 5- to 7-membered ring.

$R_{10}$ represents a hydrogen atom, an alkyl group, an alkenyl group, an aryl group, an oxyradical group, a hydroxyl group, an acyl group, a sulfonyl group or a sulfinyl group. $R_{11}$ to $R_{14}$ may be the same or different and each represents a hydrogen atom or an alkyl group. A represents a non-metal atomic group required for forming a 5- to 7-membered ring.

M represents copper, cobalt, nickel, palladium or platinum; $R_{20}$, $R_{21}$, $R_{22}$, $R'_{20}$, $R'_{21}$ and $R'_{22}$ may be the same or different and each represents a hydrogen atom or an alkyl or aryl group; $R_{23}$ and $R'_{23}$ may be the same or different and each represents a hydrogen atom or an alkyl, aryl, hydroxyl, alkoxy or aryloxy group, provided that $R_{23}$ and $R'_{23}$ may be bonded together and that two of $R_{20}$ to $R_{23}$ or two of $R'_{20}$ to $R'_{23}$ which are adjacent to one another may be bonded together to form an aromatic ring or a 5 to 8-membered ring.

$A_1$ and $A_3$ may be the same or different and each represents an oxygen or sulfur atom, a hydroxyl, mercapto, alkoxy or alkyloxy group or a group: $N(R_{34})R_{35}$ group (wherein $R_{34}$ and $R_{35}$ may be the same or different and each represents a hydrogen atom or an alkyl, aryl or hydroxyl group); $A_2$ represents —O—, —S— or —$N(R_{36})$— (wherein $R_{36}$ represents a hydrogen atom or an alkyl or aryl group); $R_{30}$ to $R_{33}$ may be the same or different and each represents a hydrogen atom or an alkyl or aryl group; $R_{30}$ and $R_{31}$, or $R_{32}$ and $R_{33}$ may be bonded together to form an aromatic ring or a 5 to 8 membered ring. B represents a compound which serves as a ligand for M. The coordination number of the compound ranges from 1 to 5.

Among the groups defined in connection with Formulae (A-I) to (A-IV), those containing carbon atoms may further be substituted with substituents.

Among the compounds represented by Formulae (A I) to (A-IV), preferred are those represented by Formulae (A-I) to (A-III). Among the compounds represented by Formula (A-I), preferred are those defined below:

1) those of Formula (A-I) wherein X is —O— and at least one of $R_1$ to $R_5$ is —X—R;
2) those of Formula (A-I) wherein —X—R is —OH and $R_3$ is an aryloxycarbonyl group;
3) those of Formula (A-I) wherein X is —O— and $R_1$ is a substituted benzyl group; and
4) those of Formula (A-I) wherein $R_1$ is an amido group.

Among the compounds represented by Formula (A-II), preferred are those of Formula (A-II) in which A forms a 5 or 6-membered ring and among the compounds represented by Formula (A-III), preferred are those of Formula (A-III) in which M is nickel and $R_{20}$ and $R_{21}$ as well as $R'_{20}$ and $R'_{21}$ form aromatic rings.

Typical examples of the compounds represented by Formulae (A-I) to (A-Iv) will be listed below, but the present invention is not restricted to these specific examples.

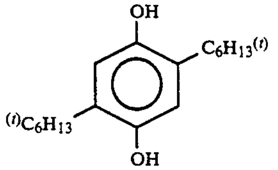
(A-1)

-continued
(A-2)
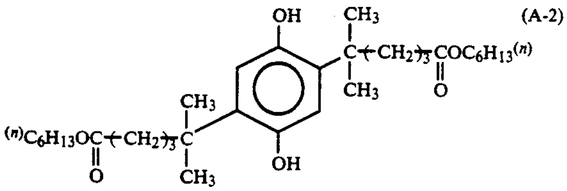
(A-3)
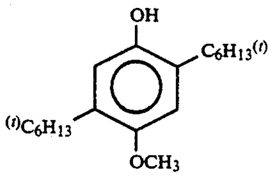
(A-4)
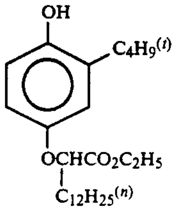
(A-5)
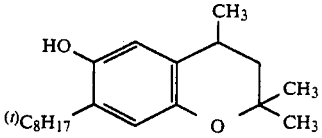
(A-6)
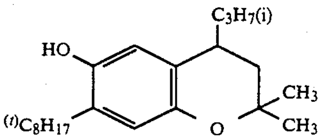
(A-7)
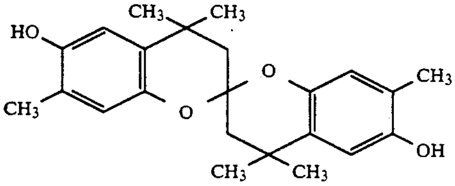
(A-8)
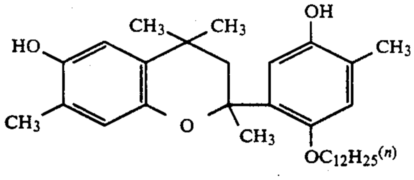
(A-9)
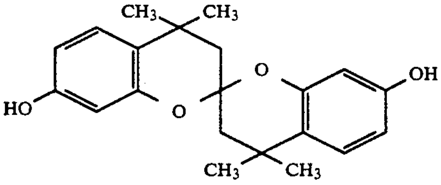
(A-10)
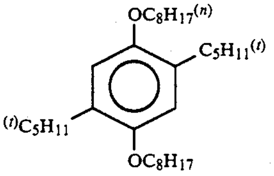
-continued
(A-11)
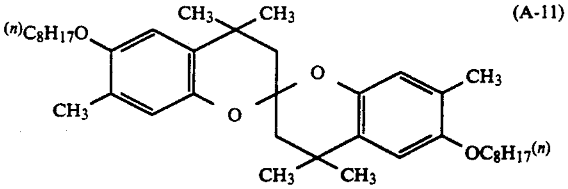
(A-12)
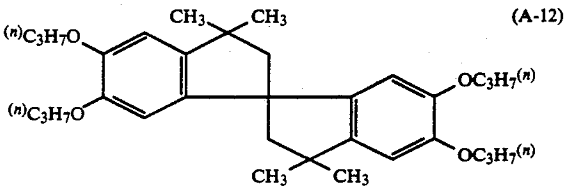
(A-13)
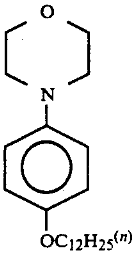
(A-14)
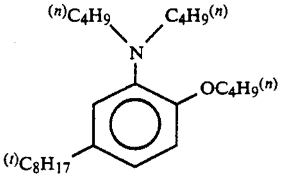
(A-15)
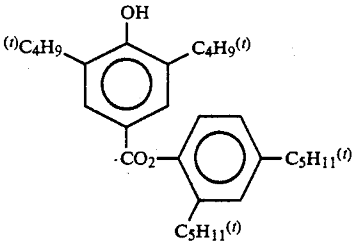
(A-16)
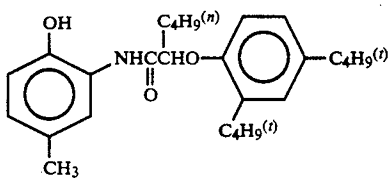
(A-17)
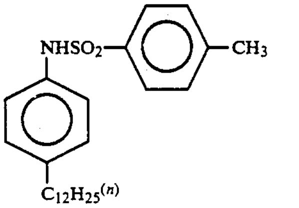

-continued (A-18)

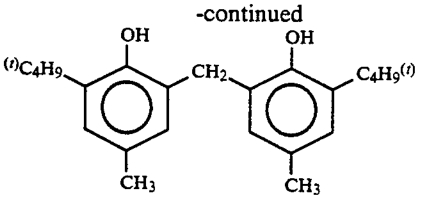

(A-19)

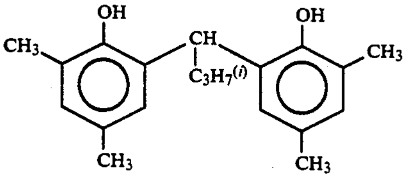

(A-20)

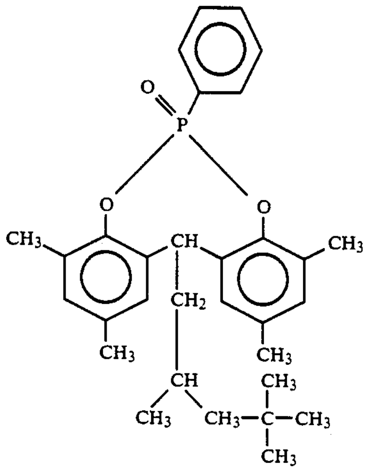

(A-21)

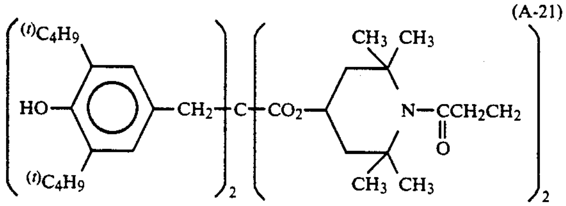

(A-22)

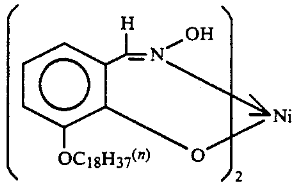

(A-23)

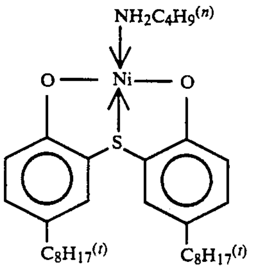

Preferred examples of the compounds represented by Formulae (A-I) to (A-Iv) and methods for preparing the same are, for instance, disclosed in U.S. Pat, Nos. 2,735,765; 3,432,300; 3,573,050; 3,574,627; 3,698,909; 3,700,455; 3,764,337; 3,930,866; 3,982,944; 4,113,495; 4,120,723; 4,155,765; 4,254,216; 4,245,018; 4,268,593; 4,273,864; 4,279,990; 4,332,836; 4,360,589; 4,430,425; 4,483,918; 4,540,653; 4,559,297; 4,745,050; and 4,749,645; U.K. Patent Nos. 1,156,167; 2,039,068; 2,043,931 and 2,066,975; European Patent Laid-Open Nos. 98,241; 176,845; 178,165; 264,730; 268,496; 273,412; and 298,321; J.P. KOKOKU No. Sho 60-24455; and J.P. KOKAI Nos. Sho 59-87456, Sho 61-258246 and Sho 63-95440.

The amount of the compound represented by Formulae (A I) to (A-IV) varies depending on the kinds of couplers used in combination therewith, but in general ranges from $1\times10^{-2}$ to 10 moles, preferably $3\times10^{-2}$ to 5 moles per mole of the coupler used. This is because if it is less than the lower limit, it is difficult to achieve the intended effects of the invention, while if it exceeds the upper limit, for instance, the color developing reaction is impaired.

The silver halide color photographic light-sensitive materials containing the coupler of Formula (II), substrates usable, development processings or the like are the same as those described above in connection with the silver halide color photographic light-sensitive materials containing the coupler of Formula (I).

As has been explained above in detail, the present invention can provide color images excellent in the color reproduction of yellow, magenta and cyan and the fastness of the cyan color images and having low fogging of cyan.

The present invention will hereunder be explained in more detail with reference to the following non-limitative working Examples and Reference Examples and the effects practically attained by the present inventlon will also be discussed in comparison with Comparative Examples given below.

REFERENCE EXAMPLE 1

2.0 g of Coupler (1) of the present invention was dissolved in 20 ml of ethyl acetate and 15 ml of ethanol. A solution of 3 g of sodium carbonate in 30 ml of water was added thereto. 2.4 g of 4-(ethyl-methanesulfonamidoethylamino)-o-toluidine monohydrate sesquisulfate was added to the mixture under stirring. A solution of 2.7 g of ammonium persulfate in 16 ml of water was added dropwise thereto. The mixture was stirred at room temperature for 30 min. 100 ml of water was added to the mixture to divide it into layers. The ethyl acetate layer was washed with water three times and, dried over anhydrous sodium sulfate. The solvent was distilled off at ambient temperature under reduced pressure. The residue was dissolved in a small amount of chloroform immediately thereafter and the solution was passed through a silica gel column to take a fraction of cyan color. The solvent was distilled off at ambient temperature under reduced pressure to obtain a powdery navy blue dye.

For comparison, dyes were produced from Couplers (2) and (5) and Comparative Couplers (C-1) and (C-2) which will be shown below in the same manner as above.

The absorption spectrum of each dye solution is shown in Table 1. The spectra of Coupler (1) and Comparative Coupler (C-1) are shown in FIG. 1.

| Coupler used | Maximum absorption (nm) | Half band width (nm) | ε |
|---|---|---|---|
| Coupler (1) of the | 620.8 | 80.4 | 58600 |

-continued

| Coupler used | Maximum absorption (nm) | Half band width (nm) | ε |
|---|---|---|---|
| present invention | | | |
| Coupler (2) of the present invention | 620.6 | 80.3 | 58400 |
| Coupler (5) of the present invention | 620.1 | 81.2 | 54600 |
| Comparative Coupler (C-1) | 622.4 | 114.7 | 29400 |
| Comparative Coupler (C-2) | 621.0 | 116.2 | 20800 |

It is apparent from FIG. 1 and Table 1 that the absorption of the dye obtained from the coupler of the present invention was quite sharp and had a vivid hue and a high molar extinction coefficient (ε).

Comparative Coupler (C-1)

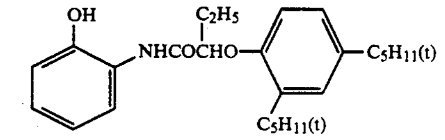

Comparative Coupler (C-2)

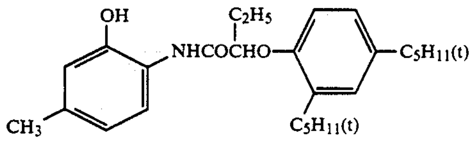

EXAMPLE 1

A solution prepared by heating 10 g of Coupler (1) of the present invention, 10 g of dibutyl phthalate and 20 ml of ethyl acetate at 50° C. was dispersed in 80 g of gelatin solution containing 8 ml of 1% aqueous sodium dodecylbenzenesulfonate solution to form an emulsion.

Then the emulsion was mixed with 145 g (7 g in terms of Ag) of a red-sensitive silver chlorobromide emulsion (Br content: 50%). Sodium dodecylbenzenesulfonate as the coating aid was added thereto and the mixture was applied to the surface of a paper substrate the both surface of which had been laminated with polyethylene films. The amount of the coupler to be coated was 400 $mg/m^2$. A protective gelatin layer (gelatin: 1 $g/m^2$) was formed thereon to form Sample A.

The same procedure as above was repeated except that Coupler (1) was replaced with an equimolar amount of Coupler (2), (3), (5), (16), (17) or (26) to form Samples B to G, respectively. For comparison, Samples H to L were prepared in the same manner as above except that Comparative Couplers (C-1), (C-2), (C-3), (C-4) and (C-5) were used, respectively.

The samples were exposed with a sensitometric continuous wedge and then subjected to the following developing .treatment:

Color development step (33° C.)

1. Color development (3 min 30 sec)
2. Bleach-fixing (1 min 30 sec)
3. Washing with water (2 min 30 sec)

The treating solutions used in the respective steps were as follows:

| | |
|---|---|
| Color developer: | |
| benzyl alcohol | 15.0 ml |
| diethylene glycol | 8.0 ml |
| ethylenediaminetetraacetic acid | 5.0 g |
| sodium sulfite | 2.0 g |
| anhydrous potassium carbonate | 30 g |
| hydroxylamine sulfate | 3.0 g |
| potassium bromide | 0.6 g |
| 4-amino-N-ethyl-N-(β-methanesulfonamidoethyl)-m-toluidine sesquisulfate monohydrate | 5.0 g |
| water | ad 1 l (pH 10.2) |

Comparative Couplers:

(C-3)

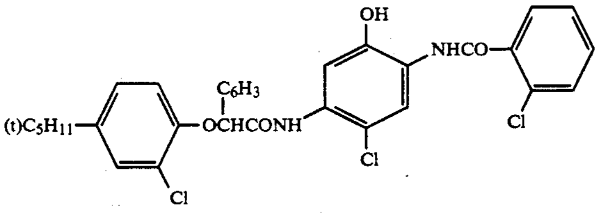

(C-4)

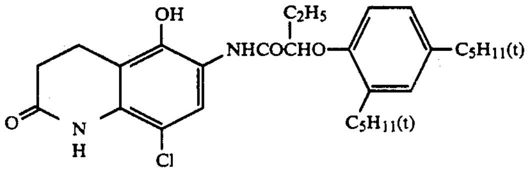

(C-5)

-continued

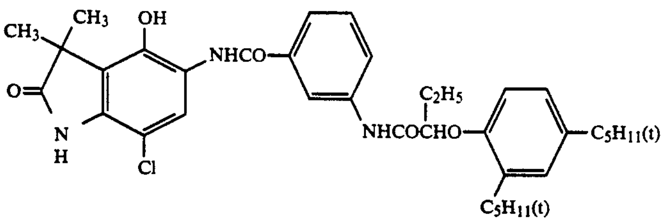

| Bleach-fixing solution: | |
|---|---|
| ethylenediaminetetraacetic acid | 4.0 g |
| ferric ethylenediaminetetraacetate | 40 g |
| sodium sulfite | 5.0 g |
| (70%) sodium thiosulfate | 150 ml |
| water | ad 1 liter |

Samples treated with the couplers of the present invention had a vivid cyan or blue hue.

Then the fastness of the treated samples was examined. Dye densities kept after leaving the samples to stand at a dark place at 100° C. for 10 days or after exposing them to a light with a xenon fadeometer (100,000 1x) are shown in Table 2.

TABLE 2

| Sample No. | Coupler | 100° C., 10 days | Xenon, 1 week | Remarks |
|---|---|---|---|---|
| A | 1 | 0.32 | 0.50 | present invention |
| B | 2 | 0.33 | 0.52 | " |
| C | 3 | 0.80 | 0.68 | " |
| D | 5 | 0.48 | 0.56 | " |
| E | 16 | 0.89 | 0.72 | " |
| F | 17 | 0.91 | 0.89 | " |
| G | 26 | 0.88 | 0.90 | " |
| H | C-1 | 0.38 | 0.48 | comparative example |
| I | C-2 | 0.40 | 0.78 | " |
| J | C-3 | 0.85 | 0.69 | " |
| K | C-4 | 0.88 | 0.86 | " |

TABLE 2-continued

| Sample No. | Coupler | 100° C., 10 days | Xenon, 1 week | Remarks |
|---|---|---|---|---|
| L | C-5 | 0.82 | 0.88 | " |

It is apparent from Table 2 that the couplers of the present invention had the fastness similar to that of corresponding couplers having a carbon ring (comparison of A with B and H, D with I, E with J, F with K and G with L).

EXAMPLE 2

A multilayer silver halide photosensitive material 101 having the following layer structure formed on a paper substrate the both surface of which had been laminated with polyethylene was prepared:

Sodium salts of 1-oxy-3,5-dichloro-s-triazine was used in each layers as a gelatin hardener.

The following compounds were used as spectral sensitizing dye:

Blue-sensitive emulsion layer

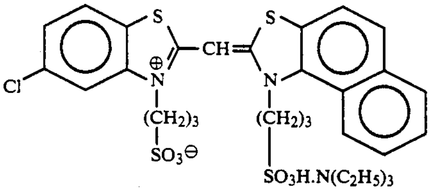

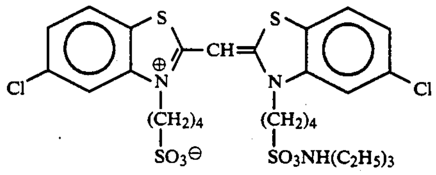

(Large size emulsion: $2.0 \times 10^{-4}$ mole/l mole silver halide
Small size emulsion: $2.5 \times 10^{-4}$ mole/l mole silver halide)

Green-sensitive emulsion layer

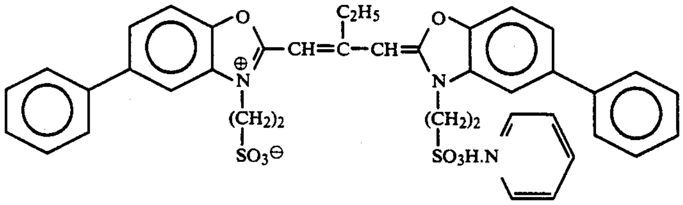

(Large size emulsion: $4.0 \times 10^{-4}$ mole/l mole silver halide
Small size emulsion: $5.6 \times 10^{-4}$ mole/l mole silver halide)

and

-continued

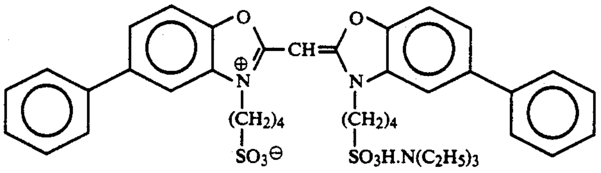

(Large size emulsion: 7.0 × $10^{-4}$ mole/l mole silver halide
Small size emulsion: 1.0 × $10^{-4}$ mole/l mole silver halide)

Red-sensitive emulsion layer

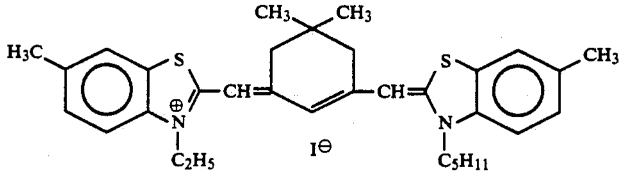

(Large size emulsion: 0.9 × $10^{-4}$ mole/l mole silver halide
Small size emulsion: 1.1 × $10^{-4}$ mole/l mole silver halide)

$2.6 \times 10^{-3}$ mole/l mole silver halide of the following compound was added to the red-sensitive emulsion layer.

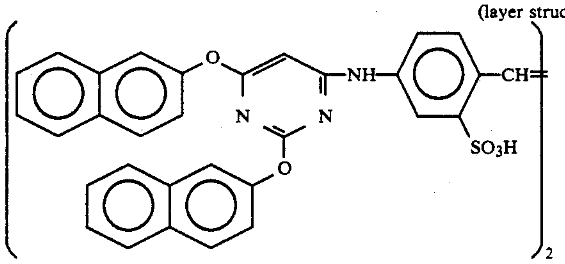

$8.5 \times 10^{-5}$, $7.7 \times 10^{-4}$ and $2.5 \times 10^{-3}$ (mole/l mole silver halide) of 1-(5-methylureidophenyl)-5-mercaptotetrazale were added to the blue-sensitive, green-sensitive and red-sensitive emulsion layers, respectively.

The following dyes were added to emulsion layers in order for inhibition of irradiation.

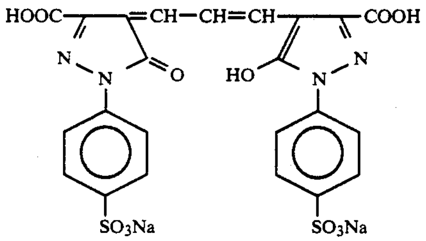

and

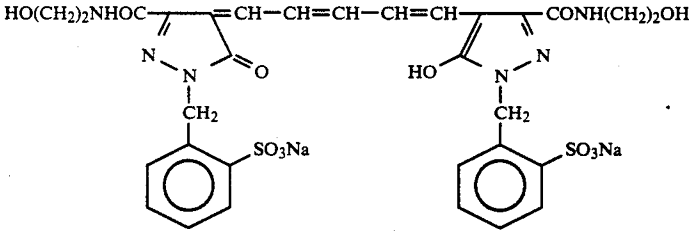

(layer structure)

The compositions of the respective layers will be shown below. The numerals stands for the applied amount (g/m²). The amount of the silver halide emulsion is given in terms of silver.

Support:

paper laminated with polyethylene (The polyethylene layer adjacent to the first layer contained a white pigment ($TiO_2$) and a blue dye:)

-continued

| | |
|---|---|
| The first layer (blue-sensitive layer) | |
| silver chlorobromide emulsion | 0.30 |
| gelatin | 1.86 |
| yellow coupler (ExY) | 0.82 |
| color image stabilizer (Cpd-1) | 0.19 |
| solvent (Solv-3) | 0.35 |
| color image stabilizer (Cpd-7) | 0.06 |
| The second layer (color mixing-inhibiting layer) | |
| gelatin | 0.99 |
| color mixing inhibitor (Cpd-5) | 0.08 |
| solvent (Solv-1) | 0.16 |
| solvent (Solv-4) | 0.08 |
| The third layer (green-sensitive layer) | |
| silver chlorobromide emulsion | 0.12 |
| (1:3 (Ag molar ratio) mixture of cubic grains with 0.55 μm and 0.39 μm of an average particle size. Degrees of variability of particle size distribution were 0.10 and 0.08. 0.8 mol. % of AgBr localized on the grain surface.) | |
| gelatin | 1.24 |
| magenta coupler (ExM) | 0.20 |
| color image stabilizer (Cpd-3) | 0.15 |
| color image stabilizer (Cpd-4) | 0.02 |
| color image stabilizer (Cpd-2) | 0.03 |
| solvent (Solv-2) | 0.40 |
| The fourth layer (U.V. absorption layer) | |
| gelatin | 1.58 |
| U.V. absorber (UV-1) | 0.47 |
| color mixing inhibitor (Cpd-5) | 0.05 |
| solvent (Solv-5) | 0.24 |
| The fifth layer (red-sensitive layer) | |
| silver chlorobromide emulsion | 0.23 |
| (1:4 (Ag molar ratio) mixture of cubic grains with 0.58 μm and 0.45 μm of an average particle size. Degrees of variability of particle size distribution were 0.09 and 0.11. 0.6 mol. % of AgBr localized on a part of the grain surface.) | |
| gelatin | 1.34 |
| cyan coupler (C-1) | 0.15 |
| cyan coupler (C-2) | 0.18 |
| color image stabilizer (Cpd-6) | 0.02 |
| color image stabilizer (Cpd-8) | 0.04 |
| color image stabilizer (Cpd-7) | 0.40 |
| solvent (Solv-6) | 0.15 |
| The sixth layer (U.V. absorption layer) | |
| gelatin | 0.53 |
| U.V. absorber (UV-1) | 0.16 |
| color mixing inhibitor (Cpd-5) | 0.02 |
| solvent (Solv-5) | 0.08 |
| The seventh layer (protective layer) | |
| acid-treated gelatin | 1.33 |
| acrylic-modified polyvinyl alcohol copolymer (degree of modofication: 17%) | 0.17 |
| liquid paraffin | 0.03 |

(ExY) Yellow coupler
1:1 (molar ratio) mixture of

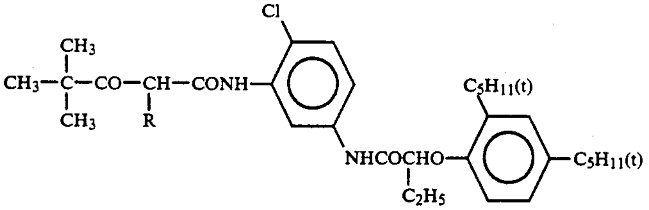

R = 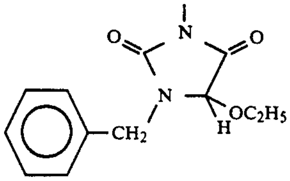 and R = 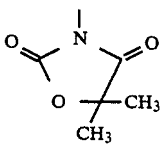

(ExM) Magenta coupler
1:1 (molar ratio) mixture of

-continued
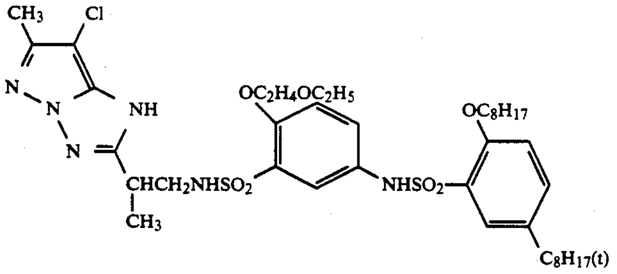
and
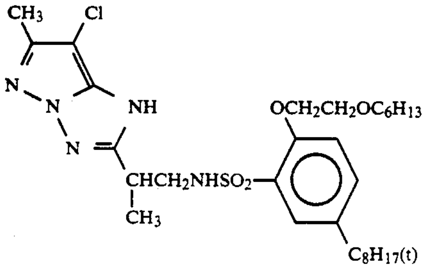
(Cpd-1) color image stabilizer
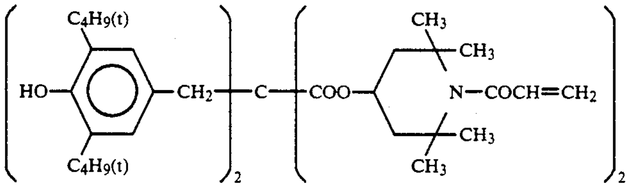
(Cpd-3) color image stabilizer
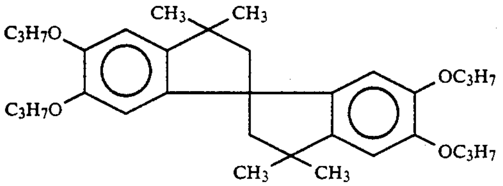
(Cpd-5) color mixing inhibitor
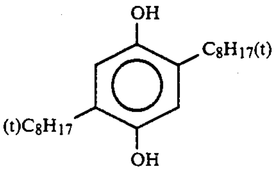
(Cpd-4) color image stabilizer
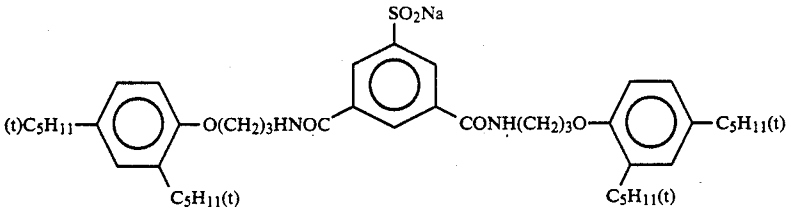
(Cpd-2) color image stabilizer
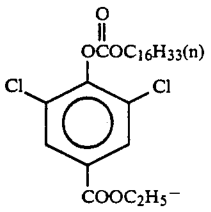
(Cpd-6) color image stabilizer
2:4:4 (weight ratio) mixture of -continued
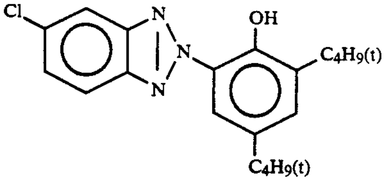
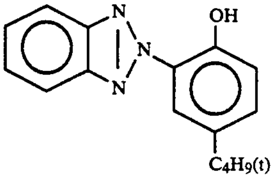
and
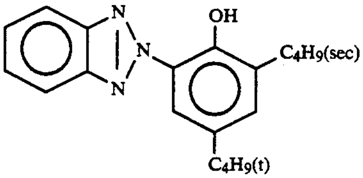
(Cpd-7) color image stabilizer
$-(CH_2-CH)_n-$
$CONHC_4H_9(n)$
Average molecular weight 60,000
(Cpd-8) color image stabilizer
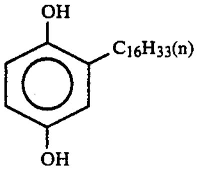
(UV-1) U.V. absorber
4:2:4 (weight ratio) mixture of
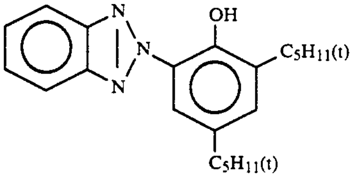
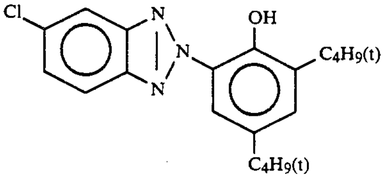
and
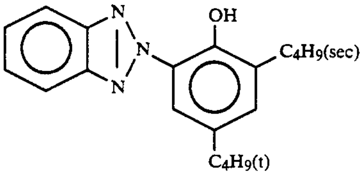
(Solv-1) Solvent
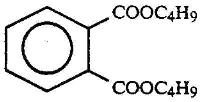
(Solv-2) Solvent
2:1 (volume ratio) mixture
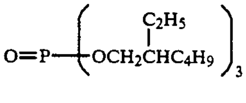
and
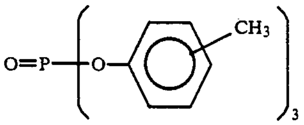
(Solv-3) Solvent
$O=P-(O-C_9H_{19}(iso))_3$
(Solv-4) Solvent
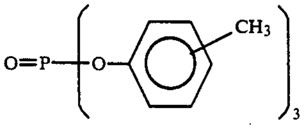
(Solv-5) Solvent
(Solv-6) Solvent -continued

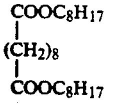

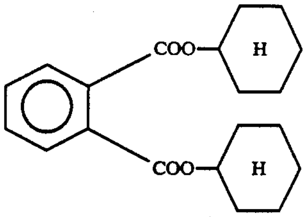

SAMPLES 102 TO 108

Samples were prepared in the same manner as that of the preparation of Sample 101 except that Couplers (C-1) and (C-2) in the fifth layer of Sample 101 (Comparative) were replaced with an equimolar amount of (1), (5), (6), (9), (16), (17) or (26). They will be referred to as Samples 102 to 108, respectively, (present invention.

The photosensitive materials were exposed through an optical wedge and then treated in the following steps:

| Treatment steps | Temperature | Time | Replenisher* | Tank volume |
|---|---|---|---|---|
| Color development | 35° C. | 45 sec | 161 ml | 17 l |
| Bleach-fixing | 30 to 35° C. | 45 sec | 215 ml | 17 l |
| Rinse (1) | 30 to 35° C. | 20 sec | — | 10 l |
| Rinse (2) | 30 to 35° C. | 20 sec | — | 10 l |
| Rinse (3) | 30 to 35° C. | 20 sec | 350 ml | 10 l |
| Drying | 70 to 80° C. | 60 sec | | |

*Amount of replenisher are expressed on the basis of 1 $m^3$ of photosensitive material. (The countercurrent system was employed in the three tanks in the rinse steps (1) to (3).)

The compositions of the treating solutions were as follows:

| Color developer | Tank liquid | Replenisher |
|---|---|---|
| water | 800 ml | 800 ml |
| ethylenediamine-N,N,N,N-tetramethylenephosphoric acid | 1.5 g | 2.0 g |
| triethanolamine | 8.0 g | 12.0 g |
| sodium chloride | 1.4 g | — |
| potassium carbonate | 25 g | 25 g |
| N-ethyl-N-(β-methane-sulfonamidoethyl)-3-methyl-4-aminoaniline sulfate | 5.0 g | 7.0 g |
| N,N-bis(carboxymethyl)hydrazine | 5.5 g | 7.0 g |
| fluorescent brightening agent (WHITEX 4B manufactured by Sumitomo Chemical) | 1.0 g | 2.0 g |
| water | ad 1,000 ml | |
| pH (25° C.) | 10.05 | 10.45 |

Bleach-fixing solution (Tank liquid has the same compostion as that of replenisher)

| | |
|---|---|
| water | 400 ml |
| ammonium thiosulfate (70%) | 100 ml |
| sodium sulfite | 17 g |
| iron (III) ammonium ethylene-diaminetetraacetate | 55 g |
| disodium ethylene-diaminetetraacetate | 5 g |
| ammonium bromide | 40 g |
| water | ad 1,000 ml |
| pH (25° C.) | 6.0 |

RINSE SOLUTION

Ion-exchanged water (Ca, Mg: 3 ppm or less) Samples 102 to 108 prepared by using the couplers of the present invention had a color reproducibility superior to that of Comparative Sample 101.

EXAMPLE 3

The first layer to the fourteenth layer were coated on front side of a paper substrate (thickness: 100μ) (polyethylene has been laminated on the both surfaces of the substrate and the fifteenth layer and the sixteenth layer were coated on the back side of the paper support to form a color photographic photosensitive material sample 201. The polyethylene layer laminated on the front side contained titanium dioxide (4 $g/m^2$) as a white pigment and a small amount of ultramarine (0.003 $g/m^2$) as a bluing dye. (Chromaticity ($L^*$, $a^*$, $b^*$) on the front side of the laminated paper substrate: 88.0, −0.20, −0.75)

PHOTOSENSITIVE LAYER COMPOSITION

The compositions and the applied amount ($g/m^2$) of respective layers will be shown below. Emulsions utilized to each layer were prepared on the basis of the method for reparation of emulsion EMl expect that a lippmann emulsion which had not been subjected to surface chemical sensitization was used as an emulsion of the fourteenth layer.

| | |
|---|---|
| The first layer (anti-halation layer) | |
| black colloidal silver | 0.10 |
| gelatin | 0.70 |
| The second layer (interlayer) | |
| gelatin | 0.70 |
| The third layer (low speed red-sensitive layer) | |
| silver bromide (mean particle size: 0.25μ, size distribution (degree of variability 8%, octahedron) spectrally sensitized with red sensitizing dyes (ExS-1,2,3) | 0.04 |
| silver chlorobromide (silver chloride content: 5 mol. %, mean particle size: 0.40μ, size distribution: 10%, octahedron) spectrally sensitized with red sensitizing dyes (ExS-1,2,3) | 0.08 |
| gelatin | 1.00 |
| cyan coupler (ExC-1:ExC-2:ExC-3 = 1:1:0.2) | 0.30 |
| decoloration inhibitor (Cpd-1:Cpd-2:Cpd-3:Cpd4 = 1:1:1:1) | 0.18 |
| stain inhibitor (Cpd-5) | 0.003 |
| coupler dispersing medium (Cpd-6) | 0.03 |
| solvent for coupler (Solv-1:Solv-2:Solv-3 = 1:1:1) | 0.12 |
| The fourth layer (high speed red-sensitive layer) | |
| silver bromide (mean particle size: 0.60μ, size distribution: 15%, octahedron) spectrally sensitized with red sensitizing dyes (ExS-1,2,3) | 0.14 |
| gelatin | 1.00 |
| cyan coupler (ExC-1:ExC-2 ExC-3 = 1:1:0.2) | 0.30 |
| decoloration inhibitor (Cpd-1:Cpd-2:Cpd-3:Cpd4 = 1:1:1:1) | 0.18 |
| coupler dispersing medium (Cpd-6) | 0.03 |

-continued

| | |
|---|---|
| solvent for coupler (Solv-1:Solv-2:Solv-3 = 1:1:1) | 0.12 |
| The fifth layer (interlayer) | |
| gelatin | 1.00 |
| color mixing inhibitor (Cpd-7) | 0.08 |
| solvent for color mixing inhibitor (Solv-4:Solv-5 = 1:1) | 0.16 |
| polymer latex (Cpd-8) | 0.10 |
| The sixth layer (low speed green-sensitive layer) | |
| silver bromide (mean particle size: 0.25μ, size distribution 8%, octahedron) spectrally sensitized with green sensitizing dye (ExS-4) | 0.04 |
| silver chlorobromide (silver chloride content: 5 mol. %, mean particle size: 0.04μ, size distribution: 10%, octahedron) spectrally sensitized with green sensitizing dye (ExS-4) | 0.06 |
| gelatin | 0.80 |
| magenta coupler (ExM-1:ExM-2:ExM-3 = 1:1:1) | 0.11 |
| decoloration inhibitor (Cpd-9:Cpd-26 = 1:1) | 0.15 |
| stain inhibitor (Cpd-10:Cpd-11:Cpd-12:Cpd-13 = 10:7:7:1) | 0.025 |
| coupler dispersing medium (Cpd-6) | 0.05 |
| solvent for coupler (Solv-4:Solv-6 = 1:1) | 0.15 |
| The seventh layer (high speed green-sensitive layer) | |
| silver bromide (mean particle size: 0.65μ, size distribution: 6%, octahedron) spectrally sensitized with green sensitizing dye (ExS-4) | 0.10 |
| gelatin | 0.80 |
| magenta coupler (ExM-1:ExM-2:ExM-3 = 1:1:1) | 0.11 |
| decoloration inhibitor (Cpd-9:Cpd-26 = 1:1) | 0.15 |
| stain inhibitor (Cpd-10:Cpd-11:Cpd-12:Cpd-13 = 10:7:7:1) | 0.025 |
| coupler dispersing medium (Cpd-6) | 0.05 |
| solvent for coupler (Solv-4:Solv-6 = 1:1) | 0.15 |
| The eighth layer (interlayer) | |
| same as those of the fifth layer | |
| The ninth layer (yellow filter layer) | |
| yellow colloidal silver (particle size: 100 Å) | 0.12 |
| gelatin | 0.70 |
| color mixing inhibitor (Cpd-7) | 0.03 |
| solvent for color mixing inhibitor (Solv-4:Solv-5 = 1:1) | 0.10 |
| polymer latex (Cpd-8) | 0.07 |
| The tenth layer (interlayer) | |
| same as those of the fifth layer | |
| The eleventh layer (low speed blue-sensitive layer) | |
| silver bromide (mean particle size: 0.40μ, size distribution 8%, octahedron) spectrally sensitized with blue sensitizing dye (ExS-5,6) | 0.07 |
| silver chlorobromide (silver chloride content: 8 mol. %, mean particle size: 0.60μ, size distribution: 11%, octahedron) spectrally sensitized with blue sensitizing dye (ExS-5,6) | 0.14 |
| gelatin | 0.80 |
| yellow coupler (ExY-1:ExY-2 = 1:1) | 0.35 |
| decoloration inhibitor (Cpd-14) | 0.10 |
| stain inhibitor (Cpd-5:Cpd-15 = 1:5) | 0.007 |
| coupler dispersing medium (Cpd-6) | 0.05 |
| solvent for coupler (Solv-2) | 0.10 |
| The twelfth layer (high speed blue-sensitive layer) | |
| silver bromide (mean particle size: 0.85μ, size distribution 8%, octahedron) spectrally sensitized with blue sensitizing dyes (ExS-5,6) | 0.15 |
| gelatin | 0.60 |
| yellow coupler (ExY-1:ExY-2 = 1:1) | 0.30 |
| decoloration inhibitor (Cpd-14) | 0.10 |
| stain inhibitor (Cpd-5:Cpd-15 = 1:5) | 0.007 |
| coupler dispersing medium (Cpd-6) | 0.05 |
| solvent for coupler (Solv-2) | 0.10 |
| The thirteenth layer (U.V. absorption layer) | |
| gelatin | 1.00 |
| U.V. absorber (Cpd-2:Cpd-4:Cpd-16 = 1:1:1) | 0.50 |
| color mixing inhibitor (Cpd-7:Cpd-17 = 1:1) | 0.03 |
| dispersing medium (Cpd-6) | 0.02 |
| solvent for U.V. absorber (Solv-2:Solv-7 = 1:1) | 0.08 |
| irradiation inhibiting dye (Cpd-18:Cpd-19:Cpd-20:Cpd-21:Cpd-27 = 10:10:13:15:20) | 0.05 |
| The fourteenth layer (protective layer) | |
| silver chlorobromide fine particles (silver chloride: 97 mol. %, mean particle size: 0.1μ | 0.03 |
| acrylic-modified polyvinyl alcohol copolymer (molecular weight: 50,000) | 0.01 |
| polymethyl methacrylate particles (mean particle size: 2.4μ): silica (mean particle size: 5μ) = 1:1 | 0.05 |
| gelatin | 1.80 |
| gelatin hardener (H-1:H-2 = 1:1) | 0.18 |
| The fifteenth layer (back layer) | |
| gelatin | 2.50 |
| U.V. absorber (Cpd-2:Cpd-4:Cpd-16 = 1:1:1) | 0.50 |
| dye (Cpd-18:Cpd-19:Cpd-20:Cpd-21:Cpd-27 = 1:1:1:1:1) | 0.06 |
| The sixteenth layer (back side protective layer) | |
| polymethyl methacrylate particles (mean particle size: 2.4μ): silica (mean particle size: 5μ) = 1:1 | 0.05 |
| gelatin | 2.00 |
| gelatin hardener (H-1:H-2 = 1:1) | 0.14 |

PREPARATION METHOD OF EMULSION EM-1

An aqueous potassium bromide solution and an aqueous silver nitrate solution were simultaneously added to an aqueous gelatin solution at 75° C. within 15 min. while the gelatin solution was stirred strongly to obtain an emulsion containing octahedron silver bromide particles (mean particle size 0.35μ) (first step). In this case, 3,4-dimethyl-1,3-thiazolin-2-thione (3 g/l mol silver) were added to the solution. Then the resulting emulsion was subjected to a chemical sensitizing treatment by adding sodium thiosulfate (6 mg/l mol silver) and chloroauric acid (tetrahydrate) (7 mg/l mol silver) to the emulsion successively and heating at 75° C. for 80 min. Silver bromide particles in the chemically sensitized emulsion were further grown under the same condition as those of the above first step to obtain an octahedron monodispersed core/shell type silver bromide emulsion (mean particle size: 0.7 μ). The degree of variability of the particle size was about 10%. Then sodium thiosulfate (1.5 mg/l mol silver) and chloroauric acid (tetrahydrate) (1.5 mg/l mol silver) were added to the obtained emulsion and the mixture was subjected to chemical sensitization by heating at 60° C. for 60 min to obtain an internal latent image type silver halide emulsion.

$10^{-3}$% by weight (on the basis of the weight of silver halide) of ExZK-1 and $10^{-2}$% by weight of ExZK-2 were contained in each photosensitive layer as nucleus forming agents and $10^{-2}$% by weight of Cpd-22 was used as a nucleus formation accelerator. Further Alkanal XC (manufactured by Du pont) and sodium alkylbenzensulfonate as emulsion dispersing auxiliaries, and succinate and Magefac F120 (manufactured by Dainippon ink) as coating auxiliaries were contained in each layer. Stabilizers (Cpd-23,24,25) were contained in layers containing silver halide and colloidal silver.

Compounds used in this example were shown below.

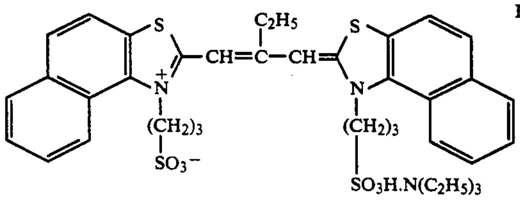

ExS-1

-continued
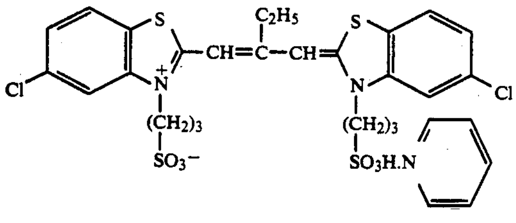
ExS-2
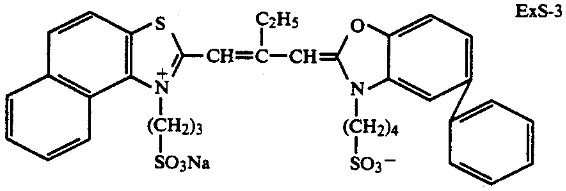
ExS-3
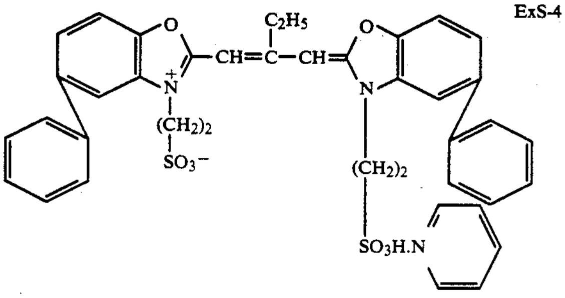
ExS-4
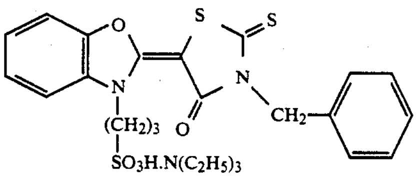
ExS-5
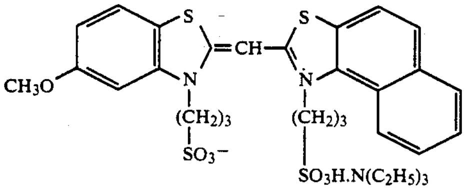
ExS-6
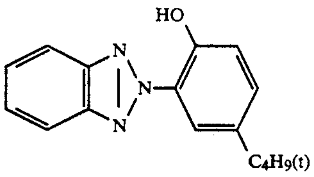
Cpd-1
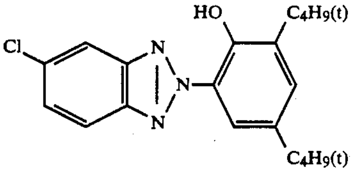
Cpd-2
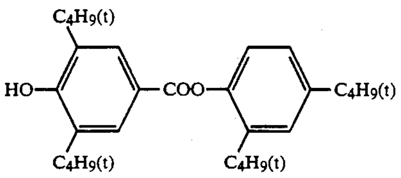
Cpd-3
-continued
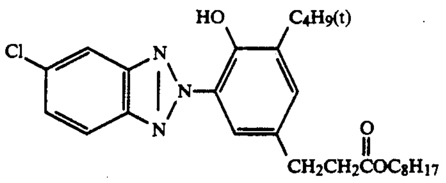
Cpd-4
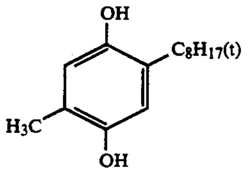
Cpd-5
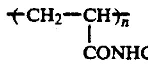 n = 100~1000
Cpd-6
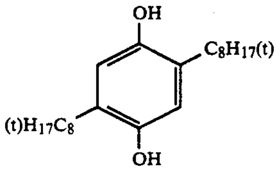
Cpd-7
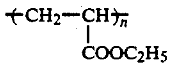
Cpd-8
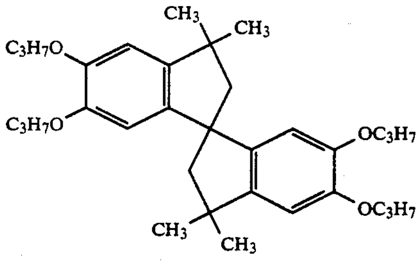
Cpd-9
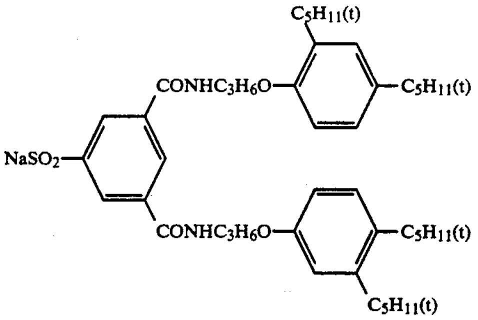
Cpd-10
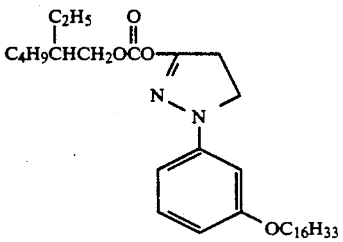
Cpd-11

-continued
Cpd-12
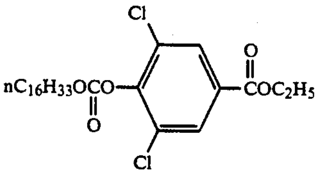
Cpd-13
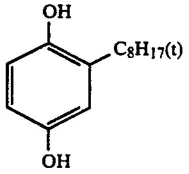
Cpd-14
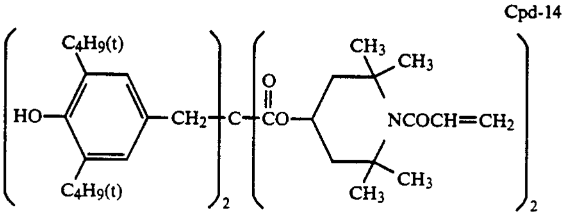
Cpd-15
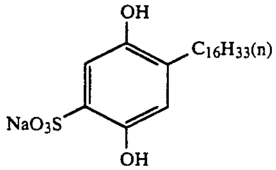
Cpd-16
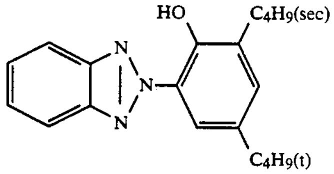
Cpd-17
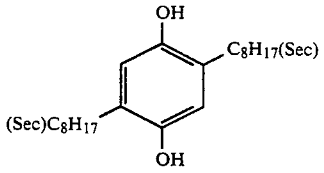
Cpd-18
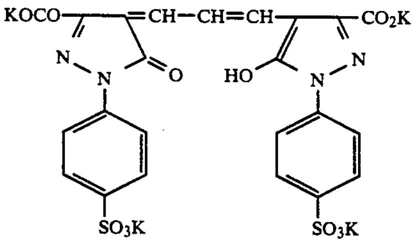
Cpd-19
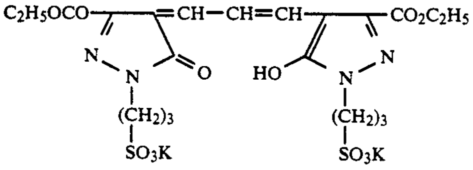
-continued
Cpd-20
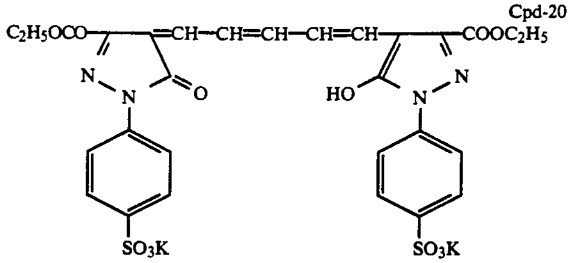
Cpd-21
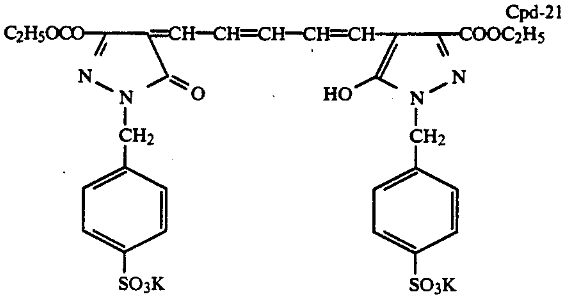
Cpd-22
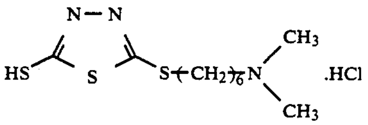
Cpd-23
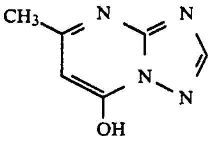
Cpd-24
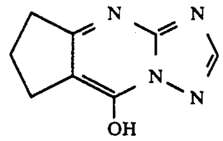
Cpd-25
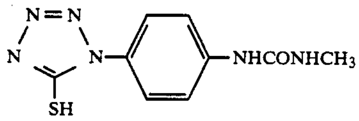
Cpd-26
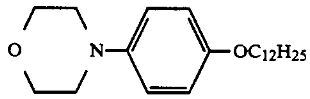
Cpd-27
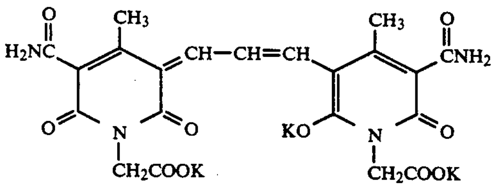
EXC-1
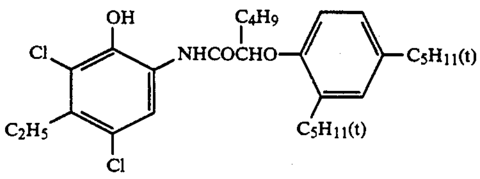

-continued

EXC-2

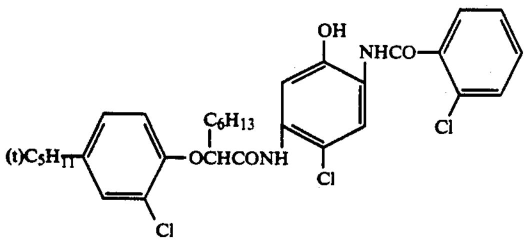

EXC-3

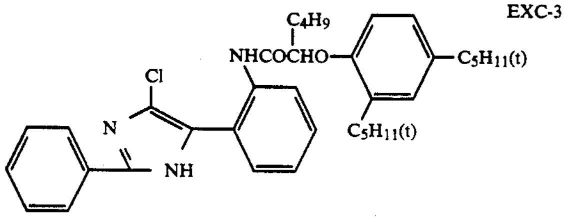

EXM-1

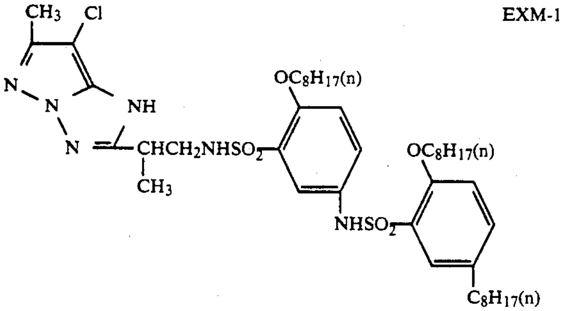

EXM-2

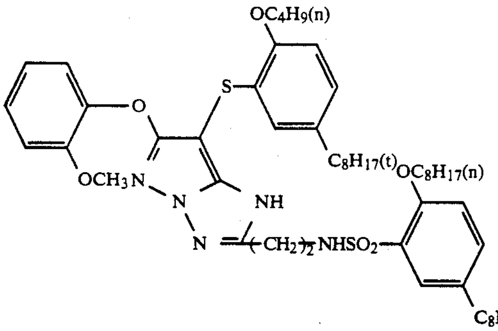

EXM-3

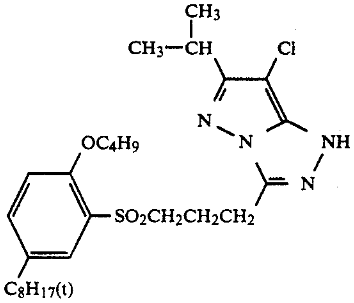

-continued

EXY-1

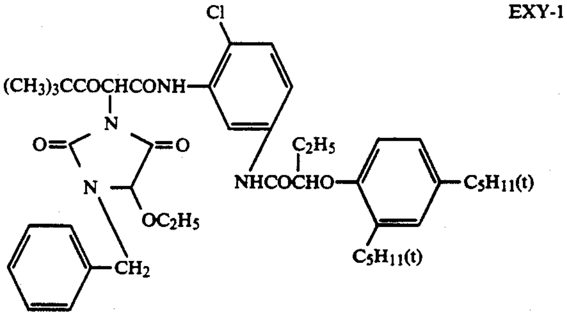

EXY-2

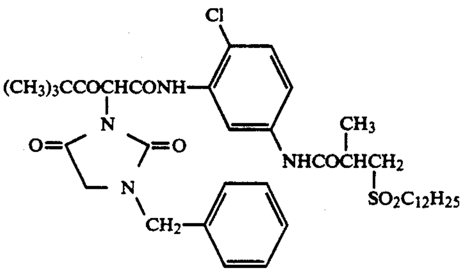

| | |
|---|---|
| di(2-ethylhexyl) sebacate | Solv-1 |
| trinonyl phosphate | Solv-2 |
| di(3-methylhexyl) phthalate | Solv-3 |
| tricresylphosphate | Solv-4 |
| dibutylphthalate | Solv-5 |
| trioctylphthalate | Solv-6 |
| di(2-ethylhexyl)phthalate | Solv-7 |
| 1,2-bis(vinylsulfonylacetoamide)ethane | H-1 |
| sodium 4,6-dichloro-2-hydroxy-1,3,5-triazine | H-2 |
| 7-(3-ethoxythiocarbonylaminobenzamido)-9-methyl-10-propargyl-1,2,3,4-tetrahydroacridinium trifluoromethanesulfonate | ExZK-1 |
| 2-[4-{3-[3-{3-[5-{3-[2-chloro-5-(1-dodecyloxycarbonylethoxycarbonyl) phenylcarbamoyl]-4-hydroxy-1-naphthylthio}tetrazol-1-yl] phenyl}ureido]benzensulfonamido}phenyl]-1-formylhydrazine | ExAK-2 |

A sample prepared as mentioned above was Sample 201.

Sample 202 was prepared according to the same procedures as those of Sample 201 except that an equimolar amount of cyan couple (1) of the present invention was used in place of cyan couplers ExC-1,2 and 3 used in the third and fourth layers.

Samples 203-207 were respectively prepared in the same manner as that of the preparation of Sample 201 except that cyan couplers ExC-1, 2 and 3 were replaced with an equimolar amount of cyan couplers (5), (6), (9), (16) and (17).

The resulting Samples 201-207 were exposed through a red filter and then treated in the following steps.

The spectral absorption of the treated samples was measured and it was found that a spectral absorption property of the samples (202-207) using the cyan couplers of the present invention is sharper than that of Sample 201.

| Treatment steps | Time | Temperature | Tank volume of mother liquid | Replenishing amount |
|---|---|---|---|---|
| Color development | 80 sec | 38° C. | 8 l | 300 ml/$m^2$ |
| Bleach-fixing | 40 sec | 33° C. | 3 l | 300 ml/$m^2$ |
| Washing (1) | 40 sec | 33° C. | 3 l | — |
| Washing (2) | 40 sec | 33° C. | 3 l | — |
| Washing (3) | 15 sec | 33° C. | 0.5 l | 320 ml/$m^2$ |
| Drying | 30 sec | 80° C. | — | — |

The amount of bleach-fixing solution carried by a photosensitive material from a bleach-fixing tank to washing tank (1) was 35 ml/$m^2$ and the ratio of amount of the replenished washing water to amount of the carried bleach-fixing solution was 9.1.

The composition of the treating solutions were as follows:

| | Mother liquid | Replenisher |
|---|---|---|
| Color developer | | |
| ethylenediaminetetrakismethylene phosphonic acid | 0.5 g | 0.5 g |
| diethylene glycol | 10 ml | 10 ml |
| benzyl alcohol | 12.0 ml | 14.4 ml |
| potassium bromide | 0.52 g | — |
| sodium chloride | 0.06 g | — |
| sodium sulfite | 2.4 g | 2.9 g |
| N,N-diethylhydroxylamine | 4.0 g | 4.8 g |
| triethylenediamine(1,4-diazabicyclo [2,2,2] octane) | 4.0 g | 4.8 g |
| 3-methyl-4-amino-N-ethyl-N (β-methanesulfonamidoethyl) aniline sulfate | 5.6 g | 6.6 g |
| potassium carbonate | 27.0 g | 25.0 g |
| fluorescent brightening agent (4,4'-diaminostilbene) | 1.0 g | 1.2 g |
| water | ad 1000 ml | 1000 ml |
| pH (25° C.) | 10.50 | 10.80 |
| Bleach-fixing solution | | |
| disodium ethylenediamine-tetraacetate.$2H_2O$ | 4.0 g | Same as mother liquid |
| iron (III) ammonium ethylene-diaminetetra acetate.$2H_2O$ | 46.0 g | |
| ammonium thiosulfate (700 g/l) | 155 ml | |
| sodium p-toluenesulfinate | 20.0 g | |
| sodium hydrogensulfite | 12.0 g | |
| ammonium bromide | 50.0 g | |
| ammonium nitrate | 30.0 g | |
| water | ad 1000 ml | |
| pH (25° C.) | 6.20 | |

Washing water (The same water was used as mother liquid and replenisher)

Tap water was passed through a column filled with H-type strong acid cation exchange resin (Rohm & Hass, Amberlite IR-120B) and OH-type anion exchange resin (Amberlite IR-400) to reduce calcium and magnesium ion concentration to 3 mg/l or less, and then sodium isocyanurate dichloride (20 mg/l) and sodium sulfate (1.5 g/l) were added to the ion-exchanged water. The pH of this water ranged from 6.5 to 7.5.

EXAMPLE 4

A multilayer silver halide photosensitive material 301 having the following layer structure was formed on a cellulose triacetate filmsubstrate having prime-coating.

LAYER STRUCTURE

The compositions of the respective layers will be shown below. The numerals stands for the applied amount (g/$m^2$). The amount of the silver halide emulsion is given in terms of silver.

| | | |
|---|---|---|
| The first layer (anti-halation layer) | | |
| black colloidal silver | silver | 0.18 |
| gelatin | | 1.40 |
| The second layer (interlayer) | | |
| 2,5-di-t-pentadecyl hydroquinone | | 0.18 |
| EX-1 | | 0.07 |
| EX-3 | | 0.02 |
| EX-12 | | 0.002 |
| U-1 | | 0.06 |
| U-2 | | 0.08 |
| U-3 | | 0.10 |
| HBS-1 | | 0.10 |
| HBS-2 | | 0.02 |
| gelatin | | 1.04 |
| The third layer (the first red-sensitive layer) | | |
| emulsion A | silver | 0.25 |
| emulsion B | silver | 0.25 |
| sensitizing dye I | | $6.9 \times 10^{-5}$ |
| sensitizing dye II | | $1.8 \times 10^{-5}$ |
| sensitizing dye III | | $3.1 \times 10^{-4}$ |
| EX-2 | | 0.355 |
| EX-10 | | 0.020 |
| HBS-1 | | 0.060 |
| gelatin | | 0.87 |
| The fourth layer (the second red-sensitive layer) | | |
| emulsion G | silver | 1.0 |
| sensitizing dye I | | $5.1 \times 10^{-5}$ |
| sensitizing dye II | | $1.4 \times 10^{-5}$ |
| sensitizing dye III | | $2.3 \times 10^{-4}$ |
| EX-2 | | 0.400 |
| EX-3 | | 0.050 |
| EX-10 | | 0.015 |
| HBS-1 | | 0.060 |
| gelatin | | 1.30 |
| The fifth layer (the third red-sensitive layer) | | |
| emulsion D | silver | 1.60 |
| sensitizing dye I | | $5.4 \times 10^{-5}$ |
| sensitizing dye II | | $1.4 \times 10^{-5}$ |
| sensitizing dye III | | $2.4 \times 10^{-4}$ |
| EX-3 | | 0.010 |
| EX-4 | | 0.080 |
| EX-2 | | 0.097 |
| HBS-1 | | 0.22 |
| HBS-2 | | 0.10 |
| gelatin | | 1.63 |
| The sixth layer (interlayer) | | |
| EX-5 | | 0.040 |
| HBS-1 | | 0.020 |
| gelatin | | 0.80 |
| The seventh layer (the first green sensitive layer) | | |
| emulsion A | silver | 0.15 |
| emulsion B | silver | 0.15 |
| sensitizing dye V | | $3.0 \times 10^{-5}$ |
| sensitizing dye VI | | $1.0 \times 10^{-4}$ |
| sensitizing dye VII | | $3.8 \times 10^{-4}$ |
| EX-6 | | 0.260 |
| EX-1 | | 0.021 |
| EX-7 | | 0.030 |
| EX-8 | | 0.025 |
| HBS-1 | | 0.100 |
| HBS-3 | | 0.010 |
| gelatin | | 0.63 |
| The eighth layer (the second green-sensitive layer) | | |
| emulsion C | silver | 0.45 |
| sensitizing dye V | | $2.1 \times 10^{-5}$ |
| sensitizing dye VI | | $7.0 \times 10^{-5}$ |
| sensitizing dye VII | | $2.6 \times 10^{-4}$ |
| EX-6 | | 0.094 |
| EX-8 | | 0.018 |
| EX-7 | | 0.026 |
| HBS-1 | | 0.160 |
| HBS-3 | | 0.008 |

-continued

| | | |
|---|---|---|
| gelatin | | 0.50 |
| The ninth layer (the third green-sensitive layer) | | |
| emulsion E | silver | 1.2 |
| sensitizing dye V | | $3.5 \times 10^{-5}$ |
| sensitizing dye VI | | $8.0 \times 10^{-5}$ |
| sensitizing dye VII | | $3.0 \times 10^{-4}$ |
| EX-13 | | 0.015 |
| EX-11 | | 0.100 |
| EX-1 | | 0.025 |
| HBS-1 | | 0.25 |
| HBS-2 | | 0.10 |
| gelatin | | 1.54 |
| The tenth layer (yellow filter layer) | | |
| yellow colloidal silver | silver | 0.05 |
| EX-5 | | 0.08 |
| HBS-1 | | 0.03 |
| gelatin | | 0.95 |
| The eleventh layer (the first blue-sensitive layer) | | |
| emulsion A | silver | 0.08 |
| emulsion B | silver | 0.07 |
| emulsion F | silver | 0.07 |
| sensitizing dye VIII | | $3.5 \times 10^{-4}$ |
| EX-9 | | 0.721 |
| EX-8 | | 0.042 |
| HBS-1 | | 0.28 |
| gelatin | | 1.10 |
| The twelfth layer (the second blue-sensitive layer) | | |
| emulsion G | silver | 0.45 |

-continued

| | | |
|---|---|---|
| sensitizing dye VIII | | $2.1 \times 10^{-4}$ |
| EX-9 | | 0.154 |
| EX-10 | | 0.007 |
| HBS-1 | | 0.05 |
| gelatin | | 0.78 |
| The thirteenth layer (the third blue-sensitive layer) | | |
| emulsion H | silver | 0.77 |
| sensitizing dye VIII | | $2.2 \times 10^{-4}$ |
| EX-9 | | 0.20 |
| HBS-1 | | 0.07 |
| gelatin | | 0.69 |
| The fourteenth layer (the first protective layer) | | |
| emulsion I | silver | 0.5 |
| U-4 | | 0.11 |
| U-5 | | 0.17 |
| HBS-1 | | 0.05 |
| gelatin | | 1.00 |
| The fifteenth layer (the second protective layer) | | |
| polymethylmethacryate particles (diameter: about 1.5 μm) | | 0.54 |
| S-1 | | 0.20 |
| gelatin | | 1.20 |

A hardener for gelatin H-1 and a surfactant were added to each layer in addition to the above-mentioned components.

| | Mean content of AgI (%) | Mean particle size (μm) | Degree of variability concerning particle size (%) | Ratio (diameter/ thickness) | Ratio of amount of Silver (AgI content %) |
|---|---|---|---|---|---|
| Emulsion A | 4.1 | 0.45 | 27 | 1 | Core/Shell = 1/3 (13/1), double layer structure grain |
| Emulsion B | 8.9 | 0.70 | 14 | 1 | Core/Shell = 3/7 (25/2), double layer structure grain |
| Emulsion C | 10 | 0.75 | 30 | 2 | Core/Shell = 1/2 (24/3), double layer structure grain |
| Emulsion D | 16 | 1.05 | 35 | 2 | Core/Shell = 1/2 (40/0), double layer structure grain |
| Emulsion E | 10 | 1.05 | 35 | 3 | Core/Shell = 1/2 (24/3), double layer structure grain |
| Emulsion F | 4.1 | 0.25 | 28 | 1 | Core/Shell = 1/3 (13/1), double layer structure grain |
| Emulsion G | 13.6 | 0.75 | 25 | 2 | Core/Shell = 1/2 (40/0), double layer structure grain |
| Emulsion H | 14 | 1.30 | 25 | 3 | Core/Shell = 37/63 (34/3), double layer structure grain |
| Emulsion I | 1 | 0.07 | 15 | 1 | homogeneous grain |

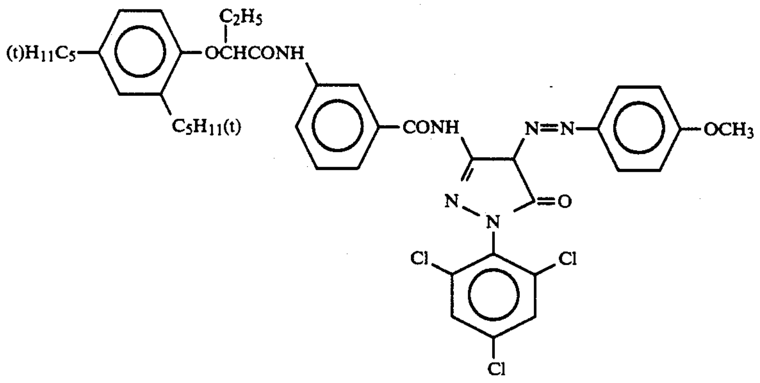

EX-1

-continued
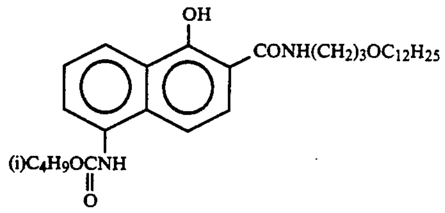
EX-2
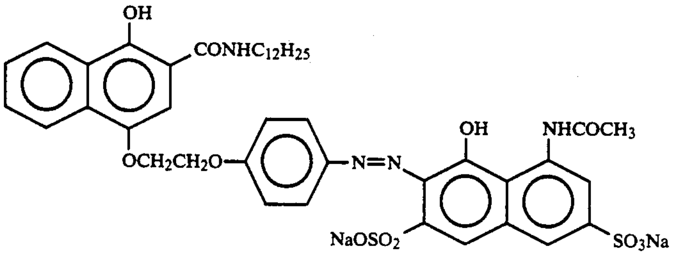
EX-3
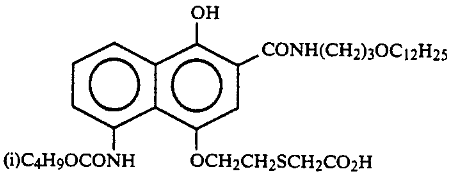
EX-4
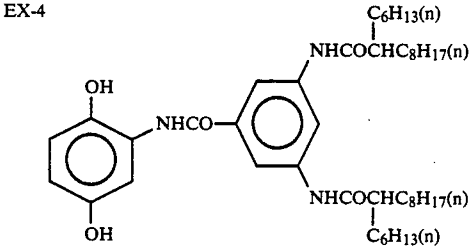
EX-5
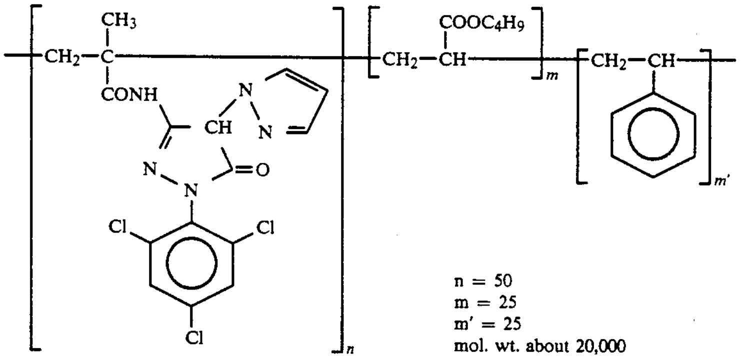
n = 50
m = 25
m' = 25
mol. wt. about 20,000
EX-6
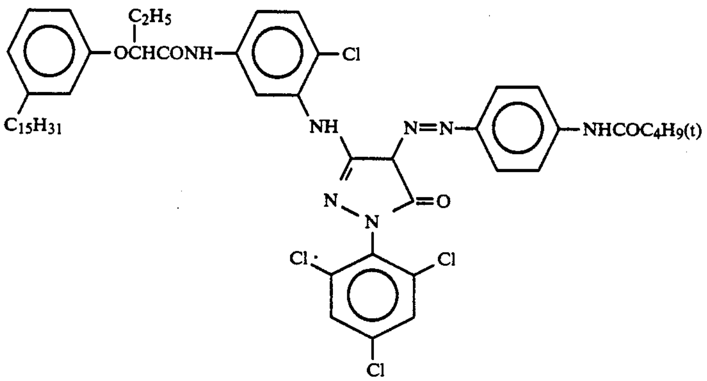
EX-7

-continued
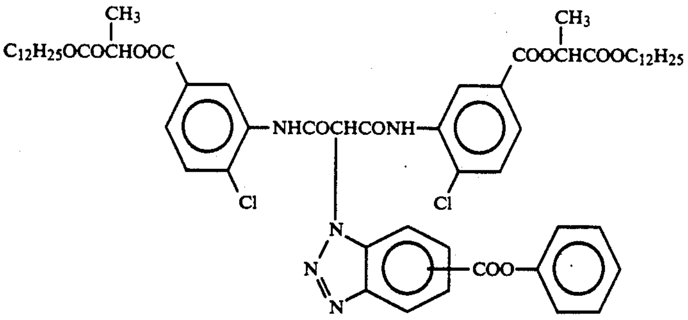
EX-8
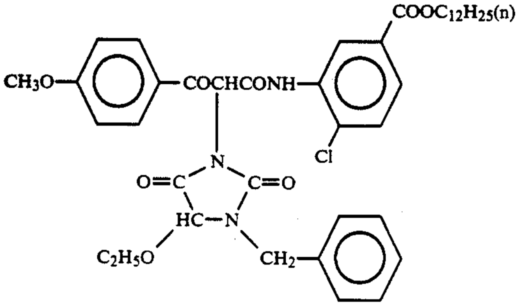
EX-9
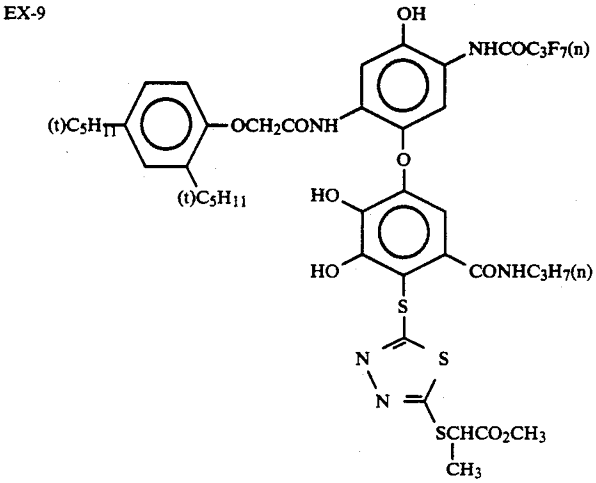
EX-10
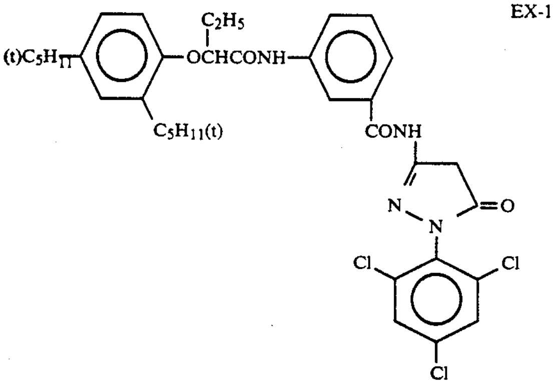
EX-11
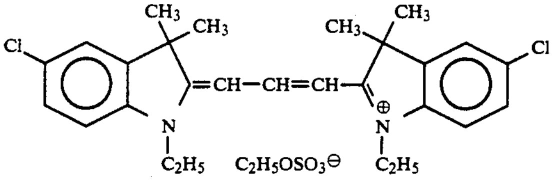
EX-12
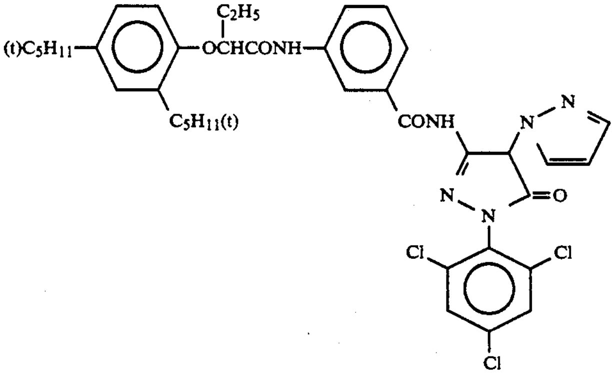
EX-13

-continued
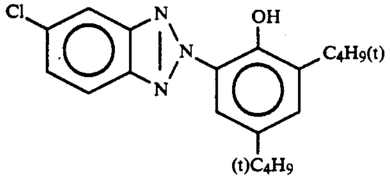
U-1
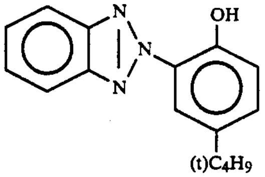
U-2
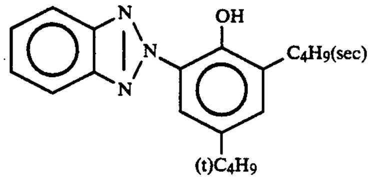
U-3
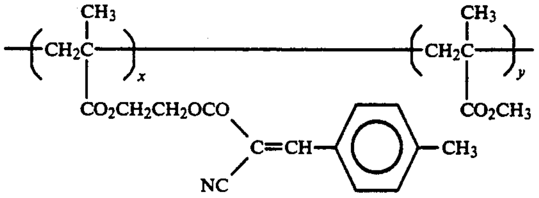
x:y = 70:30 (wt %)
U-4
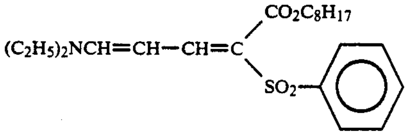
UV-5
tricresylphosphate HBS-1
di-n-butylphthalate HBS-2
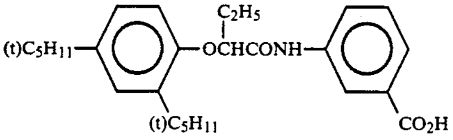
HBS-3
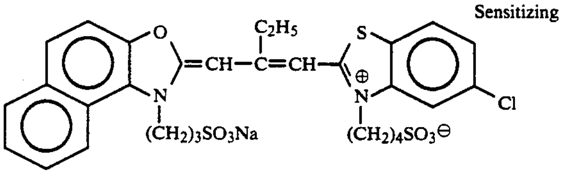
Sensitizing dye I
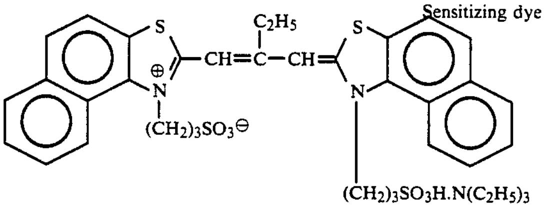
Sensitizing dye II
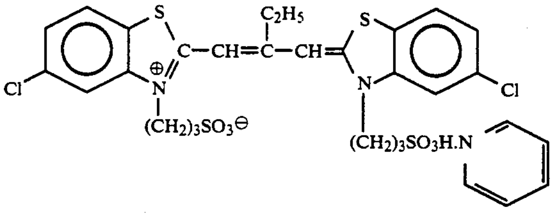
Sensitizing dye III
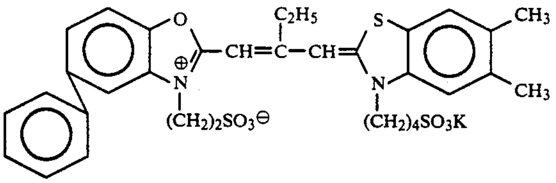
Sensitizing dye V
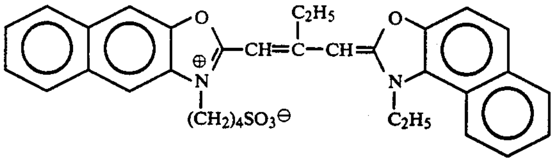
Sensitizing dye VI
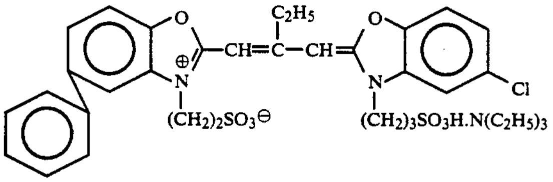
Sensitizing dye VII
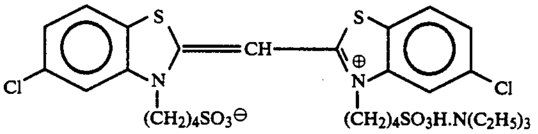
Sensitizing dye VIII
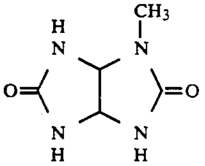
S-1
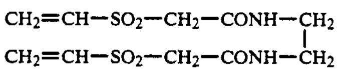
H-1

A sample prepared as mentioned above was Sample 301.

Sample 302 was prepared according to the same procedures as those of Sample 301 except that an equimolar amount of cyan coupler (1) of the present invention was used in place of cyan couplers Ex-2 and Ex-4 used in the third, fourth and fifth layers.

Samples 303–307 were respectively prepared in the same manner as that of the preparation of Sample 301 except that cyan couplers Ex-2 and Ex-4 were replaced with an equimolar amount of cyan couplers (5), (6), (9), (16) and (17).

The resulting Samples 301–307 were exposed through a red filter and then treated in the following steps.

The spectral absorption of the treated samples was measured and it was found that a spectral absorption property of the samples (302–307) using the cyan couplers of the present invention is sharper than that of Sample 301.

| Treatment steps<br>Steps | Temperature | Time | Replenisher* | Tank volume |
|---|---|---|---|---|
| Color development | 37.8° C. | 3'15" | 2 l | 5 l |
| Bleach-fixing | 38.0° C. | 45" | 4.5 | 2 l |
| Fixing (1) | 38.0° C. | 45" | ** | 2 l |
| Fixing (2) | 38.0° C. | 45" | 30 | 2 l |
| Stabilizing (1) | 38.0° C. | 20" | | 1 l |
| Stabilizing (2) | 38.0° C. | 20" | *** | 1 l |
| Stabilizing (3) | 38.0° C. | 20" | 35 | 1 |
| Drying | 55° C. | 1'00" | | |

*Amounts of replenisher are expressed on the basis of 1 m of photosensitive material having a width of 35 mm.
**Two-tank countercurrent system
***Three-tank countercurrent system A jet agitator disclosed in J.P. KOKAI No. 63-183460 (page 3) was set in the fixing tanks in the automatic developing machine used.

The above treatment was conducted while a jet of a fixing solution was sprayed on the emulsion surface of the treated photosensitive material.

| Color developer | | Mother liquid (g) | Replenisher (g) |
|---|---|---|---|
| hydroxyethyliminodiacetic acid | | 5.0 | 6.0 |
| sodium sulfite | | 4.0 | 3.0 |
| potassium carbonate | | 30.0 | 37.0 |
| potassium bromide | | 1.3 | 0.5 |
| potassium iodide | | 2.0 | 3.6 |
| hydroxyamine sulfate | | 1.2 mg | — |
| 4-[N-ethyl-N-$\beta$-hydroxyethyl-amino]-2-methylaniline sulfate | | $1.0 \times 10^{-2}$ mol | $1.3 \times 10^{-2}$ mol |
| water | ad | 1.0 l | 1.0 l |
| | | 10.00 | 10.15 |

| Bleaching solution | | Mother liquid (g) | Replenisher (g) |
|---|---|---|---|
| iron (III) 1,3-diaminopropane tetraacetate | | 130 | 190 |
| 1,3-diaminopropane tetraacetic acid | | 3.0 | 4.0 |
| ammonium bromide | | 85 | 120 |
| acetic acid | | 50 | 70 |
| ammonium nitrate | | 30 | 40 |
| water | ad | 1.0 l | 1.0 l |
| pH (adjusted with acetic acid or ammonia | | 4.3 | 3.5 |

-continued

| Fixing solution | | Mother liquid (g) | Replenisher (g) |
|---|---|---|---|
| 1-hydroxyethylidene-1,1-diphosphonic acid | | 5.0 | 7.0 |
| disodium ethylenediamine tetraacetate | | 0.5 | 0.7 |
| sodium sulfite | | 10.0 | 12.0 |
| sodium hydrogensulfite | | 8.0 | 10.0 |
| aqueous ammonium thiosulfate solution (700 g/l) | | 170.0 ml | 200.0 ml |
| Rhodanammon | | 100.0 | 150.0 |
| thiourea | | 3.0 | 5.0 |
| 3,6-dithia-1,8-octanediol | | 3.0 | 5.0 |
| water | ad | 1.0 l | 1.0 l |
| pH (adjusted with acetic acid or ammonia) | | 6.5 | 6.7 |

| Stabilizing solution (Composition of replenisher is the same as that of mother liquid) | | |
|---|---|---|
| formalin (37%) | | 1.2 ml |
| 5-chloro-2-methyl-4-isothiazolin-3-one | | 6.0 mg |
| 2-methyl-4-isothiazolin-3-one | | 3.0 mg |
| surfactant ($C_{10}H_{21}$—O—$(CH_2CH_2O)_{10}$—H) | | 0.4 |
| ethylene glycol | | 1.0 |
| water | ad | 1.0 l |
| pH | | 5.0–7.0 |

EXAMPLE 5

A multilayer silver halide photosensitive material 401 having the following layer structure was formed on a cellulose triacetate film substrate (thickness: 127 μ) with prime-coating.

| | | |
|---|---|---|
| The first layer (anti-halation layer) | | |
| gelatin layer (thickness of dried one: 2μ) containing: | | |
| black colloidal silver | | 0.25 g/m² |
| U.V. absorber U-1 | | 0.04 g/m² |
| U.V. absorber U-2 | | 0.1 g/m² |
| U.V. absorber U-3 | | 0.1 g/m² |
| high b.p. solvent O-1 | | 0.1 cc/m² |
| The second layer (interlayer) | | |
| gelatin layer (thickness of dried one: 1μ) containing: | | |
| A-14 | | 2.5 mg/m² |
| compound H-1 | | 0.05 g/m² |
| emulsion A | silver | 0.05 g/m² |
| high b.p. solvent O-2 | | 0.05 cc/m² |
| The third layer (the first red-sensitive layer) | | |
| gelatin layer (thickness of dried one: 0.7μ) containing: | | |
| monodispersed silver bromoiodide emulsion spectrally sensitized with sensitizing dyes S-1 (0.47 mg/m²) and S-2 (0.02 mg/m²) (iodine content: 4 mol %, mean particles size: 0.02μ, degree of variability: 12%) | silver | 0.15 g/m² |
| monodispersed internal latent type silver bromoiodide emulsion spectrally sensitized with sensitizing dyes S-1 (0.51 mg/m²) and S-2 (0.03 mg/m²) (iodine content: 4 mol %, mean particle size: 0.40μ, distance from latent image to particle surface: 100 Å, degree of variability: 14%) | silver | 0.20 g/m² |
| emulsion B | silver | 0.05 g/m² |
| A-1 | | 0.60 mg/m² |
| compound H-6 | | 0.01 g/m² |
| coupler C-1 | | 0.13 g/m² |
| coupler C-2 | | 0.033 g/m² |
| coupler C-10 | | 0.1 g/m² |
| high b.p. solvent O-2 | | 0.02 cc/m² |
| The foruth layer (the second red-sensitive layer) | | |
| gelatin layer (thickness of dried one: 1.7μ) containing: | | |
| monodispersed silver bromoiodide emulsion spectrally sensitized with sensitizing dyes S-1 | silver | 0.53 g/m² |

-continued

| | | |
|---|---|---|
| ($1.1\ mg/m^2$) and S-2 ($0.04\ mg/m^2$) (iodine content: 3 mol %, mean particle size: 0.55μ, degree of variability: 16%) | | |
| A-4 | | $0.02\ mg/m^2$ |
| coupler C-1 | | $0.40\ g/m^2$ |
| coupler C-2 | | $0.07\ g/m^2$ |
| coupler C-9 | | $0.05\ g/m^2$ |
| high b.p. solvent O-2 | | $0.22\ cc/m^2$ |
| The fifth layer (the third red-sensitive layer) gelatin layer (thickness of dried one: 1.7μ) containing: | | |
| monodispersed silver bromo-iodide emulsion spectrally sensitized with sensitizing dyes S-1 ($1.1\ mg/m^2$) and S-2 ($0.04\ mg/m^2$) (iodine content: 2 mol %, mean particle size: 0.07μ, degree of variability: 17%) | silver | $0.53\ g/m^2$ |
| A-7 | | $1.2\ mg/m^2$ |
| coupler C-6 | | $0.35\ g/m^2$ |
| coupler C-8 | | $0.20\ g/m^2$ |
| high b.p. solvent O-2 | | $0.06\ cc/m^2$ |
| The sixth layer (interlayer) gelatin layer (thickness of dried one: 1μ) containing: | | |
| A-10 | | $10\ mg/m^2$ |
| A-11 | | $5\ mg/m^2$ |
| compound H-1 | | $0.1\ g/m^2$ |
| high b.p. solvent O-2 | | $0.1\ cc/m^2$ |
| The seventh layer (the first green-sensitive layer) gelatin layer (thickness of dried one: 0.7μ) containing: | | |
| monodispersed silver bromoiodide emulsion spectrally sensitized with sensitizing dyes S-3 ($2.2\ mg/m^2$) and S-4 ($1.0\ mg/m^2$) (iodine content: 3 mol %, mean particle size: 0.35μ, degree of variability: 19%) | silver | $0.5\ g/m^2$ |
| emulsion B | silver | $0.05\ g/m^2$ |
| A-5 | | $0.12\ mg/m^2$ |
| compound H-6 | | $0.01\ g/m^2$ |
| compound H-5 | | $0.005\ g/m^2$ |
| coupler C-3 | | $0.27\ g/m^2$ |
| high b.p. solvent O-2 | | $0.05\ cc/m^2$ |
| The eighth layer (the second green-sensitive layer) gelatin layer (thickness of dried one: 1.7μ) containing: | | |
| monodispersed internal latent image type silver bromoiodide emulsion spectrally sensitized with sensitizing dyes S-3 ($0.29\ g/m^2$) and S-4 ($0.3\ mg/m^2$) (iodine content: 2.5 mol %, mean particle size: 0.5μ, distance from latent image to particle surface: 100 Å, degree of variability: 18%) | silver | $0.5\ g/m^2$ |
| A-6 | | $0.2\ mg/m^2$ |
| compound H-6 | | $0.01\ g/m^2$ |
| coupler C-3 | | $0.2\ g/m^2$ |
| high b.p. solvent O-2 | | $0.13\ cc/m^2$ |
| The ninth layer (the third green-sensitive layer) gelatin layer (thickness of dried one: 1.7μ) containing: | | |
| tabular silver bromoiodide emulsion spectrally sensitized with sensitizing dyes S-3 ($0.9\ g/m^2$) and S-4 ($0.3\ mg/m^2$) (iodine content: 2 mol %, content of grains having 7 or more of diameter/thickness ratio: 50% (on the basis of projected area of the whole grains), mean thickness of grains: 0.10μ) | silver | $0.5\ g/m^2$ |
| A-2 | | $1.5\ mg/m^2$ |
| coupler C-4 | | $0.2\ g/m^2$ |
| high b.p. solvent O-2 | | $0.03\ cc/m^2$ |
| The tenth layer (interlayer) gelatin layer (thickness of dried one: 0.05μ) containing: | | |
| compound H-4 | | $0.1\ g/m^2$ |
| high b.p. solvent O-2 | | $0.1\ cc/m^2$ |
| The eleventh layer (yellow filter layer) gelatin layer (thickness of dried one: 1μ) containing: | | |
| yellow colloidal silver | silver | $0.12\ g/m^2$ |
| compound A-15 | | $0.22\ g/m^2$ |
| compound H-1 | | $0.02\ g/m^2$ |
| compound H-2 | | $0.03\ g/m^2$ |
| high b.p. solvent O-2 | | $0.04\ cc/m^2$ |
| The twelfth layer (the first blue-sensitive layer) gelatin layer (thickness of dried one: 1.5μ) containing: | | |

-continued

| | | |
|---|---|---|
| tabular silver bromoiodide emulsion spectrally sensitized with sensitizing dye S-5 ($1.0\ g/m^2$) (iodine content: 3 mol %, content of grains having 7 or more of diameter/thickness ratio: 50% (on the basis of projected area of the whole grains), mean thickness of grains: 0.10μ) | silver | $0.6\ g/m^2$ |
| emulsion A | silver | $0.1\ g/m^2$ |
| A-7 | | $0.5\ mg/m^2$ |
| coupler C-5 | | $0.5\ g/m^2$ |
| high b.p. solvent O-2 | | $0.1\ cc/m^2$ |
| The thirteenth layer (the second blue-sensitive layer) gelatin layer (thickness of dried one: 3μ) containing: | | |
| tabular silver bromoiodide emulsion spectrally sensitized with sensitizing dye S-5 ($2.0\ g/m^2$) (iodine content: 2.5 mol %, content of grains having 7 or more of diameter/thickness ratio: 50% (on the basis of projected area of the whole grains), mean thickness of grains: 0.15μ) | silver | $1.1\ g/m^2$ |
| A-12 | | $10\ mg/m^2$ |
| coupler C-7 | | $1.2\ g/m^2$ |
| coupler C-8 | | $0.2\ g/m^2$ |
| high b.p. solvent O-2 | | $0.07\ cc/m^2$ |
| The fourteenth layer (the first protective layer) gelatin layer (thickness of dried one: 2μ) containing: | | |
| A-13 | | $0.10\ mg/m^2$ |
| U.V. absorber U-1 | | $0.02\ g/m^2$ |
| U.V. absorber U-2 | | $0.03\ g/m^2$ |
| U.V. absorber U-3 | | $0.03\ g/m^2$ |
| U.V. absorber U-4 | | $0.29\ g/m^2$ |
| high b.p. solvent O-2 | | $0.28\ cc/m^2$ |
| The fifteenth layer (the second protective layer) gelatin layer (thickness of dried one: 0.8μ) containing: | | |
| emulsion of silver bromoiodide fine particles of which surface has been fogged (iodine content: 1 mol %, mean particle size: 0.06μ) | silver | $0.1\ g/m^2$ |
| A-8 | | $10\ mg/m^2$ |
| polymethylmethacrylate particles (mean particle size: 1.5μ) | | $0.1\ g/m^2$ |
| A-3 | | $0.2\ g/m^2$ |
| A-9 | | $1.0\ mg/m^2$ |

Anti-foggant A-16, hardener for gelatin H-3 and a surfactant were added to each layer in addition to the abovementioned components.

PREPARATION METHOD OF EMULSIONS A AND B

Emulsion A was prepared by preparing cubic silver bromide (mean particle size: 0.15 μ) by the controlled double-jet method and fogging the resulting silver bromide with hydradine and a complex of gold under the low pAg condition.

Emulsion B was prepared by providing a silver bromide shell (thickness: 250 Å) on the surface of silver bromide grains of emulsion A.

Compounds used in this example were shown below:

C-1

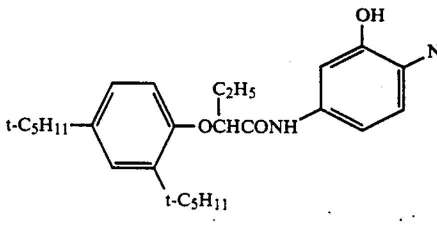

-continued
C-2
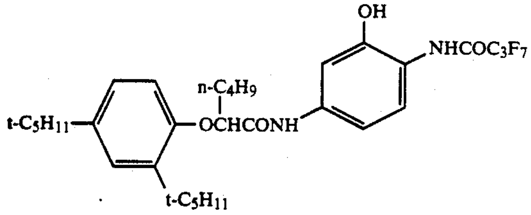
C-3
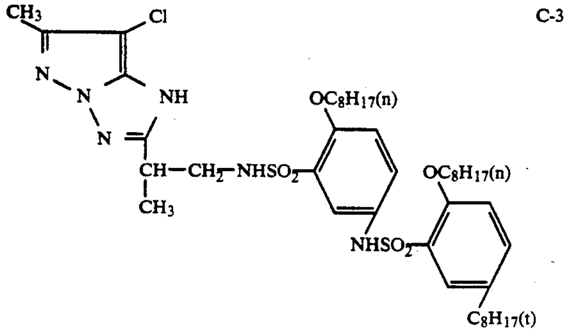
C-4
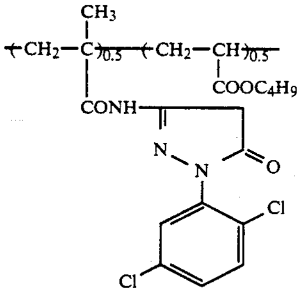
C-5
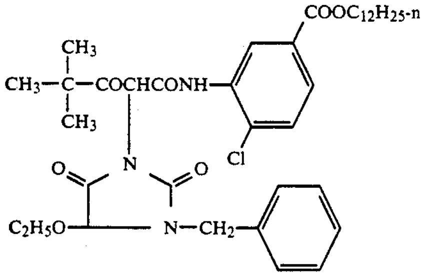
C-6
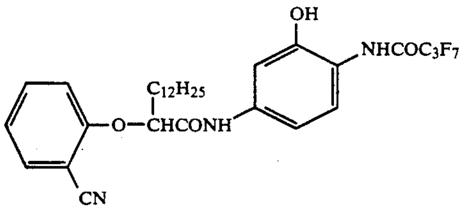
C-7
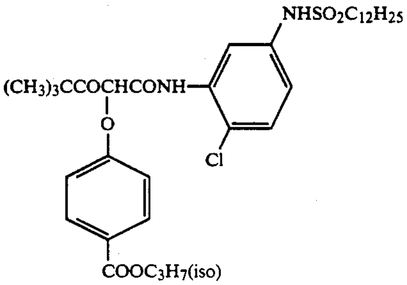
-continued
C-8
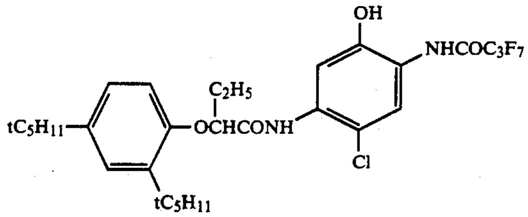
C-9
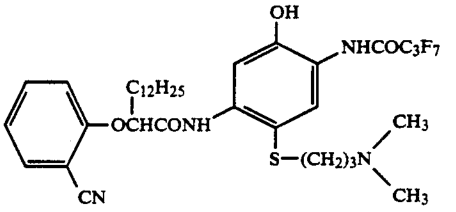
C-10
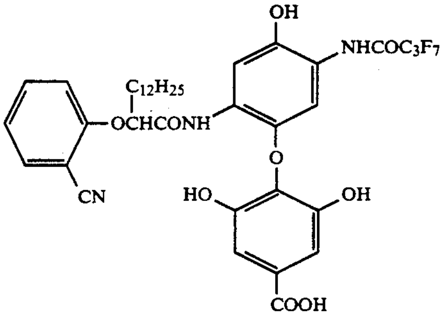
U-1
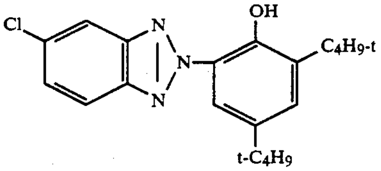
U-2
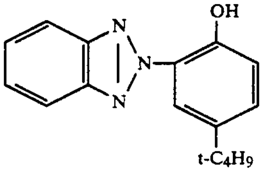
U-3
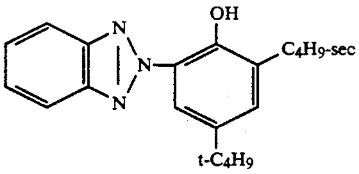
U-4
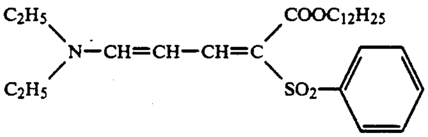
H-1
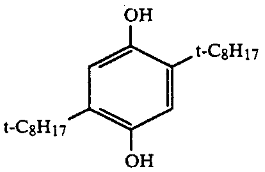

-continued
H-2
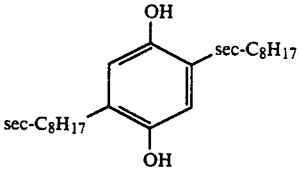
H-3
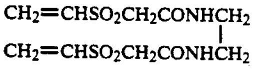
H-4
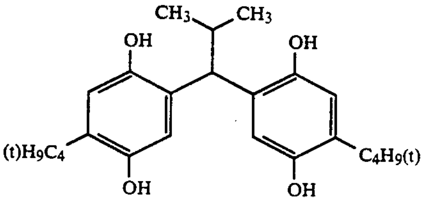
H-5
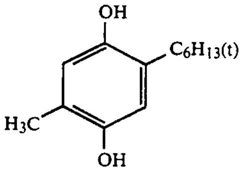
H-6
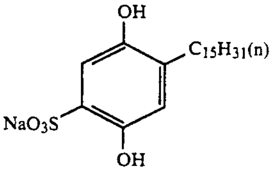
O-1
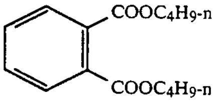
O-2
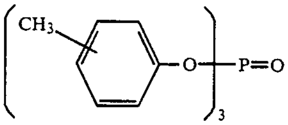
S-1
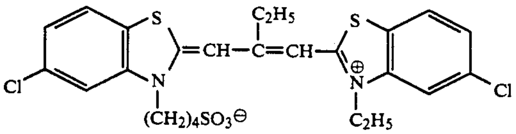
S-2
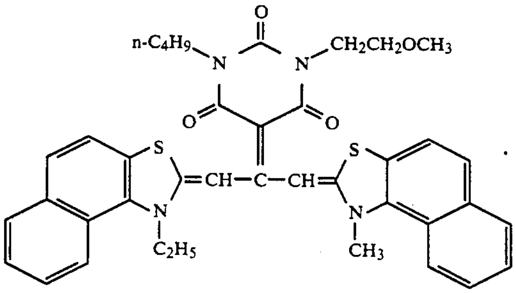
-continued
S-3
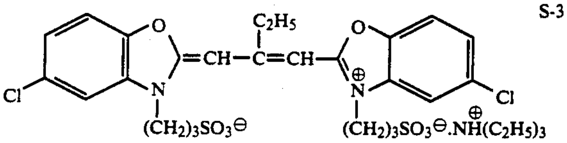
S-4
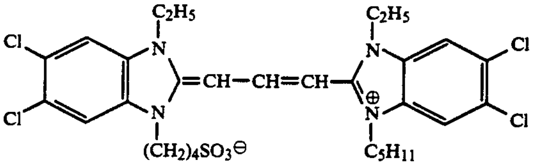
S-5
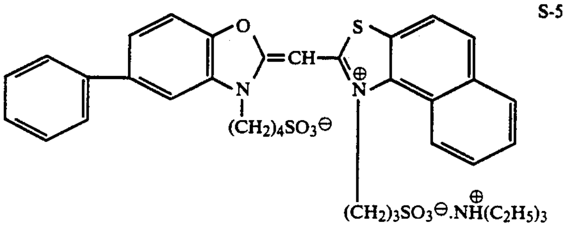
A-1
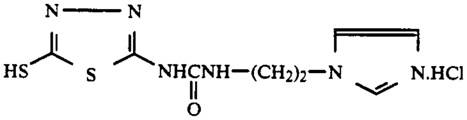
A-2
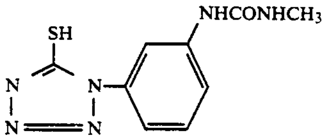
A-3
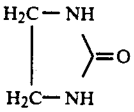
A-4
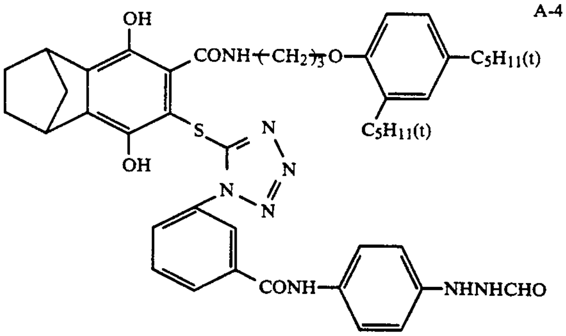
A-5
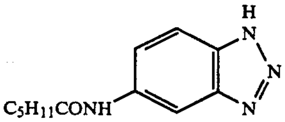
A-6
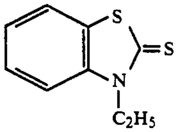

-continued

A-7

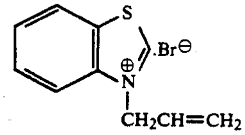

A-8

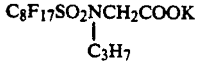

A-9

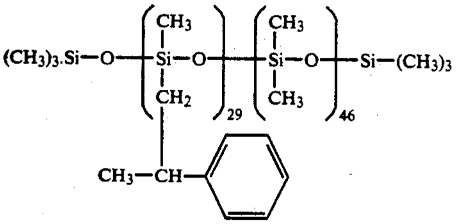

A-10

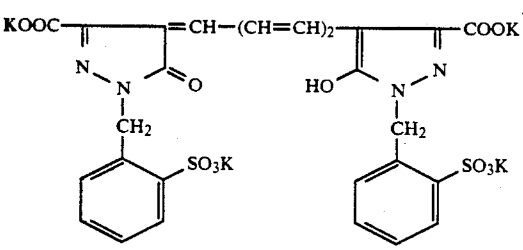

A-11

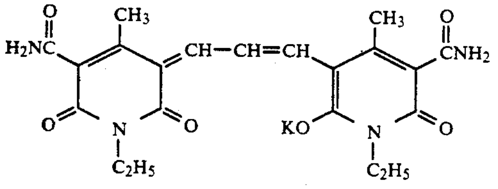

A-12

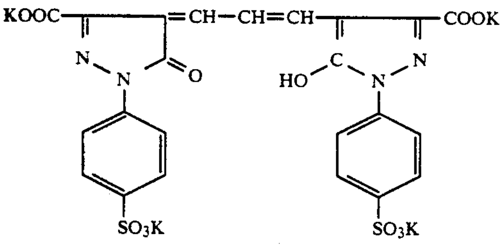

A-13

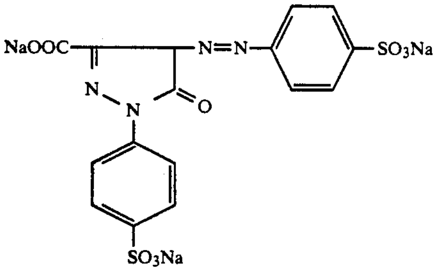

A-14

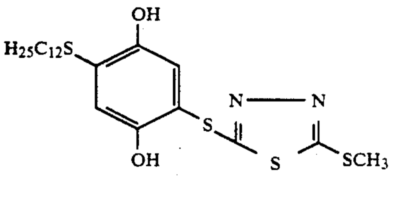

-continued

A-15

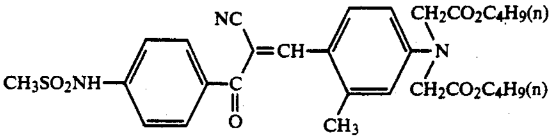

A-16

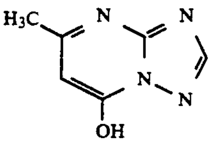

A sample prepared as mentioned above was Sample 401.

Sample 402 was prepared according to the same procedures as those of Sample 401 except that an equimolar amount of cyan coupler (1) of the present invention was used in place of cyan couplers ExC-1, 2, 6, and 8 used in the third, fourth and fifth layers.

Samples 403–407 were respectively prepared in the same manner as that of the preparation of Sample 401 except that cyan couplers ExC-1, 2, 6 and 8 were replaced with an equimolar amount of cyan couplers (5), (6), (9), (16) and (17).

The resulting Samples 401–407 were exposed through a red filter and then treated in the following steps.

The spectral absorption of the treated samples was measured and it was found that a spectral absorption property of the samples (402–407) using the cyan couplers of the present invention is sharper than that of Sample 401.

| Treatment steps | Time | Temperature |
|---|---|---|
| First development | 6′ | 38° C. |
| Washing | 2′ | 38° C. |
| Reversal | 2′ | 38° C. |
| Color developing | 6′ | 38° C. |
| Conditioning | 2′ | 38° C. |
| Bleaching | 6′ | 38° C. |
| Fixing | 4′ | 38° C. |
| Washing | 4′ | 38° C. |
| Stabilizing | 1′ | 25° C. |

The compositions of the treating solutions were as follows:

| | | | |
|---|---|---|---|
| First developer | | | |
| pentasodium nitrilo-N,N,N-trimethylene phosphonate | | 2.0 | g |
| sodium sulfite | | 30 | g |
| hydroquinone.potassium monosulfonate | | 20 | g |
| potassium carbonate | | 33 | g |
| 1-phenyl-4-methyl-4-hydroxymethyl-3-pyrazolidone | | 2.0 | g |
| potassium bromide | | 2.5 | g |
| potassium thiocyanate | | 1.2 | g |
| potassium iodide | | 2.0 | mg |
| water | ad | 1000 | ml |
| pH (adjusted with HCl or KOH) | | 9.60 | |
| Reversal solution | | | |
| pentasodium nitrilo-N,N,N-trimethylene phosphonate | | 3.0 | g |
| $SnCl_4.2H_2O$ | | 1.0 | g |
| p-aminophenol | | 0.1 | g |
| sodium hydroxide | | 8 | g |
| glacial acetic acid | | 15 | ml |
| water | ad | 1000 | ml |
| pH (adjusted with HCl or NaOH) | | 6.00 | |

-continued

| | | | |
|---|---|---|---|
| Color developer | | | |
| pentasodium nitrilo-N,N,N-trimethylene phosphonate | | 2.0 | g |
| sodium sulfite | | 7.0 | g |
| $Na_3PO_4.12H_2O$ | | 36 | g |
| potassium bromide | | 1.0 | g |
| potassium iodide | | 90 | mg |
| sodium hydroxide | | 3.0 | g |
| citrazinic acid | | 1.5 | g |
| N-ethyl-N-(β-methanesulfonamidoethyl)-3-methyl-4-aminoaniline sulfate | | 11 | g |
| 3,6-dithiaoctane-1,8-diol | | 1.0 | g |
| water | ad | 1000 | ml |
| pH (adjusted with HCl or KOH) | | 11.80 | |
| Conditioning solution | | | |
| disodium ethylenediaminetetraacetate.$2H_2O$ | | 8.0 | g |
| sodium sulfite | | 12 | g |
| 1-thioglycerol | | 0.4 | ml |
| water | ad | 1000 | ml |
| pH (adjusted with HCl or NaOH) | | 6.20 | |
| Bleaching solution | | | |
| disodium ethylenediaminetetraacetate $2H_2O$ | | 2.0 | g |
| Fe (III) ammonium ethylenediamine tetraacetate.$2H_2O$ | | 120 | g |
| potassium bromide | | 100 | g |
| ammonium nitrate | | 10 | g |
| water | ad | 1000 | ml |
| pH (adjusted with HCl or NaOH) | | 5.70 | |
| Fixing solution | | | |
| sodium thiosulfate | | 80 | g |
| sodium sulfite | | 5.0 | g |
| sodium hydrogensulfite | | 5.0 | g |
| water | ad | 1000 | ml |
| pH (adjusted with HCl or aqueous ammonia) | | 6.60 | |
| Stabilizing solution | | | |
| formalin (37%) | | 5.0 | ml |
| polyoxyethylene-p-monononylphenyl ether (mean polymerization degree: 10) | | 0.5 | ml |
| water | ad | 1000 | ml |
| pH (not adjusted) | | | |

EXAMPLE 6

The same procedures used in Example 1 were repeated to form Sample A' except that a cellulose triacetate substrate was used and that the amount of the coupler coated was changed to 2 mmole/$m^2$.

In addition, Samples B', C', D', E', F' and G' were prepared in the same manner as used above except that equimolar amounts of couplers (5), (16), (60) and (61) and comparative couplers (C-2') and (C-10') (whose structural formulae are shown below) were substituted for the coupler (1) used above. Moreover, Samples H', I', J', K' and L' were prepared in the same manner except that a half (5 g) of the amount of the dibutyl phthalate was replaced with the polymers listed in the following Table 3.

Comparative Coupler (C-2')

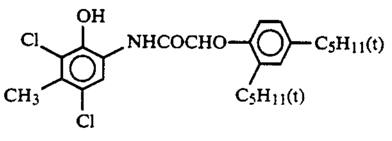

Comparative Coupler (C-10')

-continued

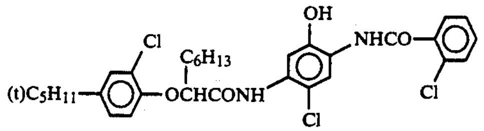

The resulting Samples were treated in the same manner as used in Example 1 using the same processings and processing solutions as those used in Example 1.

These treated film Samples were subjected to sensitometric analysis and then absorption spectra thereof were determined with a spectrophotometer. Subsequently, the decoloration in the dark of these Samples was determined under conditions of 100° C. for 16 days. In the following Table 3, $\Delta\lambda\frac{1}{2}$ means the half band width expressed in nm unit and $\Delta\lambda_{0.1}$ means the value determined from the relation: $\lambda_{max}-\lambda_{0.1}$ (nm) wherein $\lambda_{0.1}$ is the wavelength at which the absorbancy in short wavelength region becomes 0.1 if that at the wavelength of maximum absorption ($\lambda_{max}$) is normalized to be 1.0. They both indicate the sharpness of absorption. More specifically, the smaller the values $\Delta\lambda_{0.1}$ and $\Delta\lambda\frac{1}{2}$, the higher the sharpness of absorption.

TABLE 3

| Sample | Coupler | Polymer (average M.W.) | Fogging | $\Delta\lambda\frac{1}{2}$ nm | $\Delta\lambda_{0.1}$ nm | Fastness (%)[1)] |
|---|---|---|---|---|---|---|
| A' | (1) | — | 0.08 | 94 | 111 | 24 |
| B' | (5) | — | 0.08 | 95 | 114 | 36 |
| C' | (16) | — | 0.07 | 95 | 115 | 42 |
| D' | (60) | — | 0.06 | 94 | 111 | 38 |
| E' | (61) | — | 0.07 | 96 | 118 | 40 |
| F'(*) | (C-2') | — | 0.04 | 120 | 129 | 41 |
| G'(*) | (C-10') | — | 0.03 | 116 | 126 | 56 |
| H' | (1) | P-3 (40000) | 0.04 | 95 | 111 | 44 |
| I' | (5) | P-57(60000) | 0.03 | 95 | 116 | 51 |
| J' | (16) | P-57(60000) | 0.02 | 96 | 117 | 62 |
| K' | (60) | P-60(50000) | 0.03 | 95 | 113 | 54 |
| L' | (61) | P-60(50000) | 0.03 | 98 | 119 | 57 |

(*)Comparative Example.

1): The fastness is expressed in the dye density (%) remaining even after allowing to stand at 100° C. for 16 days (the initial dye density is defined to be 1.0).

As seen from the results listed in Table 3, Samples of the present invention have high sharpness of absorption or further improved fastness of color images.

EXAMPLE 7

Sample 701 was prepared in the same manner used in Example 2 except that 4-hydroxy 6-methyl-1,3,3a,7 tetrazaindene was added to the blue-sensitive emulsion layers and the green-sensitive emulsion layers in amounts of $1\times10^{-4}$ mole and $2\times10^{-4}$ mole per mole of the silver halide respectively, that 0.02 g cf a color image stabilizer (Cpd-9) was added to the green-sensitive emulsion layer (3rd layer) and that 0.32 g of a cyan coupler (ExC) was substituted for the cyan couplers (C-1) and (C-2) and the amount of the color image stabilizer (Cpd 6) was changed to 0.17 g in the red-sensitive layer (5th layer).

(ExM): magenta coupler
1:1 (molar ratio) mixture of the following compounds:

-continued

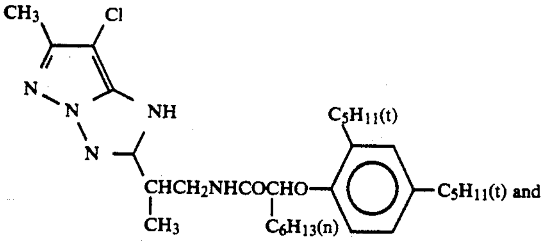

and

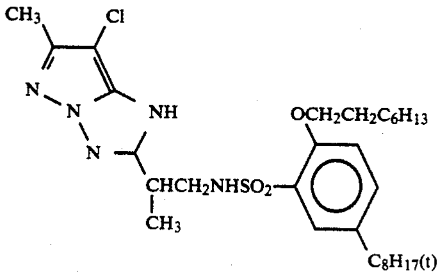

(ExC): cyan coupler

2:4:4 (weight ratio) mixture of the following compounds:

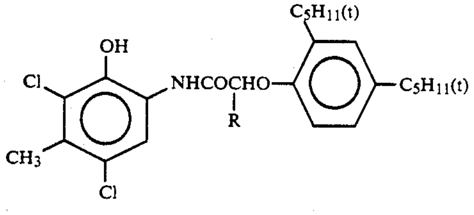

R = $C_2H_5$; $C_4H_9$ and

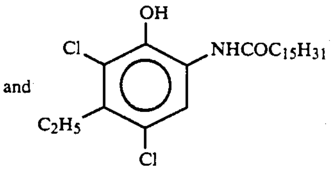

(Cpd-8): color image stabilizer

1:1:1 (weight ratio) mixture of the following compounds:

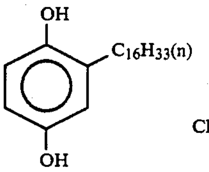

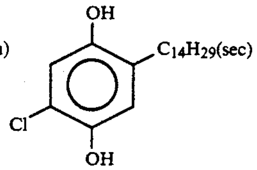

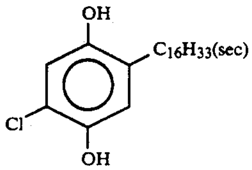

(Cpd-9): color image stabilizer

-continued

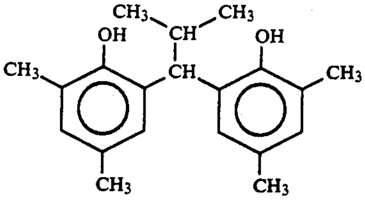

Other compounds used in this Example were the same as those employed in Example 2.

Then Samples 702 to 709 were prepared in the same manner used above except that the couplers ExY, ExM and ExC used in the 1st, 3rd and 5th layers respectively were replaced with equimolar amounts of those listed in the following Table 4 and that the amount of Cpd-7 in the 5th layer was changed to those listed in Table 4.

These Samples were exposed with a sensitometric wedge and further exposed to light for evaluating color reproduction. The exposed Samples were subjected to a continuous processing (a running test) till the amount of the replenisher for the developer reached two times the volume of the color developing tank according to the same processes used in Example 2 using a paper processing apparatus. The results obtained are summarized in Table 4.

TABLE 4

| Sample | 1st Layer ExY | 3rd Layer ExM | 5th Layer ExC | 5th Layer Cpd-7 | Remarks |
|---|---|---|---|---|---|
| 701 | (ExY) | (ExM) | (ExC) | 0.40 g | Comp. Ex. |
| 702 | (Y) | (M-4) | (16) | 0 g | Ex. |
| 703 | (Y) | (M-4) | (16) | 0.40 g | Ex. |
| 704 | (Y) | (ExM) | (16) | 0 g | Ex. |
| 705 | (ExY) | (M-4) | (16) | 0 g | Ex. |
| 706 | (ExY) | (ExM) | (16) | 0.40 g | Ex. |
| 707 | (ExY) | (ExM) | (60) | 0.80 g | Ex. |
| 708 | (ExY) | (ExM) | (61) | 0.40 g | Ex. |
| 709 | (Y-11) | (ExM) | (61) | 0.40 g | Ex. |

The compound (Cpd-7) is identical with the foregoing polymer P-57; (ExY) with the foregoing mixture of (Y-1) and (Y-4) and (ExM) with the foregoing mixture of (M-10) and (M-15respectively.

(Y) is a comparative yellow coupler having the following structure:

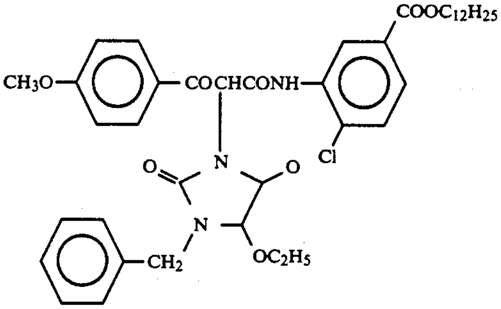

Aa seen from the foregoing results, these Samples except for Sample 701 are excellent in the cyan color reproduction; Sample 704 is excellent in the reproduction of magenta, Sample 705 in that of yellow to green, and Samples 706 to 709 in that of Yellow to green and magenta. In addition, Samples 703, 706 to 709 have improved fastness to heat of cyan color images. Further, the fogging of cyan observed on Sample 702 is slightly great while that observed on other Samples is low.

EXAMPLE 8

The same procedures used in Example 3 were repeated to form Sample 801 except that the average particle size of the silver chlorobromide used in 6th layer (high speed green-sensitive emulsion layer) was changed to 0.4μ, that the size distribution of the silver bromide used in 7th layer was 16%, that the size distribution of the silver bromide used in 12th layer was 18% and that in the preparation of the emulsion EM-1, 3,4-dimethyl-1,3-thiazoline-2-thion was used in an amount of 0.3 g per mole of silver.

In addition, Samples 802 to 810 were prepared in the same manner used above except that the cyan couplers ExC 1, 2 and 3 used in the 3rd and 4th layers and the yellow couplers ExY-1 and 2 used in 11th and 12th layers were replaced with equimolar amounts of those listed in the following Table 5.

These Samples 801 to 810 were exposed for sensitometry and for evaluating the color reproduction and then treated according to the processes used in Example 3, using the same processing solutions as used in Example 3.

TABLE 5

| | Cyan Coupler (3rd, 4th Layers) | | | Yellow Coupler (11th, 12th Layers) | |
|---|---|---|---|---|---|
| Sample | ExC-1 | ExC-2 | ExC-3 | ExY-1 | ExY-2 |
| 801(*) | ExC-1 | ExC-2 | ExC-3 | ExY-1 | ExY-2 |
| 802 | (16) | ExC-2 | ExC-3 | ExY-1 | (Y-11) |
| 803 | ExC-1 | (16) | ExC-3 | ExY-1 | (Y-13) |
| 804 | (16) | (16) | ExC-3 | ExY-1 | ExY-1 |
| 805 | (16) | (16) | (16) | (Y-11) | (Y-11) |
| 806 | (57) | (57) | (57) | (Y-11) | (Y-11) |
| 807 | (58) | (58) | (58) | (Y-4) | (Y-4) |
| 808 | (60) | (60) | (60) | (Y-4) | (Y-4) |
| 809 | (61) | (61) | (61) | (Y-11) | (Y-11) |
| 810 | (61) | (61) | (61) | (Y-15) | (Y-15) |

ExC-1, ExC-2, ExM-3, ExY 1 and ExY-2 are identical with the foregoing compounds (C-6), (C-10), (M 24), (Y-1) and (Y-7), respectively.

When Samples 802 to 810 of the present invention were compared with Sample 801 as a comparative one, the former is excellent, in particular, in the reproduction of cyan and has low fogging of cyan and good fastness to heat of the cyan color images.

EXAMPLE 9

The same procedures used in Example 4 were repeated to form Sample 901 except that, in the 3rd layer, EX-2 was replaced with Cyan Coupler (60) and 0.060 g of Cpd-1 and 0.300 g of B-3 were used instead of 0.06 g of HBS-1; that, in the 4th layer, EX-2 was replaced with Cyan Coupler (60) and 0.060 g of Cpd-1 and 0.400 g of B-3 were used instead of 0.06 g of HBS-1; and that, in the 7th and 8th layers, EX-6 was replaced with M-9 in amounts of 0.250 and 0.09 g respectively.

Cpd-1:

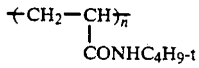

average molecular weight: 60,000

B-3

-continued

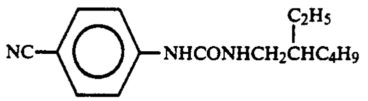

M-9

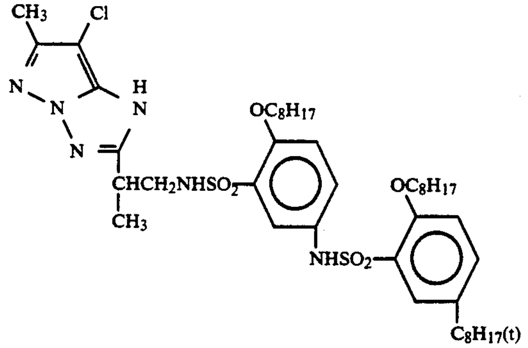

Other compounds used in this Example were the same as those employed in Example 4.

Moreover, Samples 902 to 910 were prepared in the same manner as described above except that Cyan Coupler (60) used in 3rd and 4th layers of Sample 901 was replaced with equimolar amounts of cyan couplers (16), (17), (57), (58), (61), (31), (32), (63) and (65) respectively.

The resulting Samples 901 to 910 were exposed through a red filter and then treated in the same manner as used in Example 4, using the same processing solutions.

The resulting developed Samples were subjected to a sensitometric measurement and spectroscopic measurement and it was found that these Samples of the present invention show sharp absorptions in short wavelength region at a high developed color density.

EXAMPLE 10

Sample 1001 was prepared in the same manner used in Example 5 except that P-57 was added to 3rd, 4th and 5th layers in amounts of 0.2 g/m$^2$, 0.5 g/m$^2$ and 0.5 g/m$^2$, respectively and that the thickness of the 4th and 5th layers were changed to 1.8 μ.

In addition, Samples 1002 to 1006 were prepared in the same manner as used above except that all the cyan couplers C-1, C-2, C-6 and C-8 used in 3rd, 4th and 5th layers Of Sample 1001 were replaced with equimolar amounts of couplers (16), (57), (58), (60) and (61) of the present invention.

These Samples 1001 to 1006 were exposed for sensitometric analysis and for evaluation of the color reproduction and then treated according to the same processings used in Example 5, using the same processing solutions.

The resulting developed Samples were subjected to spectroscopic measurement and the color reproduction thereof was evaluated. As a result, it was found that the resulting cyan color images showed excellent spectroscopic properties and were also excellent in the color reproduction in the Yellow to green and magenta regions.

What is claimed is:

1. A silver halide color photographic light-sensitive material comprising a substrate provided thereon with at least one layer of a silver halide emulsion containing a yellow dye-forming coupler, at least one layer of a silver halide emulsion containing a magenta dye-forming coupler and at least one layer of a silver halide emulsion containing a cyan dye-forming coupler, wherein the cyan dye-forming coupler is one represented by the following general formula (II):

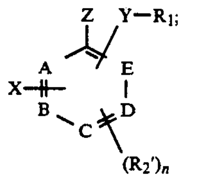

(II)

wherein A, B, C, D and E each represent a nitrogen atom, or carbon atom, or a carbon atom to which a hydrogen atom is bonded, provided that one or two of A, B, C, D and E represent a nitrogen atom, $R_1$ represents an aliphatic group having 1 to 36 carbon atoms, an aromatic group having 6 to 36 carbon atoms or a heterocyclic group which is a 3- to 8-membered cyclic ring comprising carbon atoms and at least one hetero atom selected from the group consisting of O, S, N and P, provided that the ring may comprise two or more such rings condensed with one another or with a benzene ring; $R_2'$ represents an aliphatic, aromatic, heterocyclic, alkoxy, aryloxy, alkenyloxy, amino, ester, acyl, amido, sulfamido, imido, ureido, aliphatic or aromatic sulfonyl, aliphatic or aromatic thio, hydroxy, cyano or carboxyl group or a halogen atom, with the proviso that if $R_2'$ is a hydroxyl group and is present at the o- or p-position with respect to a nitrogen atom of the heterocyclic ring, a cyclic ketone can be formed through tautomerism, and with the proviso that if the ring containing substituents A, B, C, D and E of formula (II) is a pyridyl ring and is tautomerized to form a ketone and an $R_2'$ group may be bonded to a nitrogen atom of the tautomerized ring through substitution for a hydrogen atom previously bonded to that same nitrogen atom of the tautomerized pyridyl ring, that $R_2'$ group represents an aliphatic, aromatic, heterocyclic, acyl, sulfonyl, aliphatic or aromatic oxy or amino group; X represents a hydrogen or halogen atom, an alkoxy group, an aryloxy group, an acyloxy group, an aliphatic or aromatic sulfonyloxy group, an aliphatic or aromatic acylamino group, an aliphatic or aromatic sulfonamido group, an alkoxycarbonyloxy group, an aryloxycarbonyloxy group, an aliphatic or aromatic thio group, a carbamoylamino group, a 5- or 6-membered nitrogen atom-containing heterocyclic group, an imido group or an aromatic azo group; Y represents a group selected from $-N(R_3)-CO-$, $-N(R_3)-SO_2-$, $-N(R_3)-CO-N(R_4)-$, $-N(R_3)-SO_2-N(R_4)-$, $-N(R_3)-COO-$, $-N(R_3)-SO_2O-$, $-CO-N(R_4)-$ or $-SO_2-N(R_4)-$ wherein $R_3$ and $R_4$ each represent a hydrogen atom or an aliphatic, aromatic or heterocyclic group; Z represents a dissociative group having an acid dissociation constant pka of 5 to 12; and n represents 0, 1 and 2, with the proviso that if n is 2, the two $R_2'$ groups can be the same or different, and may be bonded together to form a ring, or if n is 1 or more, $R_1$ may form a ring together with $R_2'$, and at least one of $R_1$, $R_2'$ and X may have, as substituents, one or more heterocyclic residues of general formula (II) from which $R_1$, $R_2'$ or X has been removed, and the magenta dye-forming coupler is a pyrazoloazole-type magenta coupler.

2. The silver halide photographic light-sensitive material of claim 1 wherein the pyrazoloazole type magenta coupler is selected from those represented by the following general formula (M):

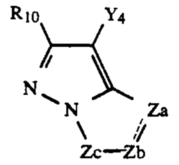

(M)

wherein $R_{10}$ represents a hydrogen atom or a substituent; $Y_4$ represents a hydrogen atom or an elimination group, Za, Zb and Zc each represents a methine group, a substituted methine group, $=N-$ or $-NH-$, provided that one of the bonds Za—Zb and Zb—Zc is a double bond and the other is a single bond, if the end Zb—Zc is a carbon-carbon double bond, it may be a part of the aromatic ring, the magenta coupler may form a dimer or a higher polymer at the position of $R_{10}$ or $Y_4$, in which if Za, Zb or Zc is a substituted methine group, the dimer or the higher polymer may be formed at the substituted methine group.

3. A silver halide color photographic light-sensitive material comprising a substrate provided thereon with at least one layer of a silver halide emulsion containing a yellow dye-forming coupler, at least one layer of a silver halide emulsion containing a magenta dye-forming coupler and at least one layer of a silver halide emulsion containing a cyan dye-forming coupler, wherein the cyan dye-forming coupler is one represented by the following general formula (II):

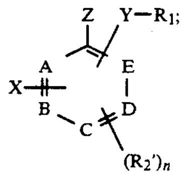

(II)

wherein A, B, C, D and E each represent a nitrogen atom, or a carbon atom, or a carbon atom to which a hydrogen atom is bonded, provided that one or two of A, B, C, D and E represent a nitrogen atom, $R_1$ represents an aliphatic group having 1 to 36 carbon atoms, an aromatic group having 6 to 36 carbon atoms or a heterocyclic group which is a 3- to 8-membered cyclic ring comprising carbon atoms and at least one hetero atom selected from the group consisting of O, S, N and P, provided that the ring may comprise two or more such rings condensed with one another or with a benzene ring; $R_2'$ represents an aliphatic, aromatic, heterocyclic, alkoxy, aryloxy, alkenyloxy, amino, ester, acyl, amido, sulfamido, imido, ureido, aliphatic or aromatic sulfonyl, aliphatic or aromatic thio, hydroxy, cyano or carboxyl group or a halogen atom, with the proviso that if $R_2'$ is a hydroxyl group and is present at the o- or p-position with respect to a nitrogen atom of the heterocyclic ring, a cyclic ketone can be formed through tautomerism, and with the proviso that if the ring containing substituents A, B, C, D and E of formula (II) is a pyridyl ring and is tautomerized to form a ketone and an $R_2'$ group may be bonded to a nitrogen atom of the tautomerized ring through substitution for a hydrogen atom previously bonded to that same nitrogen atom of the tautomerized pyridyl ring, that $R_2'$ group represents and aliphatic, aromatic, heterocyclic, acyl, sulfonyl, aliphatic or aromatic oxy or amino group; X represents hydrogen or halogen atom, an alkoxy group, an aryloxy group, an acyloxy group, an aliphatic or aromatic sulfonyloxy group, an aliphatic or aromatic acylamino group, an aliphatic or aromatic sulfonamido group, an alkoxycarbonyloxy group, an aryloxycarbonyloxy group, an aliphatic or aromatic thio group, a carbamoylamino group, a 5- or 6-membered nitrogen atom-containing heterocyclic group, an imido group or an aromatic azo group; Y represents a group selected from —$N(R_3)$—CO—, —$N(R_3)$—$SO_2$—, —$N(R_3)$—CO—$N(R_4)$—, —$N(R_3)$—$SO_2$—$N(R_4)$—, —$N(R_3)$—COO—, —$N(R_3)$—$SO_2O$—, —CO—$N(R_4)$— or —$SO_2$—$N(R_4)$— wherein $R_3$ and $R_4$ each represent a hydrogen atom or an aliphatic, aromatic or heterocyclic group; Z represents a dissociative group having an acid dissociation constant pka of 5 to 12; and n represents 0, 1 and 2, with the proviso that if n is 2, the two $R_2'$ groups can be the same or different, and may be bonded together to form a ring, or if n is 1 or more, $R_1$ may form a ring together with $R_2'$, and at least one of $R_1$, $R_2'$ and X may have, as substituents, one or more heterocyclic residues of general formula (II) from which $R_1$, $R_2'$ or X has been removed, and the cyan dye-forming coupler is added to the silver halide emulsion layer in the form of an emulsion of lipophilic fine particles obtained by dispersing a solution of the cyan dye-forming couple and at least one water-insoluble and organic solvent-soluble homo- or co-polymer into an aqueous solution.

4. The silver halide photographic light-sensitive material of claim 3 wherein the water-insoluble and organic solvent-soluble polymer has a repeating unit containing a —CO— bond in the main chain or the side chain thereof.

5. The silver halide photographic light-sensitive material of claim 4 wherein the water-insoluble and organic solvent-soluble polymer is selected from the group consisting of those listed below:

a') water-insoluble and organic solvent-soluble homopolymers and copolymers whose repeating unit has a —COO— bond in the main chain or the side chain thereof; and b') water-insoluble and organic solvent-soluble homopolymers and copolymers whose repeating unit has a group represented by the general formula : —CO—$N(G_1)G_2$ (wherein either $G_1$ or $G_2$ represents a hydrogen atom, a substituted or unsubstituted alkyl or aryl group and the other represents a substituted or unsubstituted alkyl or aryl group.

6. A silver halide light-sensitive material comprising a substrate provided thereon with a hydrophilic colloidal layer containing at least one cyan dye-forming coupler represented by the following general formula (I):

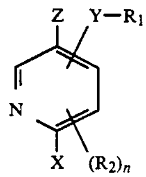

(I)

wherein $R_1$ represents an aliphatic group having 1 to 36 carbon atoms, an aromatic group having 6 to 36 carbon atoms or a heterocyclic group comprising a 3 to 8-membered ring; $R_2$ represents an aliphatic, aromatic, heterocyclic, alkoxy, aryloxy, alkenyloxy, amino, ester, acyl, amido, sulfamido, imido, ureido, aliphatic or aromatic sulfonyl, aliphatic or aromatic thio, hydroxy, cyano or carboxyl group or a halogen atom, with the proviso that if the pyridyl ring of the coupler of formula (I) is tautomerized to form a ketone and an $R_2$ group may be bonded to a nitrogen atom of the tautomerized ring through substitution for a hydrogen atom previously bonded to that same nitrogen atom of the tautomerized pyridyl ring, that $R_2$ group represents an aliphatic, aromatic, heterocyclic, acyl, sulfonyl, aliphatic or aromatic oxy or amino group; Y represents a group selected from —$N(R_3)$—CO—, —$N(R_3)$—$SO_2$—, —$N(R_3)$—CO—$N(R_4)$—, —$N(R_3)$—$SO_2$—$N(R_4)$—, —$N(R_3)$—COO—, —$N(R_3)$—$SO_2O$—, —CO—$N(R_4)$— or —$SO_2$—$N(R_4)$—, wherein $R_3$ and $R_4$ each represent a hydrogen atom or an aliphatic, aromatic or heterocyclic group; X represents a hydrogen or halogen atom or an aliphatic or aromatic oxy, aliphatic or aromatic thio, aliphatic or aromatic oxycarbonyloxy, aliphatic or aromatic acyloxy or aliphatic or aromatic sulfonyloxy group; Z represents a dissociative group having an acid dissociation constant pKa of 5 to 12; and n is 0, 1 or 2, with the proviso that if n is 2, the two $R_2$ groups can be the same or different or bonded to form a ring, or if n is 1 or more, $R_1$ may form a ring together with $R_2$ and at least one of $R_1$, $R_2$ and X may have, as substituents, one or more pyridyl residues of general formula (I) from which $R_1$, $R_2$ or X is removed.

7. The silver halide light-sensitive material of claim 6 wherein the coupler is dispersed by the Oil in-water dispersion method using a high-boiling organic solvent.

8. The silver halide light-sensitive material of claim 7 wherein the high-boiling organic solvent is at least one of the compounds of following formulae (VI) and (VII) or further with a co-solvent;

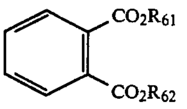

Formula (VI)

wherein $R_{61}$ and $R_{62}$ may be the same or different and they each represents an alkyl group, cycloalkyl group, alkenyl group or aryl group, with the proviso that the number of the total carbon atoms in $R_{61}$ and $R_{62}$ groups is 4 to 30;

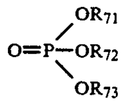

Formula (VII)

wherein $R_{71}$, $R_{72}$ and $R_{73}$ may be the same or different and they each represents an alkyl group, cycloalkyl group, alkenyl group or aryl group, with the proviso that the number of the total carbon atoms in $R_{71}$, $R_{72}$ and $R_{73}$ is 12 to 60.

9. The silver halide light-sensitive material of claim 6 wherein Y represents a group; —$N(R_3)$—CO— or —CO—$N(R_4)$—; and Z represents a hydroxyl group, sulfonamido group which may be substituted with an aliphatic, aromatic or heterocyclic group, or an active methine group having at least one electron-attractive group.

10. The silver halide light-sensitive material of claim 9 wherein Y represents —NHCO— which is bonded with the pyridine ring through the nitrogen atom; and Z represents a hydroxyl or aromatic sulfonamido group.

11. The silver halide light-sensitive material of claim 6 wherein $R_1$ forms a ring with $R_2$ or the $R_2$ groups form a ring and the ring is a 5- or 7-membered ring.

12. A silver halide color photographic light-sensitive material comprising a substrate provided thereon with at least one layer of a silver halide emulsion containing a yellow dye-forming coupler, at least one layer of a silver halide emulsion containing a magenta dye-forming coupler and at least one layer of a silver halide emulsion containing a cyan dye-forming coupler, wherein the cyan dye-forming coupler is one represented by the following general formula (II):

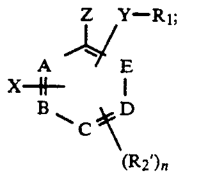
(II)

wherein A, B, C, D and E each represent a nitrogen atom, or a carbon atom to which a hydrogen atom is bonded, provided that one or two of A, B, C, D and E represent a nitrogen atom, $R_1$ represents an aliphatic group having 1 to 36 carbon atoms, an aromatic group having 6 to 36 carbon atoms or a heterocyclic group which is 3- to 8-membered cyclic ring comprising carbon atoms and at least one hetero atom selected from the group consisting of O, S, N and P, provided that the ring may comprise two or more such rings condensed with one another or with a benzene ring; $R_2'$ represents an aliphatic, aromatic, heterocyclic, alkoxy, aryloxy, alkenyloxy, amino, ester, acyl, amido, sulfamido, imido, ureido, aliphatic or aromatic sulfonyl, aliphatic or aromatic thio, hydroxy, cyano or carboxyl group or a halogen atom, with the proviso that if $R_2'$ is a hydroxy group and is present at the o- or p-position with respect to a nitrogen atom of the heterocyclic ring, a cyclic ketone can be formed through tautomerism, and with the proviso that if the ring containing substituents A, B, C, D and E of formula (II) is a pyridyl ring and is tautomerized to form a ketone and an $R_2'$ group may be bonded to a nitrogen atom of the tautomerized ring through substitution for a hydrogen atom previously bonded to that same nitrogen atom of the tautomerized pyridyl ring, that $R_2'$ group represents an aliphatic, aromatic, heterocyclic, acyl, sulfonyl, aliphatic or aromatic oxy or amino group; X represents a hydrogen or halogen atom, an alkoxy group, an aryloxy group, an acyloxy group, an aliphatic or aromatic sulfonyloxy group, an aliphatic or aromatic acylamino group, an aliphatic or aromatic sulfonamido group, an alkoxycarbonyloxy group, an aryloxycarbonyloxy group, an aliphatic or aromatic thio group, a carbamoylamino group, a 5- or 6-membered nitrogen atom-containing heterocyclic group, an imido group or an aromatic azo group; Y represents a group selected from $-N(R_3)-CO-$, $-N(R_3)-SO_2-$, $-N(R_3)-CO-N(R_4)-$, $-N(R_3)-SO_2-N(R_4)-$, —N($R_3$13 COO—, $-N(R_3)-SO_2O-$, $-CO-N(R_4)-$ or $-SO_2-N(R_4)-$ wherein $R_3$ and $R_4$ each represent a hydrogen atom or an aliphatic, aromatic or heterocyclic group; Z represents a dissociative group having an acid dissociation constant pka of 5 to 12; and n represents 0, 1 and 2, with the proviso that if n is 2, the two $R_2'$ groups can be the same or different, and may be bonded together to form a ring, or if n is 1 or more, $R_1$ may form a ring together with $R_2'$, and at least one of $R_1$, $R_2'$ and X may have, as substituents, one or more heterocyclic residues of general formula (II) from which $R_1$, $R_2'$ or X has been removed, and the yellow dye-forming coupler is an α-pivaloylacetonanilide-type yellow dye-forming coupler.

13. The silver halide photographic light-sensitive material of claim 12 wherein the couple represented by Formula (II) is a member selected from the group consisting of those represented by the following general formulae:

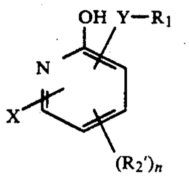
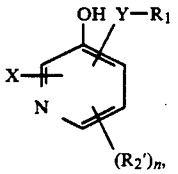
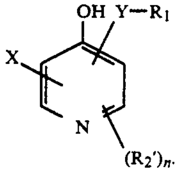

14. The silver halide photographic light-sensitive material of claim 12 wherein the coupler represented by Formula (II) is a member selected from the group consisting of those represented by the following general formula (III):

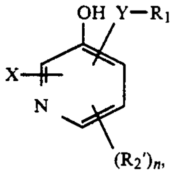
(III)

15. The silver halide Photographic light-sensitive material of claim 14 wherein the group $-Y-R_1$ of the general formula (III) is present at the 2- or 5-position of the pyridine ring.

16. The silver halide photographic light-sensitive material of claim 12 wherein the α-pivaloylacetoanilide type yellow dye-forming coupler is selected from those represented by the following general formula (Y):

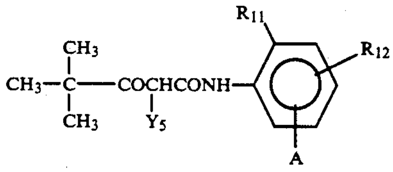
(Y)

wherein $R_{11}$ represents a halogen atom, an alkoxy group, an aryloxy group or an alkyl group; $R_{12}$ represents a hydrogen atom, a halogen atom or an alkoxy group; A represents a group:$-NHCOR_{13}-$, $-NHSO_2-R_{13}$, $-SO_2NHR_{13}$, $-COOR_{13}$ or $-SO_2N(R_{14})-R_{13}$ (wherein $R_{13}$ and $R_{14}$ each represents an alkyl, aryl or acyl group); and $Y_5$ represents an elimination group.

17. The silver halide photographic light-sensitive material of claim 12, wherein the nitrogen atom of the heterocyclic ring of formula (II) has no substituent, Y represents —N($R_3$)—CO— or —CO—N($R_4$)—; X represents a hydrogen atom, a halogen atom, an aliphatic or aromatic oxy group, an aliphatic or aromatic thio group, an aliphatic or aromatic oxycarbonyloxy group, an aliphatic or aromatic acyloxy group or n aliphatic or aromatic sulfonyloxy group and Z represents a hydroxyl group, a sulfonamide group which may be substituted with an aliphatic, aromatic or heterocyclic group or an active methine group having at least one electron-attractive group.

* * * * *